(12) United States Patent
Macoviak et al.

(10) Patent No.: US 9,224,180 B2
(45) Date of Patent: *Dec. 29, 2015

(54) REMOTELY-EXECUTED MEDICAL DIAGNOSIS AND THERAPY INCLUDING EMERGENCY AUTOMATION

(71) Applicant: Remedev, Inc., La Jolla, CA (US)

(72) Inventors: John A. Macoviak, La Jolla, CA (US); Stefanos Poulis, Cardiff-By-The-Sea, CA (US); Andreas Vlachos, Cambridge (GB)

(73) Assignee: REMEDEV, INC., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/092,783

(22) Filed: Nov. 27, 2013

(65) Prior Publication Data

US 2014/0089001 A1   Mar. 27, 2014

Related U.S. Application Data

(63) Continuation of application No. 13/982,365, filed as application No. PCT/US2012/062865 on Oct. 31,
(Continued)

(51) Int. Cl.
*G06Q 50/00* (2012.01)
*G06Q 50/22* (2012.01)
*G06F 19/00* (2011.01)

(52) U.S. Cl.
CPC .............. *G06Q 50/22* (2013.01); *G06F 19/322* (2013.01); *G06F 19/328* (2013.01); *G06F 19/3418* (2013.01); *G06F 19/3456* (2013.01); *G06F 19/3462* (2013.01)

(58) Field of Classification Search
CPC ................. A61B 5/0002; G06Q 50/22–50/24; G06F 19/34; G06F 19/3456; G06F 17/3462; G06F 19/3468
See application file for complete search history.

(56) References Cited

U.S. PATENT DOCUMENTS

| | | |
|---|---|---|
| 4,489,387 A | 12/1984 | Lamb et al. |
| 4,491,725 A | 1/1985 | Pritchard |
| 4,731,725 A | 3/1988 | Suto et al. |
| 4,847,764 A | 7/1989 | Halvorson |

(Continued)

FOREIGN PATENT DOCUMENTS

WO   WO-2013/077977   5/2013

OTHER PUBLICATIONS

PCT/US2012/062865 International Search Report and Written Opinion dated Mar. 15, 2013.
(Continued)

*Primary Examiner* — Sheetal R Paulson
(74) *Attorney, Agent, or Firm* — Wilson Sonsini Goodrich & Rosati

(57) ABSTRACT

Devices, systems, methods, and software for providing remote medical diagnosis and therapy to a subject comprising: a module for conducting telecommunications with a telemedicalist; a module for applying a diagnostic or a therapeutic analysis; an apparatus for dispensing one or more medical items from an inventory of medical items, the inventory of medical items risk profiled to a subject, a population, a venue, or a situation; and optionally, a biosensor apparatus.

25 Claims, 28 Drawing Sheets

Related U.S. Application Data 2012, now abandoned, and a continuation of application No. PCT/US2012/034292, filed on Apr. 19, 2012.

(60) Provisional application No. 61/641,685, filed on May 2, 2012, provisional application No. 61/563,472, filed on Nov. 23, 2011.

(56) References Cited

U.S. PATENT DOCUMENTS

| | | | |
|---|---|---|---|
| 4,945,476 | A | 7/1990 | Bodick et al. |
| 4,975,840 | A | 12/1990 | DeTore et al. |
| 5,099,424 | A | 3/1992 | Schneiderman |
| 5,130,936 | A | 7/1992 | Sheppard et al. |
| 5,235,510 | A | 8/1993 | Yamada et al. |
| 5,404,292 | A | 4/1995 | Hendrickson |
| 5,410,471 | A | 4/1995 | Alyfuku et al. |
| 5,437,278 | A | 8/1995 | Wilk |
| 5,492,117 | A | 2/1996 | Eisenberg et al. |
| 5,517,405 | A | 5/1996 | McAndrew et al. |
| 5,594,637 | A | 1/1997 | Eisenberg et al. |
| 5,657,236 | A | 8/1997 | Conkright |
| 5,692,501 | A | 12/1997 | Minturn |
| 5,713,485 | A | 2/1998 | Liff et al. |
| 5,746,204 | A | 5/1998 | Schauss |
| 5,764,923 | A | 6/1998 | Tallman et al. |
| 5,796,759 | A | 8/1998 | Eisenberg et al. |
| 5,807,256 | A | 9/1998 | Taguchi et al. |
| 5,867,821 | A | 2/1999 | Ballantyne et al. |
| 5,956,689 | A | 9/1999 | Everhart, III |
| 5,993,386 | A | 11/1999 | Ericsson |
| 6,004,020 | A | 12/1999 | Bartur |
| 6,059,724 | A | 5/2000 | Campell et al. |
| 6,063,026 | A | 5/2000 | Schauss et al. |
| 6,068,156 | A | 5/2000 | Liff et al. |
| 6,101,478 | A | 8/2000 | Brown |
| 6,206,829 | B1 | 3/2001 | Iliff |
| 6,219,587 | B1 | 4/2001 | Ahlin et al. |
| 6,234,964 | B1 | 5/2001 | Iliff |
| 6,322,504 | B1 | 11/2001 | Kirshmer |
| 6,334,192 | B1 | 12/2001 | Karpf |
| 6,352,200 | B1 | 3/2002 | Schoonen et al. |
| 6,602,469 | B1 | 8/2003 | Maus et al. |
| 6,752,787 | B1 | 6/2004 | Causey et al. |
| 6,757,898 | B1 | 6/2004 | Ilsen et al. |
| 7,048,141 | B2 | 5/2006 | Abdulhat et al. |
| 7,072,738 | B2 | 7/2006 | Bonney et al. |
| 7,306,562 | B1 | 12/2007 | Baykal |
| 7,379,885 | B1 | 5/2008 | Zakim |
| 7,395,216 | B2 | 7/2008 | Rosenfeld et al. |
| RE40,453 | E | 8/2008 | Lasher et al. |
| RE40,510 | E | 9/2008 | Lasher et al. |
| 7,447,643 | B1 | 11/2008 | Olson et al. |
| 7,483,766 | B1 | 1/2009 | Frankel |
| 7,739,126 | B1 | 6/2010 | Cave et al. |
| 7,853,355 | B1 | 12/2010 | Willemse et al. |
| 7,912,582 | B1 | 3/2011 | Holtje et al. |
| 7,996,106 | B2 | 8/2011 | Ervin |
| RE42,730 | E | 9/2011 | Lasher et al. |
| 8,014,170 | B2 | 9/2011 | Mori et al. |
| 8,751,039 | B1 | 6/2014 | Macoviak et al. |
| 2002/0004725 | A1 | 1/2002 | Martin et al. |
| 2002/0029157 | A1* | 3/2002 | Marchosky ............... 705/3 |
| 2002/0070226 | A1 | 6/2002 | Liff et al. |
| 2002/0077865 | A1 | 6/2002 | Sullivan |
| 2002/0087276 | A1 | 7/2002 | Otvos |
| 2002/0133379 | A1 | 9/2002 | Lewis et al. |
| 2002/0169637 | A1* | 11/2002 | Akers et al. ............... 705/3 |
| 2002/0198738 | A1 | 12/2002 | Osbourne |
| 2003/0055531 | A1 | 3/2003 | Liff et al. |
| 2003/0065241 | A1* | 4/2003 | Hohnloser ............... 600/1 |
| 2003/0074218 | A1 | 4/2003 | Liff et al. |
| 2003/0105731 | A1 | 6/2003 | Lapointe et al. |
| 2003/0189058 | A1 | 10/2003 | Liff et al. |
| 2003/0191671 | A1 | 10/2003 | Ulrich et al. |
| 2003/0216831 | A1 | 11/2003 | Hart et al. |
| 2004/0037738 | A1 | 2/2004 | Maus et al. |
| 2004/0065053 | A1 | 4/2004 | Rice et al. |
| 2004/0088187 | A1 | 5/2004 | Chudy et al. |
| 2004/0133452 | A1 | 7/2004 | Denny, Jr. et al. |
| 2004/0164146 | A1 | 8/2004 | Rosenblum |
| 2004/0210548 | A1 | 10/2004 | Ketcherside, Jr. et al. |
| 2004/0215369 | A1 | 10/2004 | Rosenblum |
| 2005/0010088 | A1 | 1/2005 | Iliff |
| 2005/0010444 | A1 | 1/2005 | Iiff |
| 2005/0071200 | A1 | 3/2005 | Franklin et al. |
| 2005/0080462 | A1 | 4/2005 | Jenkins et al. |
| 2005/0113969 | A1 | 5/2005 | Spano, Jr. et al. |
| 2005/0171512 | A1 | 8/2005 | Flaherty et al. |
| 2006/0173708 | A1 | 8/2006 | Vining et al. |
| 2006/0224416 | A1 | 10/2006 | Lloyd et al. |
| 2006/0265253 | A1 | 11/2006 | Rao et al. |
| 2007/0084150 | A1 | 4/2007 | Siegel et al. |
| 2007/0093934 | A1* | 4/2007 | Garneau, III ............... 700/236 |
| 2007/0094048 | A1 | 4/2007 | Grichnik et al. |
| 2007/0118399 | A1 | 5/2007 | Avinash et al. |
| 2007/0119930 | A1 | 5/2007 | Debenberg et al. |
| 2007/0168308 | A1 | 7/2007 | Wang et al. |
| 2007/0179769 | A1 | 8/2007 | Grichnik et al. |
| 2007/0293982 | A1 | 12/2007 | Rosenblum |
| 2008/0009684 | A1 | 1/2008 | Corsetti |
| 2008/0015894 | A1 | 1/2008 | Miller |
| 2008/0033761 | A1 | 2/2008 | Brummel et al. |
| 2008/0097943 | A1 | 4/2008 | Kelly et al. |
| 2008/0162352 | A1 | 7/2008 | Gizewski |
| 2008/0179387 | A1 | 7/2008 | Cantlay et al. |
| 2008/0288105 | A1 | 11/2008 | Mauger et al. |
| 2009/0048712 | A1 | 2/2009 | Rosenblum |
| 2009/0069746 | A1 | 3/2009 | Miller et al. |
| 2009/0240528 | A1* | 9/2009 | Bluth ............... 705/3 |
| 2009/0295575 | A1 | 12/2009 | Kennedy |
| 2010/0205009 | A1 | 8/2010 | Kostoff |
| 2010/0268190 | A1 | 10/2010 | Mielenz |
| 2010/0268377 | A1 | 10/2010 | Pinney et al. |
| 2010/2074573 | | 10/2010 | Feied et al. |
| 2010/0324728 | A1 | 12/2010 | Rosenblum |
| 2010/0324936 | A1* | 12/2010 | Vishnubhatla et al. ............ 705/3 |
| 2011/0009824 | A1 | 1/2011 | Yodfat et al. |
| 2011/0092825 | A1 | 4/2011 | Gopinathan et al. |
| 2014/0058755 | A1 | 2/2014 | Macoviak et al. |

OTHER PUBLICATIONS

PCT/US2014/017811 International Search Report and Written Opinion dated Jun. 12, 2014.

PCT/US2012/062865 International Preliminary Report on Patentability dated Jun. 5, 2014.

U.S. Appl. No. 14/253,450, filed Apr. 15, 2014, Macoviak et al.

Alonzo & Pepe, Distribution Free ROC Analysis Using Binary Regression Technique, Biostatistics (2002), 3(3):421-432.

Apache II calculator (available at www.globalrph.com/apacheii.htm) downloaded Apr. 22, 2011.

Breiman, Random Forests, Machine Learning (2001), 45(1):5-32.

Decision Support Systems (available at www.openclinical.org/dss.html) downloaded Apr. 22, 2011.

Dxplain (available at http://lcs.mgh.harvard.edu/projects/dxplain.html), Apr. 22, 2011.

Goldman et al., A Computer Protocol to Predict Myocardial Infarction in Emergency Department Patients with Chest Pain, New England Journal of Medicine (1998), 318:797-803.

Hales et al. Integration of a Stand Alone Expert System with a Hospital Information System, Proceedings of the Annual Symposium on Computer Applications in Medical Care 1992:427-32.

Hales et al., Factors Impacting the Success of Computerized Preadmission Screening, Proceedings of the Annual Symposium on Computer Applications in Medical Care 1995:728-32.

Hall et al., An Electronic Application for Rapidly Calculating Charlson Comorbidity Score, BMC Cancer Dec. 2004, 4:94-101.

Mair et al., A Decision Tree for the Early Diagnosis of Acute Myocardial Infarction in Nontraumatic Chest Pain Patients at Hospital Admission, Chest (1995), 108(6):1502-09.

(56) References Cited

OTHER PUBLICATIONS

Miller, et al., INTERNIST-1: An Experimental Computer-Based Diagnostic Consultant for General Internal Medicine, New England Journal of Medicine Aug. 1982: 468-76.

Olsson et al., Rapid Emergency Medicine Score: A New Prognostic Tool for In-hospital Mortality in Nonsurgical Emergency Department Patients, Journal of Internal Medicine May 2004:579-87.

Olsson, Charlson Comorbidity Index Can Add Prognostic Information to Rapid Emergency Medicine Score as a Predictor of Long-Term Mortality, European Journal of Emergency Medicine Oct. 2005:220-24.

Olsson, Comparison of the Rapid Emergency Medicine Score and APACHE II in Nonsurgical Emergency Department Patients, Academic Emergency Medicine Oct. 2003:1040-48.

PCT/US2012/020390 International Search Report mailed Jul. 30, 2012.

Rapid Acute Physiology Score 1.0 (available at http://handheld.softpedia.com/get/Educational/Medical/Rapid-Acute-Physiology-Score-16722.shtml), Apr. 22, 2011.

Rhee et al., Rapid Acute Physiology Scoring in Transport Systems Critical Care Medicine, Oct. 1990:1119-23 downloaded Apr. 22, 2011.

Rhee et al., The Rapid Acute Physiology Score, The American Journal of Emergency Medicine Jul. 1987: 278-82.

Shortliffe & Buchanan, A Model of Inexact Reasoning in Medicine, Mathematical Biosciences, Apr. 1975:351-79.

Stineman et al., Classifying Rehabilitation Inpatients by Expected Functional Gain, Medical Care (1997) 35(9):963-73.

U.S. Appl. No. 14/017,188 Office Action mailed Nov. 7, 2013.

U.S. Appl. No. 12/986,027 Office Action Mailed Oct. 3, 2012.

Zhang et al. Model Selection via Multifold Cross Validation, The Annals of Statistics (1993) 21(1):299-313.

\* cited by examiner

REMOTELY-EXECUTED MEDICAL DIAGNOSIS AND THERAPY INCLUDING EMERGENCY AUTOMATION

CROSS REFERENCE TO RELATED APPLICATIONS

This application is a continuation of U.S. application Ser. No. 13/982,365 filed on Jul. 29, 2013, which is the National Stage Entry of International Application No. PCT/US2012/062865 filed on Oct. 31, 2012, which claims the benefit of International Application No. PCT/US2012/034292 filed on Apr. 19, 2012, U.S. Provisional Application No. 61/641,685 filed on May 2, 2012, and U.S. Provisional Application No. 61/563,472 filed on Nov. 23, 2011, all of which are hereby incorporated by reference in their entireties.

BACKGROUND OF THE INVENTION

A wide variety of circumstances result in inadequate access to healthcare for many individuals and families. Some lack adequate access because they live in isolated, rural, or other governmentally designated underserved areas. Some lack adequate access because they are uninsured or underinsured. Others live in developing countries where medical training and infrastructure is yet to be developed. Circumstances render some individuals without adequate access to healthcare in natural and manmade disaster areas and battlefields.

Moreover, the cost of providing adequate healthcare is rising. While more money is spent on health care per person in the U.S. than in any other nation in the world, in 2009, the U.S. Census Bureau reported that 16.7% of the population was uninsured. Current estimates put U.S. health care spending at approximately 16% of GDP. Growth in healthcare spending is projected to average 6.7% annually over the period 2007 through 2017. High healthcare costs also affect individuals. A 2007 study found that 62.1% of filers for bankruptcies cited high medical expenses as a contributing factor.

SUMMARY OF THE INVENTION

In one aspect, disclosed herein are computer-based devices (e.g., medical devices) for providing remote medical diagnosis and therapy to a subject, the device comprising a processor and a memory device, the device further comprising: a software module for conducting telecommunications with a telemedical care provider; a software module for applying a diagnostic or a therapeutic analysis; an apparatus for dispensing one or more medical items from an inventory of medical items, the inventory of medical items risk profiled to a subject, a population, a venue, or a situation; and optionally, a sensor apparatus, such as a biosensor. In some embodiments, the device further comprises a software module for verifying credentials of a telemedical care provider. In some embodiments, the device further comprises a software module for remote monitoring or operation of the device by the telemedical care provider. In some embodiments, the device further comprises a software module for identifying the subject. In further embodiments, the device further comprises a software module for securely accessing one or more electronic health records for the subject. In some embodiments, the inventory of medical items is determined by profiling health or economic risk for a subject or a population in advance of need for said medical items. In some embodiments, the inventory of medical items is risk profiled by determining a statistical level of likelihood that the items will be needed within 2 years, within 1 year, within 6 months, within 1 month, within 2 weeks, within 1 week, or within 1 day. In some embodiments, the inventory of medical items comprises items that require a prescription from a licensed healthcare provider. In further embodiments, the inventory of medical items comprises: one or more medications, one or more therapeutic devices, one or more diagnostic devices, or one or more diagnostic kits. In some embodiments, the sensor apparatus is a biosensor adapted to collect medical information from a subject. In some embodiments, the diagnostic or therapeutic analysis comprises performing statistical analysis, performing probability calculations, making recommendations, and making outcome predictions to predict a health or economic outcome of a patient or therapy, wherein said prediction is real-time, individualized, and probabilistic-based and uses historic, peer-reviewed health or economic data and emerging health or economic data. In some embodiments, the diagnostic or therapeutic analysis comprises: accessing one or more information sources selected from the group consisting of: electronic health records, medical databases, medical literature, economic databases, economic literature, insurance databases, and insurance literature; performing natural language processing to identify information determined to be of value in determining health and economic risks of an adverse outcome related to a health encounter; and transforming said data into numerical format useful for application in statistical modeling to determine health and economic risks of an adverse outcome related to a health encounter. In some embodiments, the diagnostic or therapeutic analysis comprises predicting acute risks, with and without one or more potential therapies, based on the severity of a condition and risks associated with each potential therapy to determine the intensity of therapy recommended. In further embodiments, the prediction of acute risks is updated in time intervals selected from the group consisting of: at least every 24 hours, at least every 12 hours, at least every 6 hours, at least every 1 hour, at least every 45 minutes, at least every 30 minutes, at least every 15 minutes, at least every 1 minute, at least every 45 seconds, at least every 30 seconds, at least every 15 seconds, and at least every 1 second. In further embodiments, the prediction of acute risks is made for a time period selected from the group consisting of: less than 72 hours, less than 48 hours, less than 24 hours, less than 12 hours, less than 8 hours, less than 4 hours, less than 2 hours, and less than 1 hour. In some embodiments, the device further comprises a software module for providing instantaneous encounter-specific financial insurance coverage, wherein said insurance includes a level of guarantee and an associated premium. In some embodiments, the device further comprises a software module for processing payment.

In another aspect, disclosed herein are systems for providing remote medical diagnosis and therapy to a subject comprising: a first networked device comprising a processor configured to perform executable instructions, the first device comprising: an apparatus for dispensing one or more medical items from an inventory of medical items, the inventory risk profiled to a subject, a population, a venue, or a situation; a second networked device comprising a processor configured to perform executable instructions, the second device comprising: at least one biosensor; wherein the first and second networked devices further comprise: a module for remote monitoring or operation by a telemedical care provider; a module for telecommunications with a telemedical care provider; and a module for applying a diagnostic or a therapeutic analysis; a networked computer comprising a processor configured to perform executable instructions, the computer accessible to a telemedical care provider, the computer provided a computer program including executable instructions operable to create an application comprising: a module for telecommunications between the first or second device, or a user thereof, and the telemedical care provider; a module for applying a diagnostic or a therapeutic analysis; and a module for remotely monitoring or operating the first or second device. In some embodiments, the inventory of medical items is determined by profiling health or economic risk for a subject or a population in advance of need for said medical items. In some embodiments, the inventory of medical items is risk profiled by determining a statistical level of likelihood that the items will be needed within 2 years, within 1 year, within 6 months, within 1 month, within 2 weeks, within 1 week, or within 1 day. In some embodiments, the first device, the second device, or the computer program comprises a module for providing instantaneous encounter-specific financial insurance coverage, wherein said insurance includes a level of guarantee and an associated premium.

In another aspect, disclosed herein are non-transitory computer readable media encoded with a computer program including instructions executable by a processor to create a remote healthcare application, wherein the application comprises: a software module for conducting telecommunications; a software module for applying a diagnostic or a therapeutic analysis; a software module for monitoring or operating a biosensor; a software module for monitoring or operating an apparatus for dispensing one or more medical items from an inventory of medical items to a subject, the inventory risk profiled to a subject, a population, a venue, or a situation; and optionally, a software module for providing instantaneous encounter-specific financial insurance coverage, wherein said insurance includes a level of guarantee and an associated premium; provided that said software modules are supervised or operated by a telemedical care provider. In some embodiments, the inventory of medical items is determined by profiling health or economic risk for a subject or a population in advance of need for said medical items. In some embodiments, the inventory of medical items is risk profiled by determining a statistical level of likelihood that the items will be needed within 2 years, within 1 year, within 6 months, within 1 month, within 2 weeks, within 1 week, or within 1 day. In some embodiments, the diagnostic or therapeutic analysis comprises performing statistical analysis, performing probability calculations, making recommendations, and making outcome predictions to predict a health or economic outcome of a patient or therapy, wherein said prediction is real-time, individualized, and probabilistic-based and uses historic, peer-reviewed health or economic data and emerging health or economic data. In some embodiments, the diagnostic or therapeutic analysis comprises: accessing one or more information sources selected from the group consisting of: electronic health records, medical databases, medical literature, economic databases, economic literature, insurance databases, and insurance literature; performing natural language processing to identify information determined to be of value in determining health and economic risks of an adverse outcome related to a health encounter; and transforming said data into numerical format useful for application in statistical modeling to determine health and economic risks of an adverse outcome related to a health encounter. In some embodiments, the diagnostic or therapeutic analysis comprises predicting acute risks, with and without one or more potential therapies, based on the severity of a condition and risks associated with each potential therapy to determine the intensity of therapy recommended. In further embodiments, the prediction of acute risks is updated in time intervals selected from the group consisting of: at least every 24 hours, at least every 12 hours, at least every 6 hours, at least every 1 hour, at least every 45 minutes, at least every 30 minutes, at least every 15 minutes, at least every 1 minute, at least every 45 seconds, at least every 30 seconds, at least every 15 seconds, and at least every 1 second. In further embodiments, the prediction of acute risks is made for a time period selected from the group consisting of: less than 72 hours, less than 48 hours, less than 24 hours, less than 12 hours, less than 8 hours, less than 4 hours, less than 2 hours, and less than 1 hour.

DETAILED DESCRIPTION OF THE INVENTION

Figure 1:
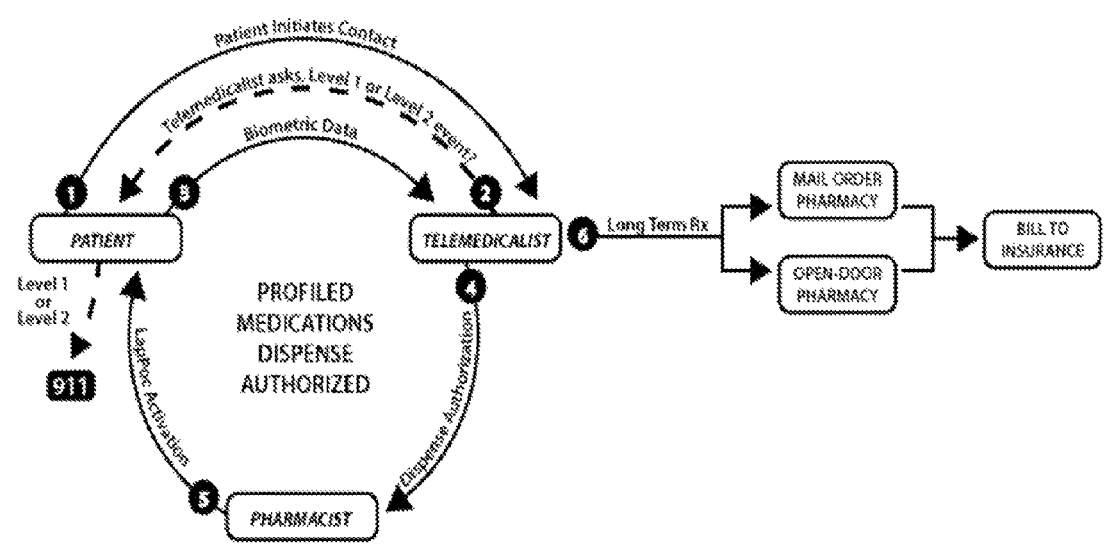
FIG. 1 shows a non-limiting example of an overall process flow for providing remote diagnosis and therapy to a subject; in this case, a process flow including interaction between a patient and a telemedical care provider, collection of patient biometric data, and remote dispensing of a short-term supply of a prescribed medication authorized by a pharmacist, followed by issuance of a long-term prescription.

Described herein are computer-based devices (e.g., medical devices) for providing remote medical diagnosis and therapy to a subject, the device comprising a processor and a memory device, the device further comprising: a software module for conducting telecommunications with a telemedical care provider; a software module for applying a diagnostic or a therapeutic analysis; an apparatus for dispensing one or more medical items from an inventory of medical items, the inventory of medical items risk profiled to a subject, a population, a venue, or a situation; and optionally, a sensor apparatus, such as a biosensor.

Also described herein, in various embodiments, are systems for providing remote medical diagnosis and therapy to a subject comprising: a first networked device comprising a processor configured to perform executable instructions, the first device comprising: an apparatus for dispensing one or more medical items from an inventory of medical items, the inventory risk profiled to a subject, a population, a venue, or a situation; a second networked device comprising a processor configured to perform executable instructions, the second device comprising: at least one biosensor; wherein the first and second networked devices further comprise: a module for remote monitoring or operation by a telemedical care provider; a module for telecommunications with a telemedical care provider; and a module for applying a diagnostic or a therapeutic analysis; a networked computer comprising a processor configured to perform executable instructions, the computer accessible to a telemedical care provider, the computer provided a computer program including executable instructions operable to create an application comprising: a module for telecommunications between the first or second device, or a user thereof, and the telemedical care provider; a module for applying a diagnostic or a therapeutic analysis; and a module for remotely monitoring or operating the first or second device.

Also described herein, in various embodiments, are non-transitory computer readable media encoded with a computer program including instructions executable by a processor to create a remote healthcare application, wherein the application comprises: a software module for conducting telecommunications; a software module for applying a diagnostic or a therapeutic analysis; a software module for monitoring or operating a biosensor; a software module for monitoring or operating an apparatus for dispensing one or more medical items from an inventory of medical items to a subject, the inventory risk profiled to a subject, a population, a venue, or a situation; and optionally, a software module for providing instantaneous encounter-specific financial insurance coverage, wherein said insurance includes a level of guarantee and an associated premium; provided that said software modules are supervised or operated by a telemedical care provider.

VARIOUS DEFINITIONS

In some embodiments, as used herein, "subject" refers to a human being requesting or in need of healthcare, healthcare-related goods and/or services or health related insurance or financial products and/or services. In some cases, a subject is a patient. In further cases, a subject interacts with the devices and systems described herein. In other cases, a subject is represented, for example, by a friend, relative, caregiver, healthcare provider, first responder, etc. and the representative interacts with the systems and devices described herein. In other embodiments, as used herein, "subject" refers to a non-human animal in need of healthcare. In further cases, a subject is a veterinary patient and an owner, rescuer, or veterinary healthcare provider interacts with the systems and devices described herein.

In some embodiments, as used herein, "onsite patient caregiver" refers to a person who has an interest in, or responsibility for, the health and welfare of a patient and is present with the patient at least once, intermittently, often, or full-time. Non-limiting examples of onsite patient caregivers include employees of a patient, members of a patient's family, hospice workers, and emergency medical technicians, paramedics, police officers, and firefighters.

In some embodiments, ss used herein, "outpatient" refers to a subject or a situation not requiring or warranting overnight hospitalization.

In some embodiments, ss used herein, "acute care" refers to short-term treatment for an urgent medical condition such as a severe injury or episode of illness.

In some embodiments, as used herein, "urgent care" refers to delivery of outpatient care outside of a hospital emergency department, usually on an unscheduled, walk-in basis.

In some embodiments, as used herein, "telemedicology" refers to a branch of medicine or surgery requiring specialized, formal, peer-reviewed training as a specialty or subspecialty of medicine concerned with safely and efficaciously providing remote diagnosis and therapy via telemedicine technology and equipment.

In some embodiments, as used herein, "telemedicologist" refers to a physician, surgeon, dentist, and/or veterinarian, specialized in telemedicology and providing remote diagnosis and therapy via telemedicine technology and equipment.

In some embodiments, as used herein, "telemedical care provider" or "TCP" refers to a healthcare worker trained and engaged in provision of remote diagnosis and therapy via telemedicine technology and equipment. The term, as used herein, includes telemedicologists as well as licensed physician extenders directly supervised by or reporting to a telemedicologist in activity related to the provision of remote diagnosis and therapy via telemedicine technology and equipment. In some cases, physician extenders directly supervised by or reporting to a telemedicologist include, nurse practitioners, physician assistants, registered nurses, licensed vocational nurses, emergency medical technicians, and the like.

In some embodiments, as used herein, "telemedicalist" refers to a physician specialized in the delivery of telemedical care to acutely ill hospitalized subjects.

In some embodiments, as used herein, "health program" refers to any legal, organizational, or financial arrangement for providing healthcare services and/or healthcare administration to subjects. In various embodiments, a health program includes, by way of non-limiting examples, a healthcare maintenance membership program, a HMO, a PPO, an IPA, a pre-paid health program, a retainer-based health program, a concierge health program, a health insurance plan or policy, and the like.

System

In some embodiments, the devices and software applications disclosed herein are integrated into systems for providing remote medical diagnosis and therapy to a subject. In some embodiments, also disclosed are methods of using the devices, software applications, and systems for providing remote medical diagnosis and therapy to a subject. In various embodiments, the systems, devices, software applications, and methods disclosed herein are useful for providing remote medical diagnosis and therapy to a subject in a wide range of healthcare encounters. In further embodiments, the systems, devices, software applications, and methods disclosed herein are useful for providing remote medical diagnosis and therapy to a subject in convenient, semi-urgent, urgent, and/or emergent healthcare encounters. In various embodiments, the systems, devices, software applications, and methods disclosed herein are useful for providing remote medical diagnosis and therapy to a subject with acute, subacute, and/or chronic illnesses.

In some embodiments, the systems for providing remote medical diagnosis and therapy to a subject include a live, licensed healthcare provider, such as a telemedical care provider, located remotely from the subject.

In some embodiments, the systems for providing remote medical diagnosis and therapy to a subject include a networked medical device that includes at least one processor, at least one memory device, and an operating system configured to perform executable instructions. In some embodiments, the medical device is accessible to a subject. In further embodiments, the medical device includes hardware and software to facilitate telecommunications between the subject (and/or a caregiver) and a live, licensed healthcare provider located remotely from the subject. In still further embodiments, the medical device includes one or more biosensors. In still further embodiments, the medical device includes an apparatus for dispensing one or more medical items from an inventory of medical items to a subject.

In some embodiments, the systems for providing remote medical diagnosis and therapy to a subject include a computer program including executable instructions operable to create an application. In various embodiments, the application includes one or more web applications, mobile applications, and/or compiled applications. In some embodiments, one or more computer programs are provided to the medical device. In some embodiments, one or more computer programs are provided to one or more remote computer systems, servers, and/or databases. In further embodiments, one or more computer programs are provided via a computer network. In various embodiments, the computer programs include one or more software modules. In some embodiments, a computer program includes a module for telecommunications between the device, or a user thereof, and a live, licensed healthcare provider. In some embodiments, a computer program includes a module for applying a diagnostic or therapeutic analysis. In various embodiments, the module for applying a diagnostic or therapeutic analysis predicts a health or economic outcome, predicts acute risks of a medical condition, with and without one or more potential therapies over various time periods. In some embodiments, a computer program includes a module for identifying subjects. In some embodiments, a computer program includes a module for identifying and/or verifying the credentials of healthcare providers. In some embodiments, a computer program includes a module for providing instantaneous encounter-specific financial insurance coverage. In further embodiments, the insurance coverage includes a level of guarantee and an associated premium.

In some embodiments, the systems, devices, and computer programs disclosed herein are monitored or supervised, to some extent, by a healthcare provider in real time. In further embodiments, the systems, devices, and software programs disclosed herein are operated by a healthcare provider in real time. In some embodiments, the systems, devices, and computer programs disclosed herein optionally operate in an unsupervised, or automated, mode. For example, in some embodiments, the systems, devices, and computer programs disclosed herein include an automated emergency mode. In further embodiments, an automated emergency mode is activated by subjective observations by a live, remote healthcare provider (e.g., choking, chest pain, etc.) or by objective measurements of a biosensor (e.g., blood $O_2$ saturation of less than 88%). In still further embodiments, in an automated emergency mode, the systems, devices, and computer programs take autonomous actions, unsupervised by a live healthcare provider, including calling 911 or otherwise activating the emergency response system.

Many system configurations are contemplated herein and are suitable. In some embodiments, the system includes a medical device that is present with, or is accessible by, a subject. In further embodiments, the subject directly accesses the telecommunications features, biosensor features, medication dispensing features, and/or diagnostic or therapeutic analysis features of the device.

In other embodiments, the system includes a plurality of medical devices. In further embodiments, the features of the system described herein are distributed among a plurality of devices in any suitable combination. For example, in some embodiments, a telecommunications module is housed in a separate device. By way of further example, in some embodiments, a biosensor module is housed in a separate device. By way of further example, in some embodiments, a medication dispensing module is housed in a separate device. By way of further example, in some embodiments, a diagnostic or therapeutic analysis module is housed in a separate device. In other embodiments, the system includes one or more medical devices with a reversibly separable, mobile component, which is present with, or is accessible by, a subject. In further embodiments, one or more of the telecommunications features, biosensor features, medication dispensing features, and/or diagnostic or therapeutic analysis features of the device are included with a reversibly separable, mobile element.

In some cases, the biosensor or biosensors are present with, or is accessible by, the subject. In other cases, the biosensor or biosensors are in a different location from the subject in need of examination (such as a centralized, stationary installation) and the subject travels to this location for examination or to provide a fluid or tissue sample. In some cases, the apparatus for dispensing medical items is present with, or is accessible by, the subject such that medical items are optionally dispensed directly to a subject or an appropriate caregiver. In other cases, the apparatus for dispensing medical items is in a different location from the subject for whom items are intended (such as a centralized, stationary installation) and the items are dispensed remotely for the subject.

In some embodiments, the devices, systems, and software are intranet-based. In some embodiments, the devices, systems, and software are Internet-based. In further embodiments, the devices, systems, and software are World Wide Web-based. In still further embodiments, the devices, systems, and software are cloud computing-based. In other embodiments, the devices, systems, and software are based on data storage devices including, by way of non-limiting examples, CD-ROMs, DVDs, flash memory devices, RAM (e.g., DRAM, SRAM, etc.), ROM (e.g., PROM, EPROM, EEPROM, etc.), magnetic tape drives, magnetic disk drives, optical disk drives, magneto-optical drives, solid-state drives, and combinations thereof.

Referring to FIG. 1, in a particular embodiment, a remote healthcare system described herein is utilized for risk profiling and dispensing a medication to a subject. In this embodiment, a patient initiates contact with a remotely located telemedical care provider (including, for example, a telemedicologist or telemedicalist) 1. The telemedical care provider interviews the subject via a telecommunications ling to determine if a medical emergency exists 2 and whether or not to activate EMS. The telemedical care provider subsequently utilizes remote biosensors to collect biometric health data 3, which is integrated into a personalized risk assessment for the subject in order to facilitate diagnosis and prescription of a medication. Further in this embodiment, the telemedical care provider transmits an authorization for a short-term supply of a medication for the subject to a pharmacist 4. The pharmacist in turn activates an apparatus for remotely dispensing the medication to the subject 5. The telemedical care provider follows-up by issuing a prescription for a long-term supply of medication 6, which is filled by one of several traditional routes.

The inventions disclosed herein include business methods. In some embodiments, the devices, systems, software, and methods disclosed herein are marketed, advertised, and sold as, for example, products and services for providing remote medical diagnosis and therapy to a subject. The products and services disclosed herein are particularly well suited for providing low cost healthcare alternatives the uninsured, the underinsured, those in remote and rural areas, and those in developing countries. The products and services disclosed herein are also well suited for supplementation of existing healthcare systems in outpatient, urgent care, or acute situations. The products and services disclosed herein are also well suited for supplementation of existing healthcare systems in emergency, disaster, or combat situations.

In some embodiments, the devices, systems, and software are employed, in part or in whole, in healthcare facilities such as hospitals, hospice, nursing homes, urgent care offices, diagnostic laboratories, and the like. In some embodiments, the devices, systems, and software are employed, in part or in whole, in veterinary facilities such as animal hospitals, veterinary offices, and the like. In some embodiments, the devices, systems, and software are employed, in part or in whole, in a subject's home. In some embodiments, the devices, systems, and software are employed, in part or in whole, in retail businesses such as boutiques, clinics, pharmacies, drug stores, or supermarkets. In some embodiments, the devices, systems, and software are mobile and employed, in part or in whole, in vehicles used by, for example, EMS personnel (e.g., EMTs and paramedics), police, fire fighters, first responders, FEMA personnel, military personnel, etc. In some embodiments, the devices, systems, and software are mobile and elements are carried or worn by, for example, EMS personnel (e.g., EMTs and paramedics), police, fire fighters, first responders, FEMA personnel, military personnel, etc.

In some embodiments, the devices, software, systems, and methods are further utilized to provide remote telemedical services. These services would, for example, improve the productivity of clinicians, relieve overburdened healthcare systems, and create healthcare alternatives for the uninsured, the underinsured, and those in remote areas and developing countries with limited access to telemedical, outpatient, acute care, urgent care, and insurance services.

In some embodiments, the devices, software, systems, and methods are further utilized to provide remote medical risk assessment and diagnostic services. These services would, for example, relieve overburdened healthcare systems in outpatient, acute care, and urgent care situations.

In some embodiments, the devices, software, systems, and methods are further utilized to provide remote insurance services providing, for example, instantaneous encounter-specific coverage including a level of guarantee and an associated premium.

In some embodiments, the devices, software, systems, and methods are utilized by contract research organizations (CROs), service organizations that provide support to the pharmaceutical and biotechnology industries in the form of research services outsourced on a contract basis. In further embodiments, the devices, software, systems, and methods are utilized to improve efficiency, reduce error, and improve the integrity of study data collected by a CRO. In further embodiments, the devices, software, systems, and methods are utilized by a CRO to facilitate the process of recruiting subjects for a research study. For example, in many cases CROs search for a very specific cohort of individuals who meet the inclusion criteria for a particular study. Many of these individuals may be remotely located and coming into a research center for the study would create an imposition for both the CRO and the individual. In such embodiments, remote technology such as that described herein improves the process for the CRO and the individual.

In some embodiments, the devices, software, systems, and methods are utilized in transitional care. In many cases, inadequate care coordination, including poor care transitions, result in wasteful spending and unnecessary hospital readmissions. When discharged from a hospital, patients often receive little information on how to care for themselves, when to resume activities, what medication side effects to look out for, and how to get answers to questions. Current and pending legislation creates powerful incentives for improving discharge methods and improving the quality of transitional care. In further embodiments, the devices, software, systems, and methods are utilized to provide follow up consultations with patients to ensure they understand post-care procedures, medication regimens, and for on-going analysis of the risk of readmission.

Subjects

In some embodiments, the systems, devices, software, and methods disclosed herein provide remote medical diagnosis and therapy to a subject. In further embodiments, a module for telecommunications provides communications between one or more healthcare providers and a subject. In further embodiments, at least one remotely controlled biosensor is used to examine a subject. In further embodiments, a software module applies a diagnostic or therapeutic analysis for a subject. In still further embodiments, diagnostic or therapeutic analysis involves accessing health and economic records for a subject. In further embodiments, an apparatus dispenses one or more medical items to a subject. In further embodiments, a software module provides instantaneous encounter-specific financial insurance coverage with a level of guarantee and an associated premium to a subject.

In some embodiments, the subject is a human medical patient. In further embodiments, the subject is a human, pediatric medical patient. In other embodiments, the subject is a human, adult or geriatric medical patient. In some embodiments, a human medical patient has one or more insurance policies for medical care. In further embodiments, an insurance policy covers the events or conditions leading a subject to interact with the systems and devices described herein. In further embodiments, a human medical patient is under the care of a physician. In some embodiments, a human medical patient does not have an insurance policy for medical care. In further embodiments, no insurance policy covers the events or conditions leading a subject to interact with the systems and devices described herein. In further embodiments, a human medical patient is not under the care of a physician.

In some embodiments, the subject is a non-human animal veterinary patient. In further embodiments, a non-human animal subject is under the care of an owner, caretaker, rescuer, or veterinarian. In still further embodiments, a non-human animal subject includes, by way of non-limiting example, those attended to by exotic animal veterinarians, large animal veterinarians, domestic animal veterinarians, wildlife veterinarians, laboratory animal veterinarians, food animal veterinarians, and equine veterinarians. In still further embodiments, a non-human animal subject includes, by way of non-limiting example, those classified as invertebrates, fish, amphibians, reptiles, birds, and mammals.

In some embodiments, the systems, devices, and software disclosed herein include hardware and software modules for identifying a subject and/or determining or verifying the insurance coverage of a subject. In further embodiments, a subject enters identifying information via an input device (e.g., keyboard, keypad, touch screen, multi-touch screen, pointing device, microphone, video camera, etc.) associated with the systems and devices disclosed herein. In further embodiments, a subject presents a physical object such as an insurance card, credit card, driver's license, etc. In still further embodiments, a subject presents their person as a source of identifying information. In some embodiments, a module for identifying a subject utilizes personal information including, by way of non-limiting example, name, address, employer, date of birth, age, and the like. In some embodiments, a module for identifying a subject utilizes health insurance information including, by way of non-limiting example, payer, primary care physician, policy number, group number, name of insured, and the like. In some embodiments, a module for identifying a subject utilizes credit card information including, by way of non-limiting example, card issuer, primary account holder, name on card, billing name, billing address, account number, and the like. In some embodiments, a module for identifying a subject utilizes driver's license information including, by way of non-limiting example, name, license number, state of issuance, expiration date, and the like. In some embodiments, a module for identifying a subject utilizes biometric information including, by way of non-limiting example, retinal information, iris information, fingerprint information, palm print information, facial geometry information, voice information, and combinations thereof. In further embodiments, the module for identifying the subject utilizes at least one remotely controlled biosensor to obtain biometric information.

Healthcare Providers

In some embodiments, the systems, devices, software, and methods described herein utilize the services of a healthcare provider. In some embodiments, a healthcare provider is live. As used herein, the term "live" describes a human healthcare provider, as opposed to an artificial intelligence or a software algorithm, who interacts with the systems, devices, software, and/or subject described herein asynchronously, substantially synchronously, or synchronously (e.g., in real-time).

In some embodiments, a healthcare provider is remote. As used herein, the term "remote" describes a healthcare provider who is not present with a subject at the time healthcare services are rendered using the inventions described herein. In some embodiments, a remote healthcare provider is outside of the facility, city, county, state, or country of the subject at the time healthcare services are rendered using the inventions described herein.

In some embodiments, a healthcare provider is an adjunct provider. The term "adjunct" describes a healthcare provider who is credentialed by a licensed primary healthcare provider facility, group, or individual to provide remote care for one or more patients who are legally under the care of the primary provider.

In some embodiments, the methods, systems, and software described herein utilize the services of one or more telemedical care providers. In some embodiments, telemedicology refers to a branch of medicine or surgery requiring specialized, formal, peer-reviewed training as a specialty or subspecialty of medicine concerned with safely and efficaciously providing remote diagnosis and therapy via telemedicine technology and equipment. In some embodiments, formal training in telemedicology requires completion of a fellowship in telemedicology. In further embodiments, a telemedicologist is a physician, surgeon, dentist and/or veterinarian specialized in telemedicology and providing remote diagnosis and therapy via telemedicine technology and equipment. In still further embodiments, a telemedical care provider (TCP) is a healthcare worker trained and engaged in provision of remote diagnosis and therapy via telemedicine technology and equipment. In some embodiments, a TCP is, for example, a telemedicologist. In further embodiments, a TCP is a telemedicologist (e.g., physician, surgeon, dentist, veterinarian, or other licensed professional) who, following a residency and/or fellowship in their field, is board certified for example by the American board of surgery, medicine, pediatrics in primary care and or in a subspecialty such as cardiology, etc. In still further embodiments, a TCP is a telemedicologist (e.g., physician, surgeon, dentist, veterinarian, or other licensed professional) who is a certified by a recognized body providing a peer reviewed telemedicology education program. In some embodiments, a TCP is, for example, a licensed physician extender (e.g., nurse practitioner, physician assistant, registered nurse, pharmacist, licensed vocational nurse, emergency medical technician, etc.) directly supervised by or reporting to a telemedicologist in activity related to the provision of remote diagnosis and therapy via telemedicine technology and equipment. In some embodiments, a telemedicalist is a physician specialized in the delivery of telemedical care to acutely ill hospitalized subjects.

In some embodiments, a telemedical care provider is a doctorate level health care provider. In further embodiments, a telemedical care provider is a physician, dentist, or veterinarian telemedicologist. In other embodiments, a telemedical care provider is a non-physician. In further embodiments, a telemedical care provider is, by way of non-limiting examples, a pharmacist, a dentist, a physician assistant, a nurse practitioner, a registered nurse, a pharmacist, a chiropractor, an emergency medical technician, a licensed practical nurse, a certified ultrasound technician, a psychologist, a social worker, a military medic, a physical therapist, an occupational therapist, a speech therapist, a radiology technician, a cardiac catheterization technician, a clinical pathology laboratory technician, a medical aesthetician, a licensed medical technologist, a toxicologist consultant, a credentialed medical legal consultant, and a credentialed hospital operations administrator. In some embodiments, a telemedical care provider is a veterinarian or a veterinary nurse, assistant, or technician.

In some embodiments, the systems, devices, software, and methods described herein utilize the services of a plurality of healthcare providers. In further embodiments, a plurality of healthcare providers includes 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500 or more providers, including increments therein. In some embodiments, the systems, devices, software, and methods described herein utilize the services of at least 2, 3, 4, 5, 6, 7, 8, 9, 10, 11, 12, 13, 14, 15, 16, 17, 18, 19, 20 or more healthcare providers. In further embodiments, a plurality of healthcare providers use the systems simultaneously. In still further embodiments, a healthcare provider is identified or selected for a particular case or contact based on parameters including, by way of non-limiting examples, a patient's condition, disease, or injury, severity of a patient's condition, disease, or injury, a patient's insurance eligibility, or availability.

In some embodiments, the systems, devices, software, and methods described herein include hardware and a software module to verify a healthcare provider's identity. In further embodiments, a provider enters identifying information via an input device (e.g., keyboard, keypad, touch screen, multi-touch screen, pointing device, microphone, video camera, etc.) associated with the systems and devices disclosed herein. In further embodiments, a provider presents a physical object such as a driver's license, credit card, professional association card, etc. In still further embodiments, a provider presents their person as a source of identifying information. In some embodiments, a module for identifying a provider utilizes information including, by way of non-limiting example, personal information, medical license information, malpractice insurance information, credit card information, driver's license information, and biometric information. In some embodiments, the systems, products, programs, and methods described herein include hardware and a software module to biometrically verify a provider's identity. In further embodiments, the biometric hardware and software is adapted to recognize physiological characteristics including, by way of non-limiting examples, retinal information, iris information, fingerprint information, palm print information, facial geometry information, voice information, and combinations thereof.

In some embodiments, a healthcare provider operates one or more of the medical devices, apparatus, and/or software modules of the systems and devices described herein. In further embodiments, a healthcare provider operates, by way of non-limiting examples, a biosensor, an apparatus for dispensing one or more medical items, hardware and software for telecommunications, software for applying a diagnostic or therapeutic analysis, software for providing access to one or more electronic health records for a subject, software for identifying a subject, and software for providing instantaneous encounter-specific financial insurance coverage. In other embodiments, a healthcare provider assists in the operation of one or more of the medical devices and/or software modules described herein. In yet other embodiments, a healthcare provider supervises or oversees operation of one or more of the medical devices and/or software modules described herein.

In some embodiments, the systems, devices, software, and methods described herein do not utilize the services of a live healthcare provider. For example, in some embodiments, the systems and devices described herein include a non-communication mode, described further herein. In further embodiments, the systems and devices described herein operate in a non-communication mode when communication protocols fail, when communication channels or signals fail or are lost, or when devices are placed in a location where one or more communication protocols, channels, or signals are unavailable. In a non-communication mode, a live, remote healthcare provider is unable to monitor, supervise, or operate components of a device. By way of further example, in some embodiments, the systems and devices described herein include an emergency mode, described further herein. In an emergency mode, in some embodiments, components of a system or device act autonomously, without monitoring, supervision, or operation by a live, remote healthcare provider.

Credentialing

In some embodiments, a live healthcare provider is licensed, for example, by one or more U.S. state medical boards, a branch of the U.S. Federal Government (e.g., the Veteran's Administration, Department of Health and Human Services, and the Department of Defense, etc.) or a foreign national government. In some embodiments, a live healthcare provider is insured for professional malpractice.

In some embodiments, a subject is under the care of a primary care provider. In further embodiments, a live healthcare provider is credentialed by a subject's primary care provider. In still further embodiments, a live healthcare provider is credentialed by a subject's primary care provider to provide, for example, remote diagnosis and therapy, telemedical services, urgent care services, outpatient services, acute care services, pharmacy services, or insurance services to the subject.

In other embodiments, a subject is under the care of a live healthcare provider described herein. In further embodiments, a live healthcare provider provides, for example, remote diagnosis and therapy, telemedical services, urgent care services, outpatient services, acute care services, pharmacy services, or insurance services to a subject. In appropriate circumstances, a live healthcare provider refers a subject to another healthcare provider. In appropriate circumstances, a live healthcare provider triages a subject to a higher level of care (e.g., inpatient care, emergency response system, etc.). In appropriate circumstances, a live healthcare provider triages a subject to a lower level of care (e.g., self-care, bed rest, oral hydration, etc.).

The systems, devices, software, and methods described herein include, in various embodiments, a software module for verifying the identity and/or credentials of a healthcare provider. In some embodiments, the software module creates, stores, and retrieves healthcare provider identity and credential records. In some embodiments, the software module verifies a credential issued by a licensed primary healthcare provider facility, group, or individual. In further embodiments, the primary healthcare provider facility, group, or individual is licensed, for example, by one or more U.S. state medical boards, a branch of the U.S. Federal Government (e.g., the Veteran's Administration, Department of Health and Human Services, and the Department of Defense, etc.) or a foreign national government. In further embodiments, a credential issued for a live, remote, adjunct healthcare provider to provide remote adjunct care for one or more patients legally under the care of said licensed primary healthcare provider facility, group, or individual. In some embodiments, a patient is admitted to the healthcare facility. In other embodiments, a patient is not admitted to the healthcare facility. In further embodiments, a patient is receiving care as an outpatient or emergency department patient at the healthcare facility.

In some embodiments, the software module verifies a credential issued by a licensed primary healthcare provider facility, group, or individual that indicates the remote adjunct healthcare provider successfully completed a medical and legal screening process. In further embodiments, a screening process includes verification of, by way of non-limiting examples, prescription license, education, training, certifications, professional references, malpractice insurance coverage, malpractice insurance state, malpractice insurance coverage limits, legal license to practice their profession, and state of licensure. In still further embodiments, a screening process includes one or more live interviews of a remote adjunct healthcare provider by a licensed primary healthcare provider facility, group, or individual.

In some embodiments, the software module verifies a credential that indicates a licensed primary healthcare provider facility, group, or individual has granted admitting privileges to a remote adjunct healthcare provider. In further embodiments, admitting privileges include billing privileges. In some embodiments, admitting privileges include the right to admit patients to a facility for a specific diagnostic or therapeutic service. In some embodiments, admitting privileges include the right to admit patients to a facility for a consultative service. In some embodiments, admitting privileges are granted to a non-physician to treat patients independently with the appropriate state's required oversight and review of the healthcare protocols used by a legally licensed, credentialed physician to empower the non-physician to execute healthcare.

Medical Devices

In some embodiments, the systems for providing remote medical diagnosis and therapy to a subject include one or more medical devices that include at least one processor, at least one memory device, and an operating system configured to perform executable instructions. In further embodiments, a medical device includes one or more biosensors. In still further embodiments, the biosensors are remotely controlled. In further embodiments, a medical device includes a software module for establishing, maintaining, and conducting telecommunications. In further embodiments, a medical device includes a software module for applying a diagnostic or therapeutic analysis. In further embodiments, a medical device includes an apparatus for dispensing one or more medical items from an inventory of medical items to a subject. In still further embodiments, a medical device includes a software module for providing financial insurance coverage to a subject. In still further embodiments, a medical device includes a software module for providing instantaneous encounter-specific financial insurance coverage with a level of guarantee and an associated premium to a subject.

The devices described herein are characterized by scalability. In various embodiments, the devices described herein have a wide range of suitable scales and sizes. Those of skill in the art will recognize that the most suitable scale for a particular application varies with, for example, the need for portability, tolerance of expense, the number and type features desired, the volume of subjects served, and the like. While the scale and size of the devices described herein is represented by a continuum, three non-limiting, representative scales are described further.

Figure 2:
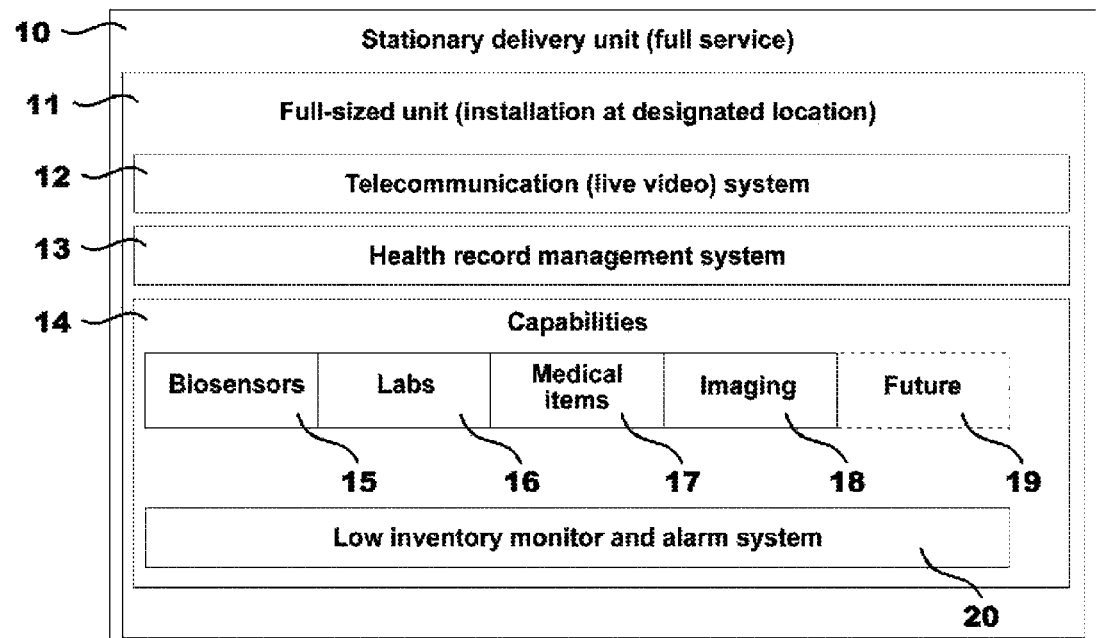
FIG. 2 shows a non-limiting block diagram of a stationary embodiment of a device for providing remote medical diagnosis and therapy to a subject; in this case, a device including a full-sized unit suitable for installation at a facility, a telecommunications system, a health record management system, and an array of diagnostic capabilities.

Referring to FIG. 2, in a particular stationary embodiment 10, the medical device is a full-sized unit 11 suitable for installation at a healthcare facility such as a hospital, urgent care clinic, diagnostic laboratory, and the like. In a further particular embodiment, a telecommunications system 12 provides live audio and video communication between a subject or other user of the device and a live, remote healthcare provider. Further, in this particular embodiment, the device includes a health record management system 13, which allows a live, remote healthcare provider to access, review, and edit health records for a subject from a variety of electronic sources. The particular embodiment includes an array of diagnostic and therapeutic capabilities 14. In still further embodiments, the diagnostic capabilities include, by way of non-limiting examples, biosensors 15 remotely controlled by a live, remote healthcare provider, body fluid culture and analysis 16, an inventory of medical items for dispensing to a subject or an appropriate provider or caregiver 17, medical imaging 18, and ports for future hardware and software expansion 19. Each of the diagnostic capability modules is monitored by a software module that issues an alarm 20 when medical items, supplies, reagents, and the like are low and need refilling.

Figure 3:
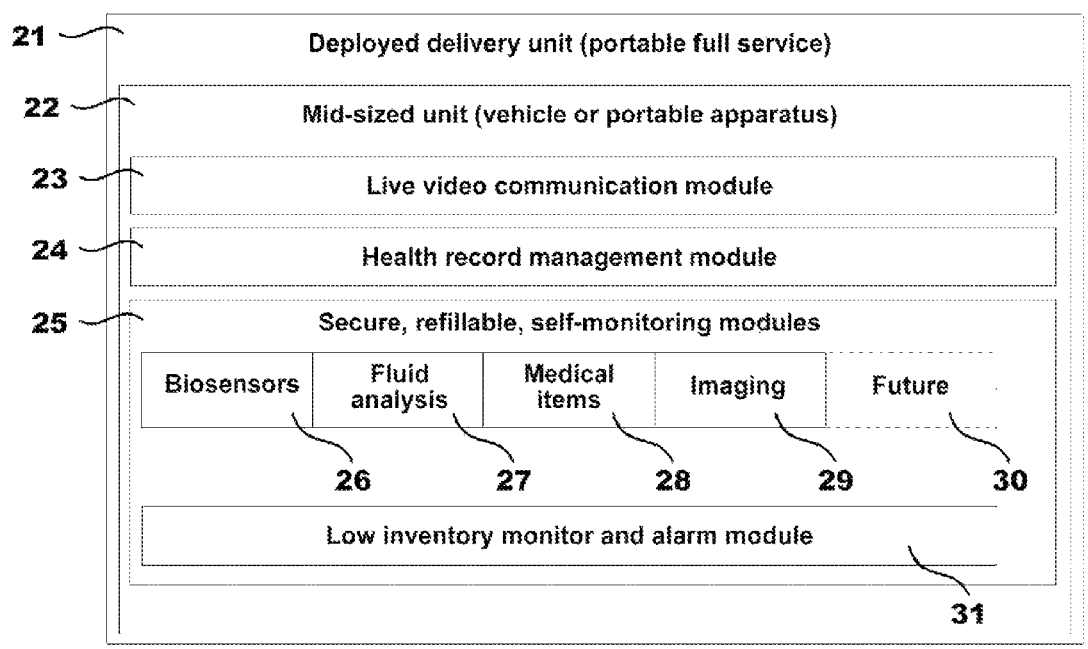
FIG. 3 shows a non-limiting block diagram of a deployed embodiment of a device for providing remote medical diagnosis and therapy to a subject; in this case, a device including a mid-sized unit suitable for mounting in a vehicle, a telecommunications module, a health record management module, and an array of diagnostic modules.

Referring to FIG. 3, in another particular portable embodiment 21, the medical device is a mid-sized unit 22 suitable for portable installation in a vehicle such as an ambulance, fire truck, military vehicle, and the like. In a further particular embodiment, a telecommunications system 23 provides live audio and video communication between a subject or other user of the device and a live, remote healthcare provider. Further, in this particular embodiment, the device includes a health record management system 24, which allows a live, remote healthcare provider to access, review, and edit health records for a subject from a variety of electronic sources. The particular embodiment includes an array of diagnostic and therapeutic modules 25 designed for quick refill and resupply. In still further embodiments, the diagnostic modules include, by way of non-limiting examples, biosensors 26 remotely controlled by a live, remote healthcare provider, body fluid culture and analysis 27, an inventory of medical items for dispensing to a subject or an appropriate provider or caregiver 28, medical imaging 29, and ports for future module expansion 30. Each of the diagnostic and therapeutic modules is monitored by a software module that issues an alarm 31 when medical items, supplies, reagents, and the like are low and need refilling.

Figure 4:
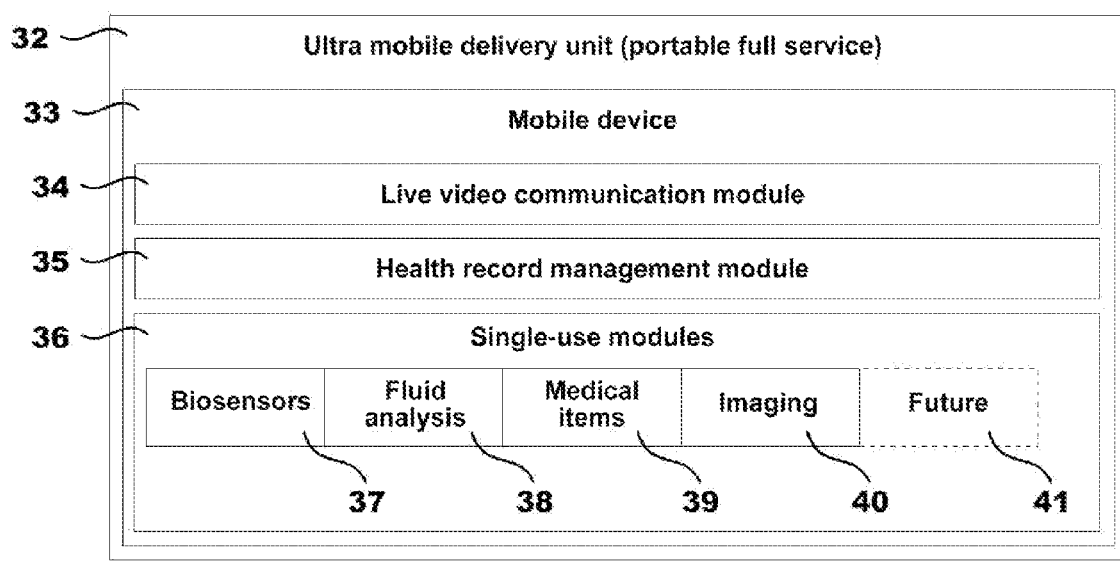
FIG. 4 shows a non-limiting block diagram of a mobile embodiment of a device for providing remote medical diagnosis and therapy to a subject; in this case, a device including a mobile computing device, a telecommunications module, a health record management module, and an array of single-use diagnostic modules.

Referring to FIG. 4, in another particular ultra-mobile embodiment 32, the medical device is a mobile computing device 33 suitable for carrying or wearing by first responders, military medics, and the like. In a further particular embodiment, a telecommunications module 34 provides live audio and video communication between a subject or other user of the device and a live, remote healthcare provider. Further, in this particular embodiment, the device includes a health record management system 35, which allows a live, remote healthcare provider to access, review, and edit health records for a subject from a variety of electronic sources. The particular embodiment includes an array of single use diagnostic and therapeutic modules 36. In still further embodiments, the diagnostic modules include, by way of non-limiting examples, biosensors 37 remotely controlled by a live, remote healthcare provider, body fluid culture and analysis 38, an inventory of medical items for dispensing to a subject or an appropriate provider or caregiver 39, medical imaging 40, and ports for future module expansion 41.

In some embodiments, the medical device is a digital processing device and includes one or more hardware central processing units (CPU) that carry out the device's functions. In further embodiments, the device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the devices described herein include user interfaces. In further embodiments, the user interfaces include graphic user interfaces (GUIs). In still further embodiments, the user interfaces are interactive and present a user with menus and options for interacting with the systems and devices described herein. In further embodiments, the device includes a display screen to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein. In still further embodiments, the device includes an input device to receive information from a user. In some embodiments, the input device is a keyboard. In further embodiments, the input device is a key pad. In a particular embodiment, the input device is a simplified key pad for use by a subject with communications limitations (e.g., due to age, infirmity, disability, etc.), wherein each key is associated with a color, a shape, and health/communication concept. See e.g., FIG. 28. In some embodiments, the input device is a pointing device including, by way of non-limiting examples, a mouse, trackball, track pad, joystick, game controller, or stylus. In some embodiments, the input device is the display screen, which is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein. In some embodiments, the input hardware and software is adapted to accommodate subjects, caregivers, healthcare providers, and other users with mental and physical disabilities.

In accordance with the description herein, suitable devices include (or are based on), by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, and video game consoles. Those of skill in the art will recognize that many smartphones are suitable for use in the system described herein. Those of skill in the art will also recognize that select televisions and select digital music players with computer network connectivity are suitable for use in the system described herein. Suitable tablet computers include those with booklet, slate, and convertible configurations, known to those of skill in the art.

In some embodiments, one or more components of a medical device are reversibly separable. For example, in a particular embodiment, one or more biosensors are reversibly separable from a device to increase portability and facilitate access to subjects who may be immobile or isolated. In another particular embodiment, the telecommunications component is reversibly separable from the device to increase portability and facilitate communication with subjects who may be immobile or isolated. In another particular embodiment, the device is reversibly separable from the apparatus for dispensing medical items, again to increase portability, in cases where the dispensing apparatus is large, heavy, bulky, or fixed to a particular location. In other embodiments, the components are not separable.

Figure 12:
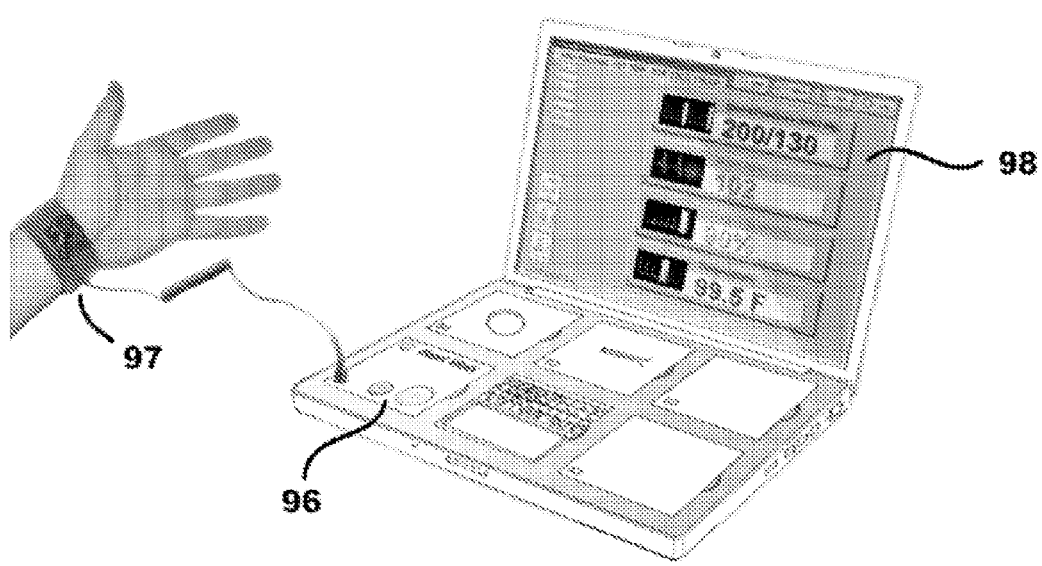
FIG. 12 shows a non-limiting example of a networked medical device including a biosensor; in this case, a portable medical device including a wrist cuff for monitoring vital signs.

Referring to FIG. 12, in a particular embodiment, a medical device is a portable computing device including six diagnostic modules. The diagnostic modules are removable and interchangeable such that the device is optionally configured for a wide range of environments, end users, and/or patient populations by selecting and installing particular diagnostic modules. In this embodiment, a heart vital sign diagnostic module 96 interacts with a wrist cuff biosensor 97 to obtain patient diagnostic information 98, which is displayed on a flip-up touchscreen. Further in this embodiment, heart vital sign diagnostic information includes blood pressure, heart rate, oxygen saturation, and body temperature.

Figure 13:
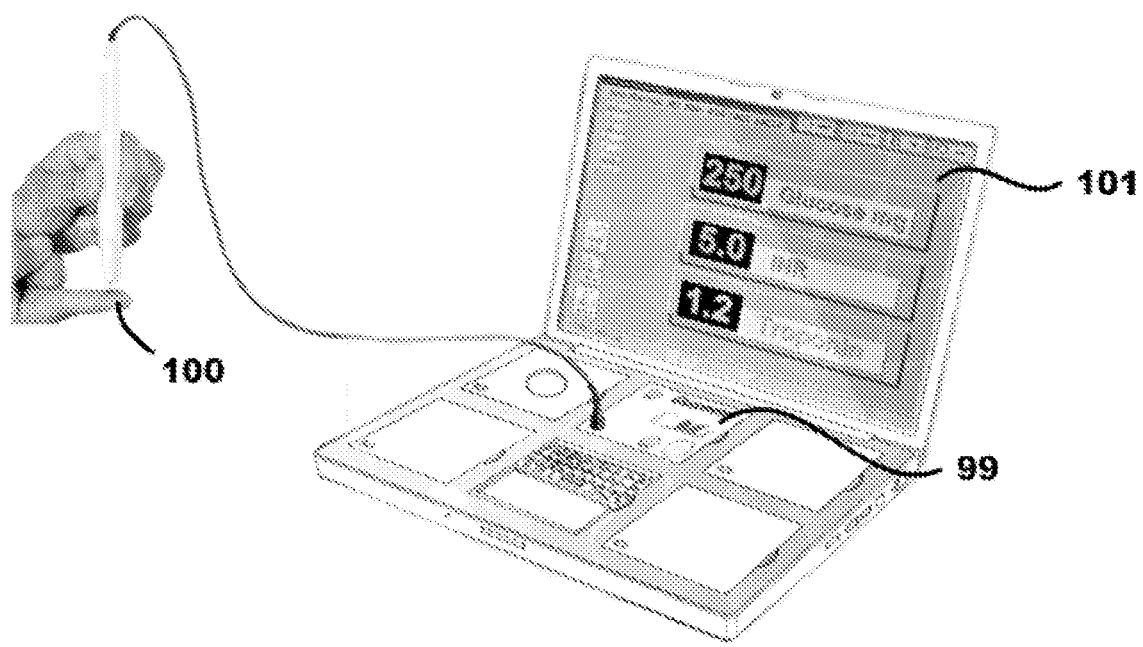
FIG. 13 shows a non-limiting example of a networked medical device including a biosensor; in this case, a portable medical device including a blood analyzer for measuring blood biochemical parameters.

Referring to FIG. 13, in a particular embodiment, a medical device is a portable computing device including six diagnostic modules. The diagnostic modules are removable and interchangeable such that the device is optionally configured for a wide range of environments, end users, and/or patient populations by selecting and installing particular diagnostic modules. In this embodiment, a blood chemistry/biomarker diagnostic module 99 interacts with a blood chemistry/biomarker biosensor 100 to obtain patient diagnostic information 101 from a drop of blood, which is displayed on a flip-up touchscreen. Further in this embodiment, chemistry/biomarker diagnostic information includes blood glucose, International Normalized Ratio (INR), and troponin.

Figure 14:
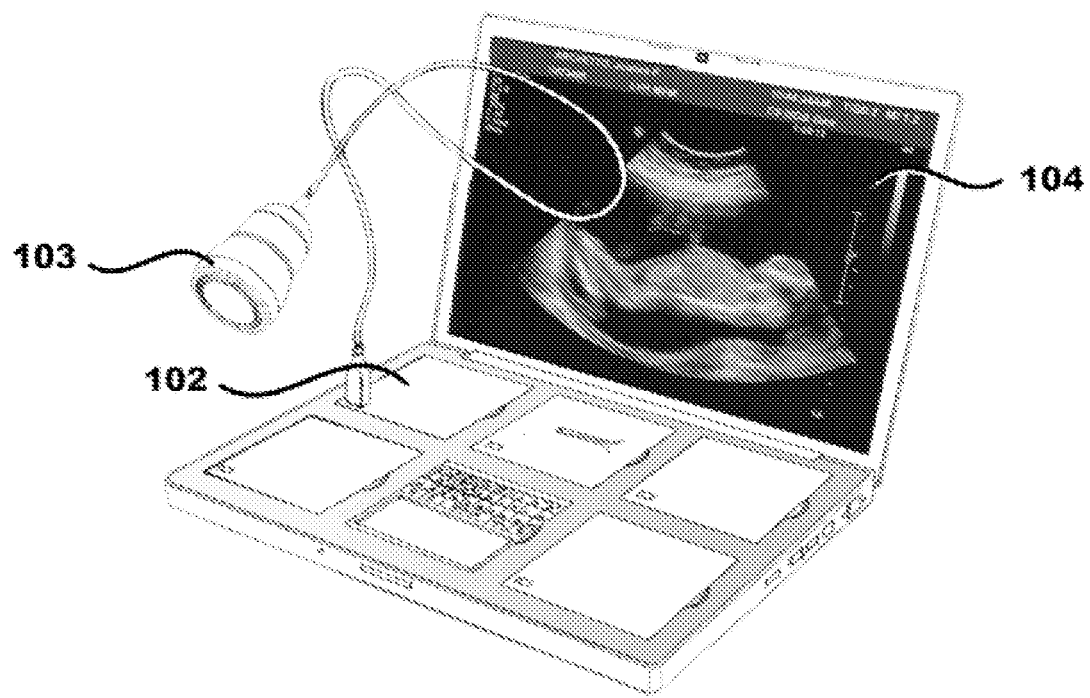
FIG. 14 shows a non-limiting example of a networked medical device including a biosensor; in this case, a portable medical device including a fetal ultrasound device.

Referring to FIG. 14, in a particular embodiment, a medical device is a portable computing device including six diagnostic modules. The diagnostic modules are removable and interchangeable such that the device is optionally configured for a wide range of environments, end users, and/or patient populations by selecting and installing particular diagnostic modules. In this embodiment, an ultrasound diagnostic module 102 interacts with a fetal ultrasound probe 103 to obtain patient diagnostic information 104, which is displayed on a flip-up touchscreen.

Figure 15:
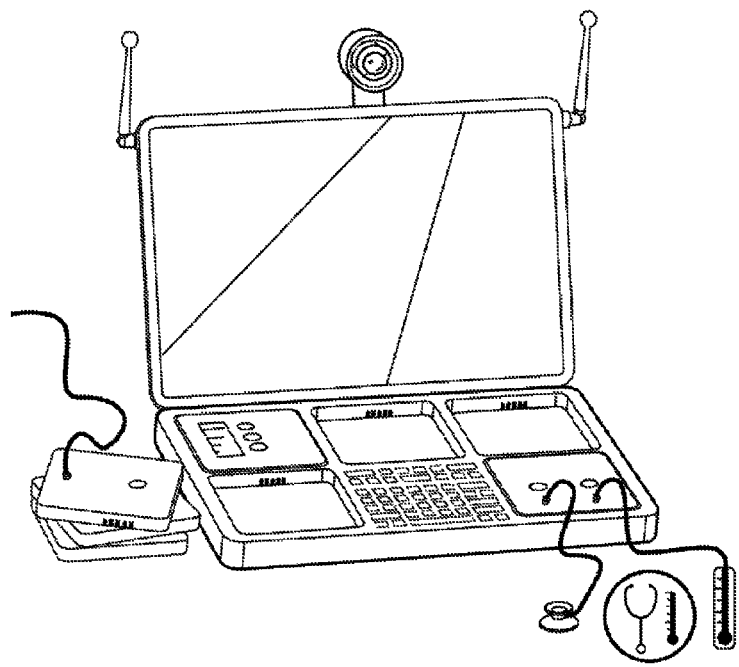
FIG. 15 shows a non-limiting example of a networked medical device including biosensors; in this case, a medical device including a plurality of removable biosensor modules that physically dock into a portable base station.

Referring to FIG. 15, in a particular embodiment, a system for providing remote medical diagnosis and therapy to a subject includes a computer-based device based on a laptop clamshell configuration. In this embodiment, the device includes five ports for physically docking removable diagnostic modules into customizable configurations. In many embodiments, diagnostic modules are optionally configured based on the health and economic risks faced by a particular subject, family, or population. Further in this embodiment, the device includes a high-definition digital video camera and a telecommunications element to allow interaction with a telemedical care provider.

Figure 16:
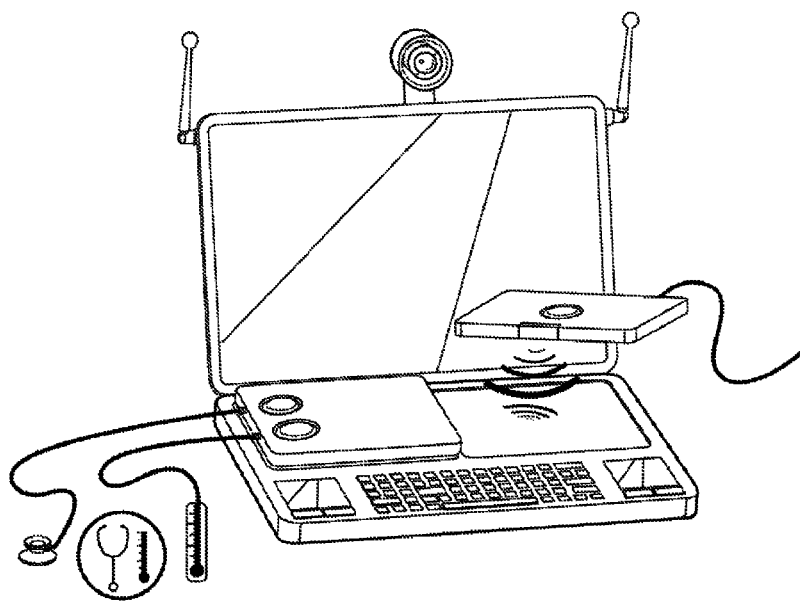
FIG. 16 shows a non-limiting example of a networked medical device including biosensors; in this case, a medical device including a plurality of biosensor modules that communicate wirelessly with a portable base station.

Referring to FIG. 16, in a particular embodiment, a system for providing remote medical diagnosis and therapy to a subject includes a computer-based device based on a laptop clamshell configuration. In this embodiment, the device includes two ports for wirelessly docking removable diagnostic modules into customizable configurations. In many embodiments, wirelessly connected diagnostic modules increase portability and facilitate access to subjects. Further in this embodiment, the device includes a high-definition digital video camera and a telecommunications element to allow interaction with a telemedical care provider.

Figure 17:
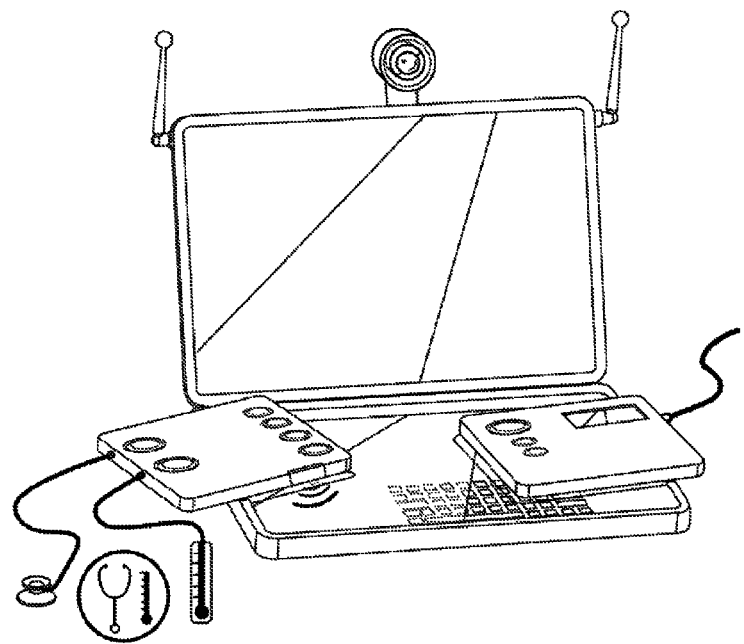
FIG. 17 shows a non-limiting example of a networked medical device including biosensors; in this case, a medical device including a plurality of biosensor modules that communicate via a Near Field Communication (NFC) protocol (e.g., Bluetooth, Zigbee, etc.) with a portable base station.

Referring to FIG. 17, in a particular embodiment, a system for providing remote medical diagnosis and therapy to a subject includes a computer-based device based on a laptop clamshell configuration. In this embodiment, the device includes portable diagnostic modules in communication with the device via a NFC protocol. In many embodiments, NFC connected diagnostic modules allow rapid configuration and re-configuration based on health and economic risks faced by a particular subject, family, or population. Further in this embodiment, the device includes a high-definition digital video camera and a telecommunications element to allow interaction with a telemedical care provider.

Referring to FIGS. 12-17, in particular embodiments, a medical device includes a touch screen for user input. In further embodiments, a medical device includes a keyboard or a condensed keyboard for user input. In further embodiments, a medical device includes a digital video camera (or stereo cameras for 3D imaging), a microphone, and speakers, all of which are optionally used in collecting patient diagnostic information and also optionally used for communication via audio conference, video conference, or web meeting. In further particular embodiments, a medical device includes an input/output port (e.g., USB, etc.) optionally allowing end users to store patient data such as test results. In further particular embodiments, a medical device is optionally connected to a printer to print out reports including patient data (e.g., test results).

In some embodiments, one or more components of a medical device are non-portable or fixed in a stationary installation. For example, in a particular embodiment, one or more biosensors are fixed in a stationary installation to increase access to subjects at a centralized location. In another particular embodiment, the telecommunications component is fixed in a stationary installation to increase access to subjects at a centralized location. In another particular embodiment, an apparatus for dispensing medical items is fixed in a stationary installation to increase access to subjects at a centralized location.

Figure 18:
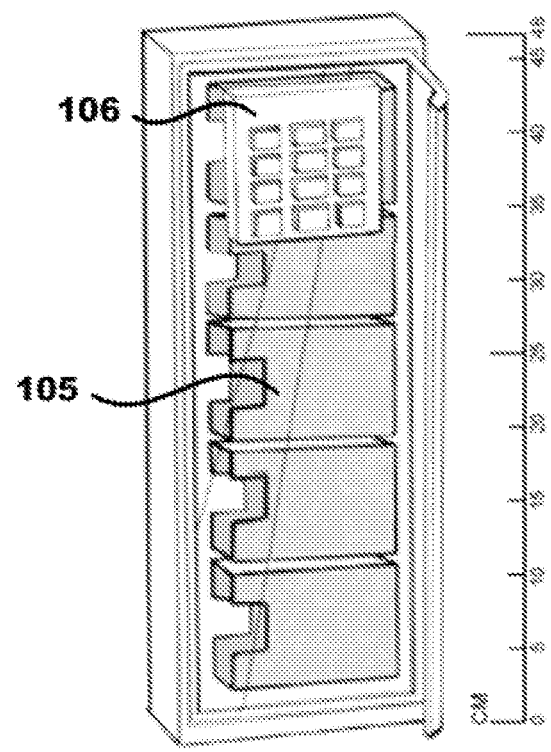
FIG. 18 shows a non-limiting example of an apparatus for dispensing one or more medical items from an inventory of medical items to a subject; in this case, a portable apparatus with a volume of 1 L.

Referring to FIG. 18, in a particular embodiment, an apparatus for dispensing medical items to a subject is a standalone portable device with a capacity of 1 L designed for individual use. In this embodiment, an apparatus for dispensing medical items includes five doors 105, each opened remotely by a healthcare provider (e.g., pharmacist, nurse, physician, etc.). Further in this embodiment, each door is associated with a separate compartment for a particular medical item. Where a medical item is a medication, it is dispensed in a standardized unit pack labeled with drug name, dosage, expiration date, lot number, and the like. In this embodiment, an apparatus for dispensing medical items also includes a keypad 106 for operating the apparatus and/or communicating with a healthcare professional.

Figure 19:
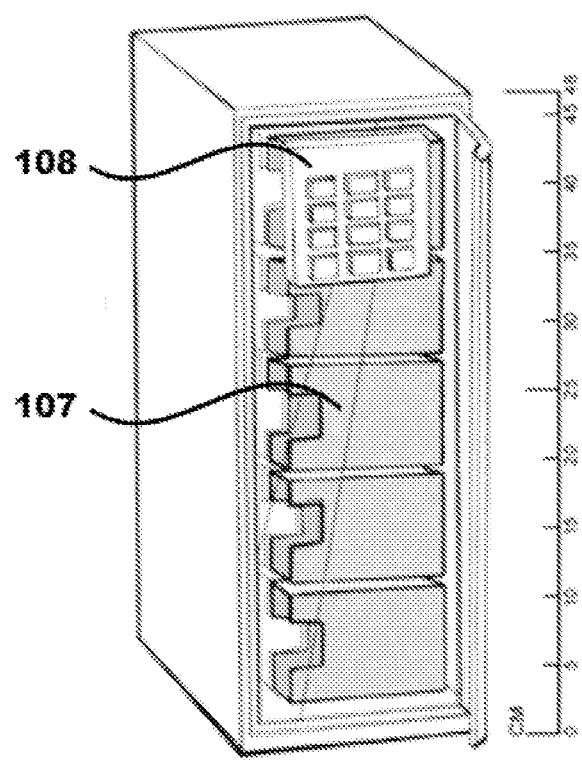
FIG. 19 shows a non-limiting example of an apparatus for dispensing one or more medical items from an inventory of medical items to a subject; in this case, a portable apparatus with a volume of 5 L.

Referring to FIG. 19, in a particular embodiment, an apparatus for dispensing medical items to a subject is a standalone portable device with a capacity of 5 L designed for family use. In this embodiment, an apparatus for dispensing medical items includes five doors 107, each opened remotely by a healthcare provider (e.g., pharmacist, nurse, physician, etc.). Further in this embodiment, each door is associated with a separate compartment for a particular medical item. Where a medical item is a medication, it is dispensed in a standardized unit pack labeled with drug name, dosage, expiration date, lot number, and the like. In this embodiment, an apparatus for dispensing medical items also includes a keypad 108 for operating the apparatus and/or communicating with a healthcare professional.

Figure 20:
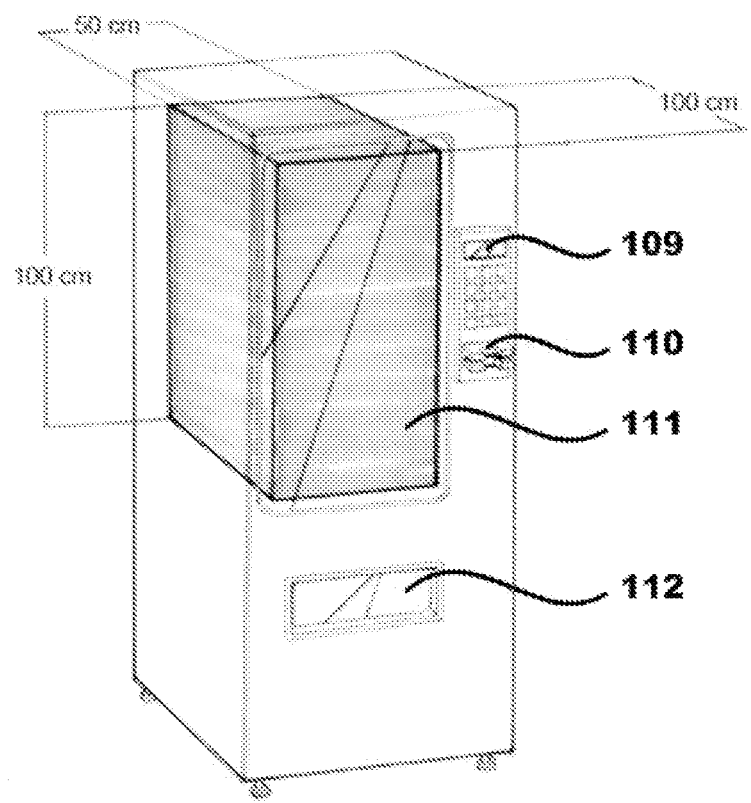
FIG. 20 shows a non-limiting example of an apparatus for dispensing one or more medical items from an inventory of medical items to a subject; in this case, a stationary apparatus with a volume of 50 L.

Referring to FIG. 20, in a particular embodiment, an apparatus for dispensing medical items to a subject is a standalone stationary device with a capacity of 50 L designed for commercial, retail, or healthcare facility use. In this embodiment, an apparatus for dispensing medical items includes a keypad for user input 109 and a payment interface 110 allowing a user to optionally identify a subject, enter medical item information, and/or pay for dispensed items. Further in this embodiment, medical items are dispensed from a removable inventory container 111 from a dispensing door 112. Where a medical item is a medication, it is dispensed in a standardized unit pack labeled with drug name, dosage, expiration date, lot number, and the like.

Figure 21:
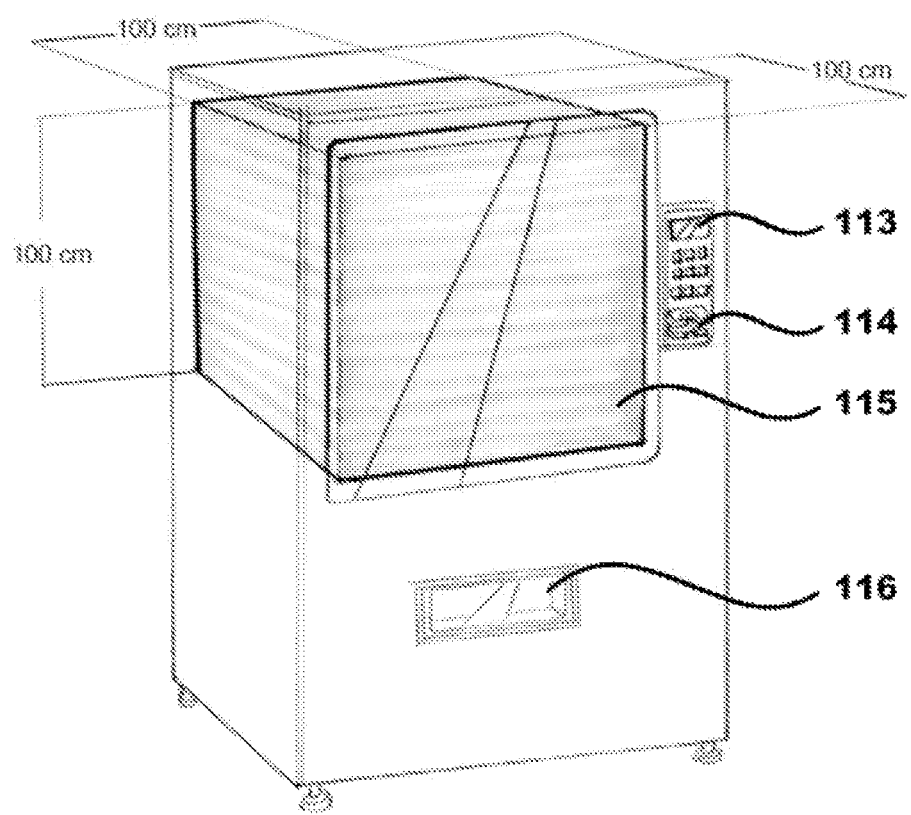
FIG. 21 shows a non-limiting example of an apparatus for dispensing one or more medical items from an inventory of medical items to a subject; in this case, a stationary apparatus with a volume of 100 L.

Referring to FIG. 21, in a particular embodiment, an apparatus for dispensing medical items to a subject is a standalone stationary device with a capacity of 100 designed for pharmacy and/or hospital use. In this embodiment, an apparatus for dispensing medical items includes a keypad for user input 113 and a payment interface 114 allowing a user to optionally identify a subject, enter medical item information, and/or pay for dispensed items. Further in this embodiment, medical items are dispensed from a removable inventory container 115 from a dispensing door 116. Where a medical item is a medication, it is dispensed in a standardized unit pack labeled with drug name, dosage, expiration date, lot number, and the like.

Referring to FIGS. 18-21, in particular embodiments, an apparatus for dispensing medical items to a subject is operated remotely by a live, licensed healthcare provider. In other embodiments, an apparatus for dispensing medical items to a subject operates in an emergency mode and dispenses one or more medical items autonomously (e.g., without remote operation by a live healthcare provider). In further embodiments, an apparatus for dispensing medical items operating in an emergency mode utilizes a module for risk assessment and/or diagnostic/therapeutic analysis to guide dispensing determinations.). In still further embodiments, an apparatus for dispensing medical items operating in an emergency mode activates the emergency response system (e.g., police, fire, EMS, etc.).

Continuing to refer to FIGS. 18-21, in some embodiments, a keypad for use input is a simplified keypad for use by a subject with communications limitations (e.g., due to age, infirmity, disability, etc.), wherein each key is associated with a color, a shape, and health/communication concept. See e.g., FIG. 28.

Figure 28:
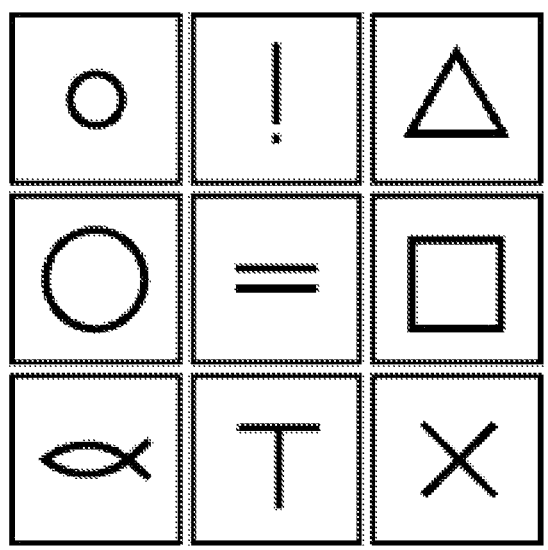
FIG. 28 shows a non-limiting example of a key pad for use by a subject in communicating with a system, device, or telemedical care provider; in this case, a nine key pad wherein each key is associated with a color, a shape, and health/communication concept.

Referring now to FIG. 28, in a particular embodiment of a simplified keypad for use by a subject with communications limitations the keys include those with the following characteristics:

| Color | Shape | Meaning |
|---|---|---|
| White | Small inner circle or the moon | COLD |
| Red | Exclamation point | PAIN/BLEEDING |
| Orange | Triangle | CAUTION/UNSURE |
| Yellow | Large outer circle or the sun | HOT |
| Green | Equal sign | YES/WELL/GO |
| Blue | Square | SHORT OF BREATH |
| Indigo | Ellipse or fish | TREATMENT |
| Violet | T | DIZZY/DYSURIA/GI VOMITING/DIARRHEA |
| Black | X | NO/DONE/STOP |

Figure 5:
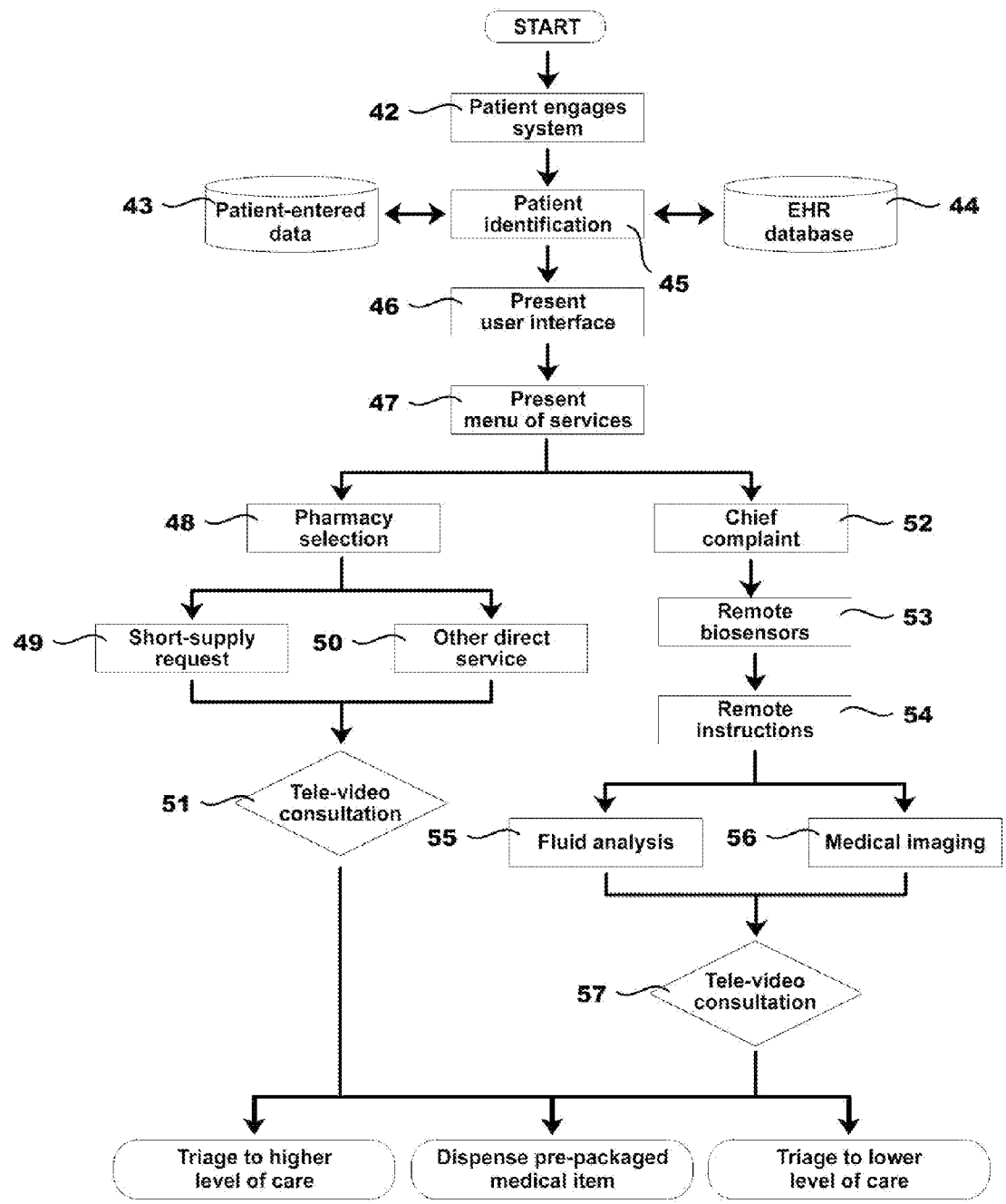
FIG. 5 shows a non-limiting example of a process flow for potential subject encounters with a system for providing remote medical diagnosis and therapy; in this case, a process including patient identification, pharmacy-related options, and acute, urgent care options, resulting in one of several outcomes including a recommendation to triage to a higher level of care, dispensing a medical item, or triage to a lower level of care.

Referring to FIG. 5, in a particular embodiment, a subject or caregiver engaging the device 42, getting review of their case by a pharmacist, physician, nurse, veterinarian, etc., being examined by a biosensor, and getting a medical item dispensed. In a further embodiment, the process starts with a subject user or caregiver user request for possible diagnosis and or treatment at the urgent care robot by inserting a client insurance and or credit/debit card with a client pharmacy or client physician/veterinarian practice membership card or barcode or mobile application equivalent with user name/password 45. In some embodiments, subject identification involves consulting medical databases of EHRs 44. In some embodiments, a menu of options 47 is presented to the user including, for example, options to indicate: a) need for a short supply medication 470 of expired or new prescription not yet immediately available; b) subject has an acute complaint 52 desiring a possible diagnosis, a possible treatment, and potentially triage to a higher or lower level of care. In further embodiments, if there is need only for a pharmacist to review an existing prescription 49 that is done and the pharmacist labels a prepackaged short supply of medication and counsels the user via video conference 51 on proper use of the medication and possible side effects including a possible review of other medications the subject is using and request if subject needs consultation with a same state physician or veterinarian or a professional extender (i.e., same state licensed nurse practitioner or physician assistant). In some embodiments, biosensors 53 remotely controlled by the pharmacist or another healthcare provider may be used to obtain vital signs, images of superficial parts or whole of the body including eyes and retinas 56, or screening clinical analyses of blood or urine 55. In various embodiments, specialized robotic remotely controlled sensors may include ultrasound probes (a gel is needed and provide for application on the skin to obtain images) that the user can place on the body under the direction of a remote ultrasound technician or other licensed healthcare provider who indicates instructions 54 to the user about orienting the probe while the remote controller adjusts viewing windows and frequency settings to obtain optimal imaging of the body structure being examined, i.e., the heart or gallbladder for imaging, or Doppler blood flow in a blood vessel, or ultrasound audio for, i.e., auscultation of breath and heart sounds. In further embodiments, the healthcare provider analyzes verbal and biosensor acquired data, uses a decision system 57 to make appropriate care recommendations which may include dispensing a limited supply of a medical item or triaging the subject to a lower or higher level of care.

Figure 6:
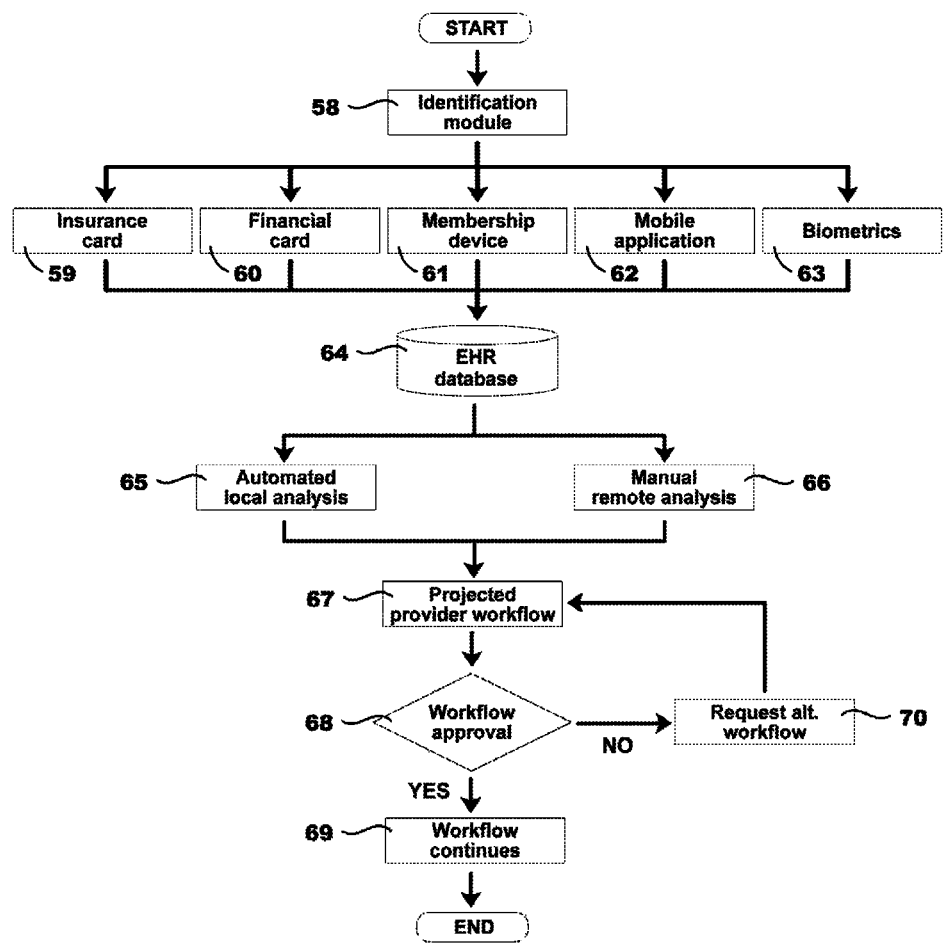
FIG. 6 shows a non-limiting example of a process flow for subject identification; in this case, a process utilizing identifying information from sources such as an insurance card, a financial card, a membership device, a mobile application, and/or biometrics.
Figure 7:
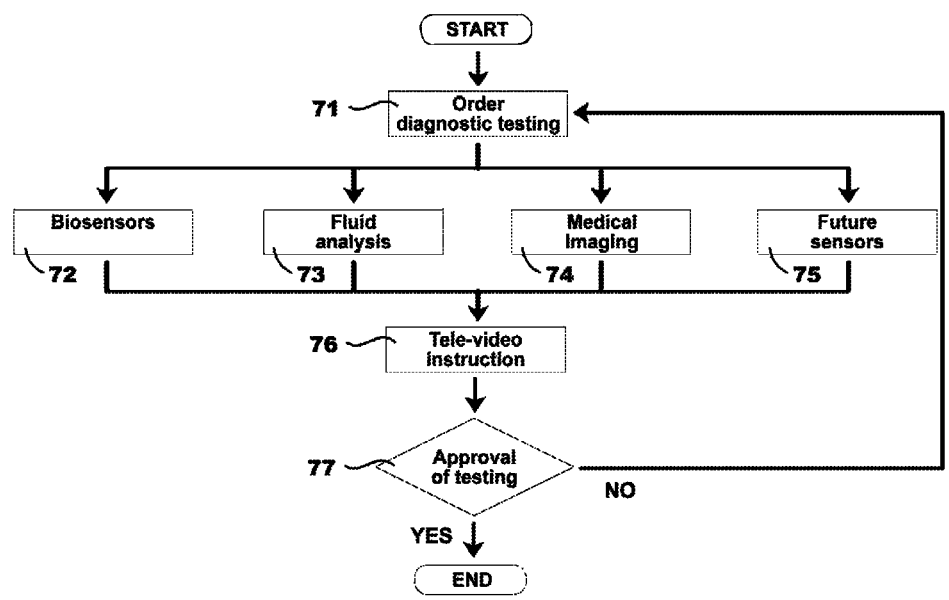
FIG. 7 shows a non-limiting example of a process flow for providing remote medical diagnosis; in this case, a process including diagnostic tests utilizing biosensors, fluid analysis, medical imaging, and/or other types of sensors.
Figure 8:
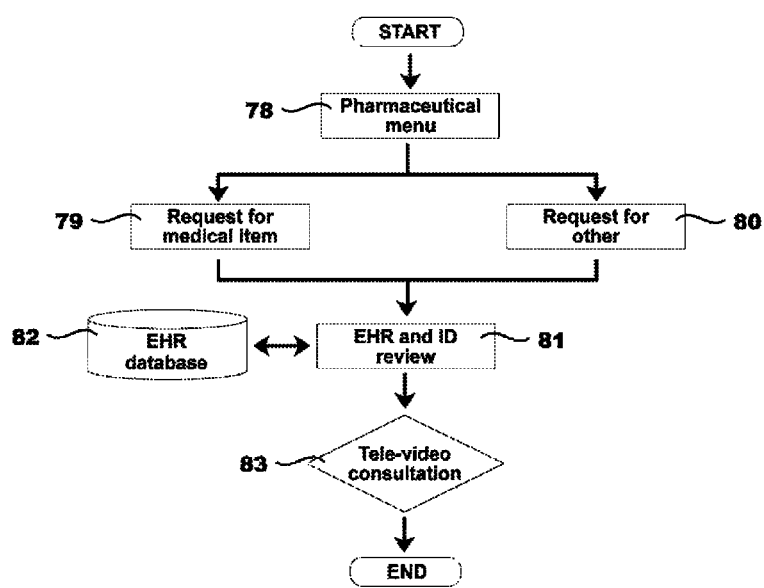
FIG. 8 shows a non-limiting example of a process flow for providing remote pharmacy services; in this case, a process including tele-video consultation with a live, licensed healthcare provider.

FIGS. 6, 7, and 8 provide exemplary details of select portions of the process flow depicted in FIG. 5.

Referring to FIG. 6, in a particular embodiment, subject identification begins with engagement of an identification software module 58 by a subject who presents an insurance card 59, a financial card 60 (e.g., debit card, credit card, etc.), a device issued to members of a health plan 61 (e.g., RFID device, etc.), a mobile application 62, or biometric information 63. The module queries one or more databases, including an EHR database 64, to analyze identifying information via alternative automated 65 and manual 66 processes.

Referring to FIG. 7, in a particular embodiment, analysis of a complaint via remote diagnosis begins with an order of diagnostic testing by a healthcare provider 71. Remote operation or supervision of biosensors 72, fluid analysis and culture apparatus 73, medical imaging apparatus 74 is conducted via audio-video instruction 76 of either a subject or an onsite healthcare provider present with a subject.

Referring to FIG. 8, in a particular embodiment, remote pharmacy services are offered via presentation of a menu of pharmaceutical options 78. A subject alternatively requests dispensing of a particular medical item 79 or another request 80. Appropriateness of pharmaceutical requests requires query of an EHR database 82 and review of EHRs and subject identification information 81. An audio-video conference 83 between a subject and a remote healthcare provider (e.g., a pharmacist) further provides opportunity to assess the request and/or instruct a subject on use of the pharmaceutical.

Figure 9:
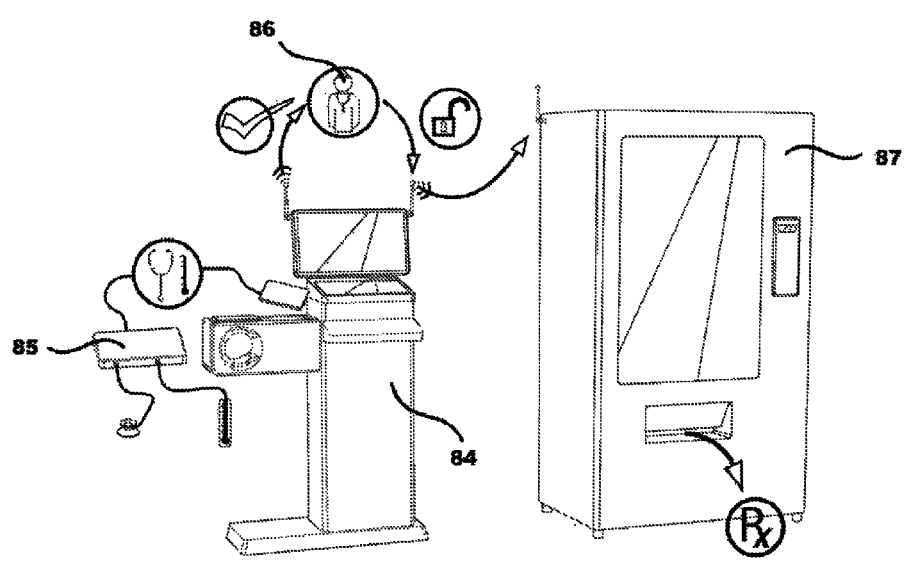
FIG. 9 shows a non-limiting example of a system for providing remote diagnosis and therapy to a subject; in this case, a system including a stationary networked biosensor station and a stationary networked apparatus for dispensing medical items.

Referring to FIG. 9, in a particular embodiment, a system for providing remote medical diagnosis and therapy to a subject includes a stationary device for collecting biosensor data 84 and wirelessly transmitting the data to a telemedical care provider 86. In this embodiment, the device for collecting biosensor data is in communication with a portable diagnostic module 85 extending accessibility to immobile subjects. Further in this embodiment, a telemedical care provider optionally authorizes dispensing of appropriate medical items from a stationary apparatus for dispensing medical items from an inventory of items 87 risk profiled to a particular subject, family, population, venue, circumstance, or situation, which is wirelessly in communication.

Figure 10:
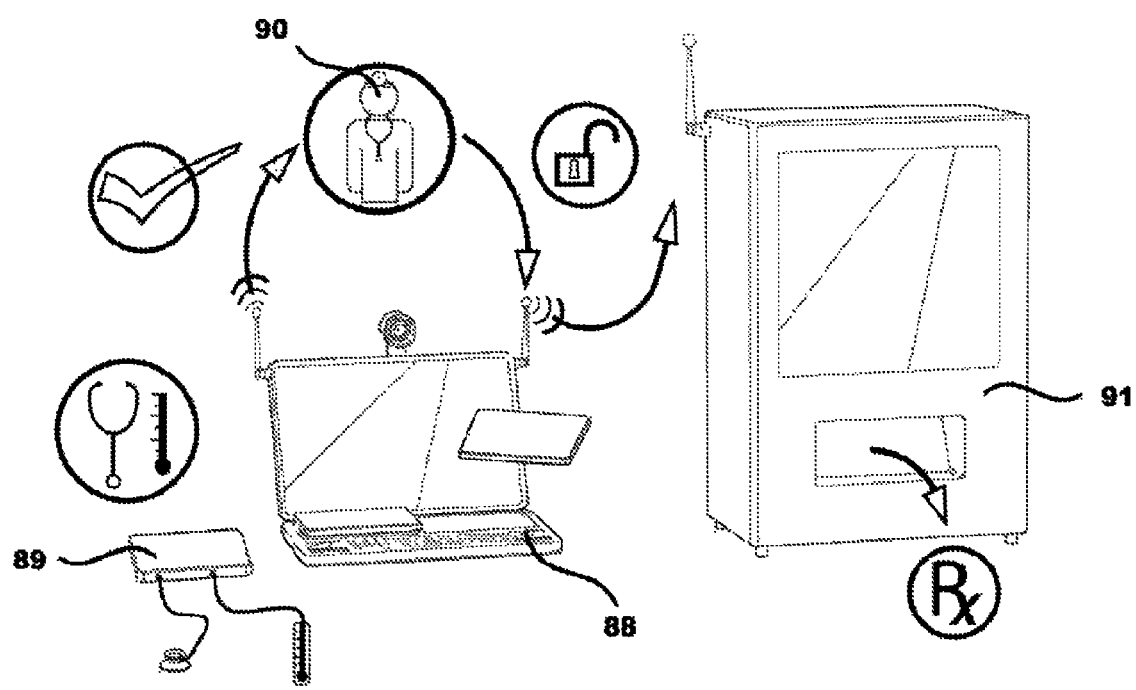
FIG. 10 shows a non-limiting example of a system for providing remote diagnosis and therapy to a subject; in this case, a system including a portable networked biosensor device and a stationary networked apparatus for dispensing medical items.

Referring to FIG. 10, in a particular embodiment, a system for providing remote medical diagnosis and therapy to a subject includes a portable device for collecting biosensor data and wirelessly transmitting the data to a telemedical care provider. In this embodiment, the device for collecting biosensor data 88 is in communication with a plurality of portable diagnostic modules 89 selected for their utility in addressing the risks facing a particular subject, family, or population, or those in a particular place or situation. Further in this embodiment, a telemedical care provider 90 optionally authorizes dispensing of appropriate medical items from a stationary apparatus for dispensing medical items from an inventory of items 91 risk profiled to a particular subject, family, population, venue, circumstance, or situation, which is wirelessly in communication.

Figure 11:
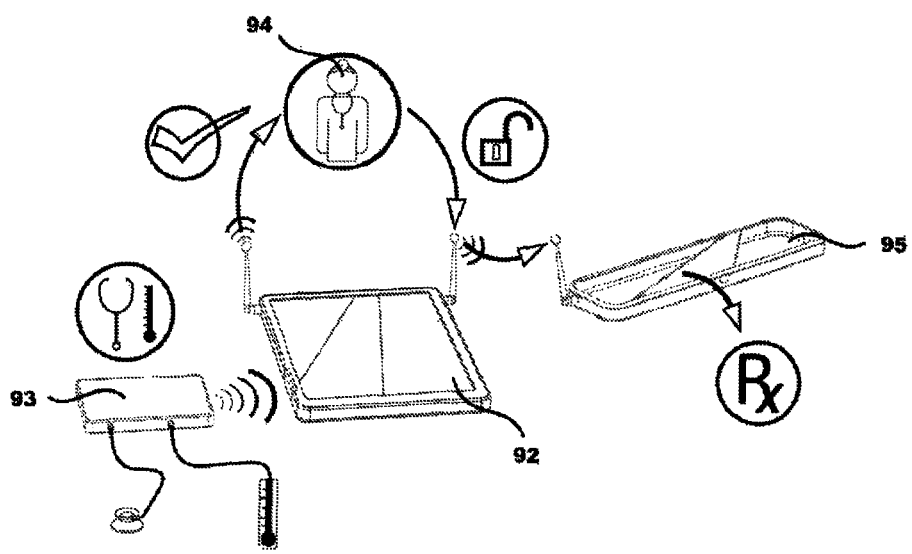
FIG. 11 shows a non-limiting example of a system for providing remote diagnosis and therapy to a subject; in this case, a system including a portable networked biosensor device and a portable networked apparatus for dispensing medical items.

Referring to FIG. 11, in a particular embodiment, a system for providing remote medical diagnosis and therapy to a subject includes an ultraportable device for collecting biosensor data 92 and wirelessly transmitting the data to a telemedical care provider 94. In this embodiment, the device for collecting biosensor data is in communication with a portable diagnostic module 93 selected for its utility in addressing the risks facing a particular subject, family, or population, or those in a particular place or situation. Further in this embodiment, a telemedical care provider optionally authorizes dispensing of appropriate medical items from a portable apparatus for dispensing medical items from a limited inventory of items 95 risk profiled to a particular subject, family, population, venue, circumstance, or situation, which is wirelessly in communication.

Biosensors

In some embodiments, the systems for providing remote medical diagnosis and therapy to a subject include a networked medical device including a processor, a memory, and an operating system configured to perform executable instructions. In further embodiments, the medical device includes one or more biosensors.

Any suitable biosensor is used with the systems, devices, software, and methods disclosed herein.

In some embodiments, a biosensor is a physicomechanical sensor. In further embodiments, a biosensor includes, by way of non-limiting examples, a thermometer, a scale, a blood pressure sensor, and a respirometer. See, e.g., FIG. 12.

In some embodiments, a biosensor is a physicochemical sensor. In further embodiments, a biosensor includes physicochemical sensors for culturing and/or analyzing a tissue sample or a fluid sample such as blood, saliva, urine, mucus, hair, etc. In further embodiments, analysis includes qualitative analysis, such as detecting a property, detecting a substance, detecting a reaction, or detecting a pathogen. In further embodiments, analysis includes quantitative analysis, such as measuring a property, measuring a substance, measuring a reaction, or measuring a pathogen. In still further embodiments, a biosensor includes, by way of non-limiting examples, blood chemistry devices, urinalysis devices, blood glucose sensors, pulse oximeters, and the like. See, e.g., FIG. 13.

In some embodiments, a biosensor is an imaging sensor. In further embodiments, an imaging sensor includes, by way of non-limiting examples, a video camera, a high definition video camera, a thermal imaging camera, a thermography device, magnetic resonance imaging (MRI) device, an ultrasound device (e.g., echocardiography, obstetrical sonography, intravascular ultrasound, etc.), and a tomography device (e.g., computed tomography (CT), computed axial tomography (CAT), etc.). See, e.g., FIG. 14.

In some embodiments, a biosensor is an acoustic sensor. In further embodiments, a biosensor includes, by way of non-limiting examples, a stethoscope and specialized remote auscultation devices adapted for hearing gut sounds, heart sounds, or lung/breath sounds.

In some embodiments, a biosensor is a bioelectric sensor. In further embodiments, a biosensor includes, by way of non-limiting examples, an electrocardiography (ECG or EKG) device, a heart rate monitor, an electromyography (EMG) device, an impedance sensor, and a galvanic skin response sensor.

The networked medical devices described herein optionally utilize biosensors to perform a wide range of suitable diagnostic tests. In various embodiments, suitable diagnostic tests include, by way of non-limiting examples, blood sugar test (e.g., diabetes), complete blood count or CBC blood test (e.g., anemia, infection, etc.), troponin blood test (e.g., myocardial infarction), serum creatinine blood test (e.g., kidney function), Chem 7 blood test (e.g., nutritional status, electrolytes imbalances, etc.), ultrasound and fiber optic camera examination, spirometer test (e.g., asthma, COPD, etc.), INR blood test (e.g., Coumadin patient), urine test detecting blood (e.g., gross and microscopic hematuria), blood cholesterol test (e.g., hyperlipidemia), blood pressure test (intermittent vs. continuous) (e.g., hypertension or hypotension), pulse oximetry test (e.g., hypoxia, etc.), and temperature measurement (e.g., fever, etc.), and 12 lead EKG (e.g., myocardial infarction, arrhythmias, etc.).

Many modes of operation are suitable for biosensors used with the systems, devices, software, and methods disclosed herein.

In some embodiments, a biosensor operates in an automated mode. In further embodiments, an automated biosensor operates according to a pre-planned script or set of instructions without direction from a healthcare provider, an operator, or a subject. For example, a digital scale automatically weights a subject without instruction and records their weight.

In some embodiments, a biosensor operates in a subject-operated mode. In further embodiments, a subject directs or controls a biosensor. For example, a subject places a wired electronic thermometer under their tongue and activates a control to begin a body temperature reading. In some embodiments, a subject operates a biosensor under instruction provided by a live, remote healthcare provider or a software application.

In some embodiments, a biosensor operates in a remotely controlled mode. In further embodiments, a healthcare provider directs or controls a biosensor from a remote location. For example, a live healthcare provider uses a software application to remotely manipulate and position an autofocus, high definition video camera that is mounted on a robotic arm to examine a skin lesion on a subject's face. By way of further example, a live healthcare provider uses a software application to remotely manipulate and position an ultrasound probe to examine a subject's heart.

In some embodiments, a biosensor operates in a subject-operated mode and/or a remotely controlled mode and is further observed, assisted, or operated by technician. In further embodiments, a technician is present with the subject (e.g., onsite). For example, a live, remote healthcare provider remotely supervises and operates an ECG device to interpret the electrical activity of the heart of a subject. A technician present with the subject assists in connecting the electrodes to appropriate sites on the surface of the subject's skin.

In various embodiments, one or more biosensors are capable of operating in multiple modes described herein. In further embodiments, such a biosensor switches between modes at predetermined points in a procedure. In further embodiments, such a biosensor switches between modes upon request of a healthcare provider, an onsite technician a subject, or an appropriate caregiver. For example, a subject can position an ultrasound probe under the direction of a healthcare provider and then activate a control that shifts control of the probe to a live, remote healthcare provider to fine tune the positioning via remote robotic controls.

In some embodiments, a biosensor is permanently attached to a device or system described herein. In other embodiments, a biosensor is reversibly attached to a device or system described herein and communicates with the device or system via wireless protocols including, by way of non-limiting embodiments, infrared, Bluetooth, ZigBee, Wi-Fi, and 3G/4G wireless protocols. In other embodiments, a biosensor is reversibly attached to a device or system described herein. In further embodiments, a removable biosensor stores data in memory and the data is communicated to the device or system at a later time when the biosensor is reconnected to the device or system.

In some embodiments, the systems and devices described herein do not include permanent biosensors. In further embodiments, remote diagnosis and therapy is provided by way of, for example, the experience of one or more live healthcare providers, data contained in electronic records and databases (e.g., EHRs, medical literature, news, etc.), data communicated and input by a subject or an appropriate caregiver, software for predicting acute risks and health and/or economic outcomes of patients, potential therapies, and the like, including combinations thereof.

Telecommunications

In some embodiments, the systems, devices, software, and methods described herein include hardware and software elements for establishing, conducting, and maintaining telecommunications. In further embodiments, telecommunications are used by the devices and systems described herein, for example, to communicate with subjects, healthcare providers, and other users of the devices and systems; to access electronic health records and other sources of information; to monitor, regulate, control, and exchange data with biosensors; to monitor, regulate, control, and exchange data with an apparatus for dispensing medical items; to monitor, regulate, control, and exchange data with a module for applying a diagnostic or therapeutic analysis; and to monitor, regulate, control, and exchange data with a module for providing instantaneous encounter-specific financial insurance coverage that includes a level of guarantee and an associated premium.

In some embodiments, a module for telecommunications creates a communications link. In further embodiments, communication links enable one-way, two-way, or multi-way communication. In various further embodiments, communication links enable communication via, by way of non-limiting examples, telephone, push-to-talk, audio conference, video conference, SMS, MMS, instant message, Internet bulletin board, blog, microblog, fax, Internet fax, electronic mail, VoIP, or combinations thereof. In some embodiments, one or more communications links are interactive and provide real-time (e.g., synchronous) or near real-time (e.g., asynchronous) two-way communication or transfer of data and/or information.

In some embodiments, a module for telecommunications creates multiple communications links. In various embodiments, a module for telecommunications creates 1, 2, 3, 4, 5, 6, 7, 8, 9, 10, 20, 30, 40, 50, 60, 70, 80, 90, 100 or more communications links, including increments therein. In further embodiments, multiple communications links are created and maintained serially, or one at a time. In other embodiments, multiple communications links are created and maintained in parallel, or simultaneously.

In some embodiments, the communications link enables a live, remote healthcare provider to communicate with one or more other parties and vice versa. In some embodiments, the communications link is between a live, remote healthcare provider and a subject or a group of subjects. In some embodiments, the communications link is between a live, remote healthcare provider and an onsite caregiver or group of caregivers. In further embodiments, an onsite caregiver is a person who has an interest in, or responsibility for, the health and welfare of a subject and is present with the subject at least once, intermittently, often, or full-time. Non-limiting examples of onsite caregivers include an employee of a subject, a member of a subject's family, a physician, a dentist, a physician assistant, a nurse practitioner, a registered nurse, a pharmacist, a chiropractor, a licensed practical nurse, a veterinarian, a veterinary technician, a certified ultrasound technician, radiology technician, a psychologist, a social worker, a physical therapist, an occupational therapist, a speech therapist, a cardiac catheterization technician, a clinical pathology laboratory technician, a medical aesthetician, a licensed medical technologist, a hospice worker, an emergency medical technician, a paramedic, a police officer, and a firefighter. In further embodiments, an onsite caregiver communicates with a live, remote healthcare provider on behalf of a subject or to describe the condition of the subject. In some embodiments, the communications link is between a live, remote healthcare provider and one or more medical product or service providers including, by way of non-limiting examples, pharmaceutical product providers, diagnostic service providers, and therapeutic service providers. In further embodiments, a live, remote healthcare provider communicates with one or more medical product or service providers regarding products or services that are prescribed or recommended for a patient or the costs associated with such products or services. In some embodiments, the communications link is between a live, remote healthcare provider and one or more consultants including, by way of non-limiting examples, medical consultants, legal consultants, insurance consultants, and financial consultants. In further embodiments, a live, remote healthcare provider communicates with one or more medical consultants regarding a subject's medical history, diagnosis, past, current, or contemplated therapies, or prognosis. In further embodiments, a live, remote healthcare provider communicates with one or more legal consultants regarding compliance with applicable laws, regulations, and rules. In further embodiments, a live, remote healthcare provider communicates with one or more insurance and financial consultants regarding a subject's eligibility, coverage, benefits, deductable, or payment status. In still further embodiments, multiple communications links are established with a plurality of providers and/or consultants to form a conference to remotely discuss the care of one or more subjects.

In various embodiments, the module for telecommunications utilizes many suitable communications channels. In some embodiments, the module for telecommunications utilizes wired or fiber optic telephone, wired or fiber optic Internet, Wi-Fi, and the like, including combinations thereof. In various embodiments, the module for telecommunications utilizes a wide array of suitable communications protocols. In some embodiments, the module for telecommunications utilizes wired communications protocols. In some embodiments, the module for telecommunications utilizes wireless communications protocols. In further embodiments, suitable communications protocols include, by way of non-limiting examples, 3G (3rd generation mobile telecommunications), 4G (4th generation mobile telecommunications), and geosynchronous and low Earth orbit (LEO) satellite, or combinations thereof. In further embodiments, suitable communications protocols include, by way of non-limiting examples, transmission control protocol/internet protocol (TCP/IP), hypertext transfer protocol (HTTP), hypertext transfer protocol secure (HTTPS), file transfer protocol (FTP), user datagram protocol (UDP), internet message access protocol (IMAP), post office protocol (POP), simple mail transfer protocol (SMTP), and simple network management protocol (SNMP), or combinations thereof. In further embodiments, suitable communications protocols include, by way of non-limiting examples, voice over Internet protocol (VoIP) and voice, or combinations thereof.

In some embodiments, the module for telecommunications includes hardware and software to allow communication via multiple, redundant communications protocols. In further embodiments, the module switches between protocols based on user preference, protocol availability, signal strength, and the like. In some embodiments, the systems and devices described herein include a non-communication mode, wherein a module for telecommunications does not operate. In further embodiments, the systems and devices described herein operate in a non-communication mode when communication protocols fail or when communication channels or signals fail or are lost. In still further embodiments, the systems and devices described herein operate in a non-communication mode when placed in a location where one or more communication protocols, channels, or signals are unavailable.

In some embodiments, the systems and devices described herein do not include telecommunications elements. In further embodiments, remote diagnosis and therapy is provided by way of, for example, the experience of one or more live healthcare providers, data stored locally, data communicated and input by a subject or an appropriate caregiver, data captured by biosensors, software for predicting acute risks and health and/or economic outcomes of a patients and potential therapies, and the like, including combinations thereof.

In some embodiments, the module for telecommunications provides a graphic representation of the subject and the live healthcare provider. In some embodiments, a graphic representation is two-dimensional. In other embodiments, a graphic representation is three-dimensional. In some embodiments, a three-dimensional graphic representation is a virtual reality environment. In some embodiments, the subject and the live healthcare provider are depicted similarly to their actual appearance. In further embodiments, the actual appearance of a healthcare provider is determined based on historic records such as personnel files or based real-time information captured by a digital camera, video camera, and/or microphone. In further embodiments, the actual appearance of a subject is determined based on historic records such as medical records or based real-time information captured by a digital camera, video camera, and/or microphone. In other embodiments, the subject and the live healthcare provider are depicted differently from their actual appearance. In further embodiments, a subject or a healthcare provider selects an appearance for the graphic representation. In some embodiments, a graphic representation depicts the subject and the live healthcare provider in a virtual medical setting. In further embodiments, a virtual medical setting is, by way of non-limiting example, a medical office, an examination room, a diagnostic facility, a medical laboratory, an ultrasound station, a classroom, and the like.

In some embodiments, the systems, devices, software, and methods described herein further comprise a software module for electronically recording communications conducted over one or more communications links. In further embodiments, the audio, video, health record data, financial record data, and insurance record data exchanged are recorded. In still further embodiments, recorded communications are used to ensure sound medical policies and procedures and compliance with applicable laws, regulations, and rules.

In some embodiments, the communication links meet applicable legal data security standards. In some embodiments, the communication links meet applicable legal patient privacy standards. In further embodiments, the applicable legal standards include, by way of non-limiting examples, the Health Insurance Portability and Accountability Act of 1996 and The Health Information Technology for Economic and Clinical Health Act of 2009. In some embodiments, live and/or recorded electronic communications are encrypted. In further embodiments, cryptographic protocols such as Secure Sockets Layer (SSL) or Transport Layer Security (TLS) are applied to Internet-based communications such as web traffic, electronic mail, Internet faxing, instant message, and VoIP.

Electronic Health Records

EHRs, also known as electronic medical records (EMRs) and electronic patient records (EPRs), are utilized in a variety of ways by multiple aspects of the systems, devices, software, and methods described herein. In some embodiments, the systems, devices, software, and methods described herein include a software module for accessing one or more EHRs for a subject. In further embodiments, a module for telecommunications accesses one or more electronic health records for a subject. In some embodiments, the systems, devices, software, and methods described herein include a module for applying a diagnostic or therapeutic analysis. In further embodiments, diagnostic or therapeutic analysis comprises accessing, for example, one or more electronic health records and/or medical databases.

In some embodiments, a software module for accessing one or more EHRs for a subject enables a healthcare provider to access EHRs without modifying the records. In other embodiments, the software module enables a live, remote, adjunct healthcare provider to access and modify one or more records. In other embodiments, the software module enables a healthcare provider to create EHRs. In further embodiments, the software module enables a healthcare provider to add EHRs to a storage system. In some embodiments, one or more EHRs are historic, being created prior to access by the systems and devices described herein and electronically stored. In other embodiments, one or more EHRs are live, being created in real-time by, for example, a subject, an onsite caregiver, or other medical personnel present with the subject. In some embodiments, an electronic device present with a subject generates EHRs. In further embodiments, the electronic device is a biosensor that is part of the systems and devices described herein.

In view of the disclosure provided herein, those of skill in the art will recognize that an EHR is a systematic collection of electronic health information about an individual patient or population. In some embodiments, an EHR includes records of therapies, prescriptions, orders, or instructions issued by a healthcare provider for a subject. EHRs suitable for use with the systems, devices, software, and methods disclosed herein optionally include a range of data in comprehensive or summary form, including, by way of non-limiting examples, medical history, medication record, medication history, authenticated physical exam, laboratory test reports (e.g., pathology report, blood cell count report, blood culture report, urinalysis report, throat culture report, and genetic test report), imaging reports (e.g., X-ray, CT scan, MRI, and ultrasound), demographics, family history, allergies, adverse drug reactions, illnesses, chronic diseases, hospitalizations, surgeries, immunization status, vital signs and other biometrics (e.g., body temperature, heart rate, blood pressure, respiratory rate, blood diagnostics such as oxygen saturation, glucose concentration, and blood count, urine diagnostics such as specific gravity, protein, glucose, and blood, other bodily fluid diagnostics, and diagnostic images or imaging reports), age, weight, Observations of Daily Living (ODLs), insurance benefits, insurance, eligibility, insurance claim information, and billing information.

In some embodiments, a software module for accessing one or more EHRs for a subject and/or a software module for telecommunications is further configured to access subject insurance coverage, eligibility, and deductable information or out-of-pocket payment information. In further embodiments, a software module additionally accesses information from one or more pharmaceutical, diagnostic, or therapeutic service providers. In other embodiments, the systems, devices, software, and methods described herein further comprise a separate software module to access subject insurance coverage, eligibility, and deductable information or out-of-pocket payment information and information from one or more pharmaceutical, diagnostic, or therapeutic service providers.

In some embodiments, a subject authorizes a healthcare provider to access their health records. In further embodiments, systems, devices, software, and methods described herein include a software module for verifying a patient's authorization for a healthcare provider to access their health records. In some embodiments, the authorization meets applicable legal requirements. In further embodiments, the applicable legal requirements include, by way of non-limiting examples, those in the Health Insurance Portability and Accountability Act of 1996 and the Health Information Technology for Economic and Clinical Health Act of 2009. In some embodiments, a software module for verifying a patient's authorization for a healthcare provider to access their health records is further configured to verify a healthcare provider's identity.

In view of the disclosure provided herein, those of skill in the art will recognize that suitable EHRs include those created and maintained in accordance with published standards, including XML-based standards such as Continuity of Care Record (CCR). Suitable EHRs also include those utilizing the DICOM communications protocol standard for representing and transmitting radiology (and other) image-based data, the HL7 standardized messaging and text communications protocol, and ANSI X12 transaction protocols for transmitting patient and billing data. Additionally, those in the art will recognize that suitable EHRs include those operable with open standard specifications that describe the management, storage, retrieval, and exchange of health data, such as openEHR (available at http://www.openehr.org/).

Diagnostic or Therapeutic Analysis

In some embodiments, the systems, devices, software, and methods described herein include a software module for applying a diagnostic or therapeutic analysis. In some embodiments, a software module for applying a diagnostic or therapeutic analysis is used by a live healthcare provider. In further embodiments, a software module for applying a diagnostic or therapeutic analysis is supervised, monitored, or operated by any of the live healthcare providers described herein. In some embodiments, the software module for applying a diagnostic or therapeutic analysis supplements the professional judgment of a live healthcare provider. In other embodiments, a software module for applying a diagnostic or therapeutic analysis is configured to operate in an automated mode and does not require supervision, monitoring, or operation by a healthcare provider.

In some embodiments, the goal of applying a diagnostic or therapeutic analysis in a healthcare encounter is to assess and/or quantify risk to a subject. In further embodiments, the goal of applying a diagnostic or therapeutic analysis in a healthcare encounter is to reduce risk to a subject. In other embodiments, the goal of applying a diagnostic or therapeutic analysis is to determine an inventory of medical items risk profiled to a subject, a family, a population, a venue, and/or a situation. In some embodiments, the goal of applying a diagnostic or therapeutic analysis in a healthcare encounter is to classify the healthcare encounter as convenient, semi-urgent, urgent, and/or emergent. In some embodiments, the goal of applying a diagnostic or therapeutic analysis in a healthcare encounter is to classify a subject's illness as acute, subacute, and/or chronic. In some embodiments, the goal of applying a diagnostic or therapeutic analysis in a healthcare encounter is to determine a probability of an adverse outcome. In further embodiments, the goal of applying a diagnostic or therapeutic analysis in a healthcare encounter is to determine a probability of an adverse outcome over a specified period of time in the future with and without certain interventions and/or therapies. In still further embodiments, a probability is expressed by the software module as a percentage. In light of the disclosure provided herein, those of skill in the art will recognize that disease and illness have multiple levels of severity and should be treated with an appropriately correlated level of care or intensity of service.

In some embodiments, the module for applying a diagnostic or therapeutic analysis collects data and information from a variety of sources to determine a severity of illness, injury, or condition of a subject presenting with an acute complaint. In further embodiments, the module determines the medical necessity of a variety of possible therapies to arrive at an appropriate level of care. In still further embodiments, the module recommends an intensity of service based on the level of care required.

In some embodiments, the diagnostic or therapeutic analysis comprises performing statistical analysis, performing probability calculations, making recommendations, and making outcome predictions to predict a health or economic outcome of a patient or therapy. In further embodiments, a prediction of a health or economic outcome is performed in real-time and is individualized. In still further embodiments, a prediction of a health or economic outcome is probabilistic-based and uses historic, peer-reviewed health or economic data as well as emerging health or economic data. In some embodiments, the diagnostic or therapeutic analysis comprises: 1) accessing one or more information sources selected from the group consisting of: electronic health records, medical databases, medical literature, economic databases, economic literature, insurance databases, and insurance literature; 2) performing natural language processing to identify information determined to be of value in determining health and economic risks of an adverse outcome related to a health encounter; and 3) transforming the data into numerical format useful for application in statistical modeling to determine health and economic risks of an adverse outcome related to a health encounter.

In some embodiments, the diagnostic or therapeutic analysis includes statistical analysis, probability calculations, recommendations, and outcome predictions based, in whole or in part, on empirical data gained by means of observation or experiments. In still further embodiments, the software module is an empirical decision making mechanism that utilizes, for example, published medical practice guides and decision flow charts. In still further embodiments, the software module performs meta-analysis of published, peer-reviewed literature to formulate guidelines and protocols for a live healthcare provider to optimally deliver services to patients.

In some embodiments, the diagnostic or therapeutic analysis includes statistical analysis, probability calculations, recommendations, outcome predictions, and risk predictions based, in whole or in part, on emerging health or economic data, for example, timely, non-historic data. In further embodiments, emerging health or economic data includes, by way of non-limiting examples, patient-specific parameters, provider-specific parameters, and third party data. In still further embodiments, emerging patient-specific parameters include, by way of non-limiting examples, severity of illness, real-time vital signs, and current symptoms. In still further embodiments, emerging provider-specific parameters include, by way of non-limiting examples, intensity of services required and resources currently available. In still further embodiments, emerging third-party data is sourced from, by way of non-limiting examples, third party commercial healthcare payers or providers, pharmaceutical companies, private medical centers, professional healthcare societies or associations, economic or healthcare databases, Medicare bulletins, U.S. Centers for Disease Control and Prevention (CDC) announcements, U.S. Federal Drug Administration (FDA) announcements, other domestic or foreign government communications, and medical conventions wherein new emerging information may have been announced but not yet published in medical journals for peer review. In some embodiments, the emerging health or economic data refers to data obtained from urgent news and/or announcements distributed in public media. In some embodiments, the emerging health or economic data is derived from a source that has not been peer reviewed by one or more healthcare or economic professionals. In other embodiments, the emerging health or economic data is derived from a source that has been peer reviewed by one or more healthcare or economic professionals. In some embodiments, the emerging health or economic data is derived from a source that has not been published. In other embodiments, the emerging health or economic data is derived from a source that has been published.

In some embodiments, the diagnostic or therapeutic analysis comprises utilization of a CMD (Complex Medical Decision) machine. In further embodiments, a CMD machine is a computer-implemented decision making technology, built to provide probabilistic outcomes of health or economic interest, for a particular subject (e.g., a healthcare patient/subject, a healthcare provider therapy, or a healthcare payer, etc.) or set of subjects, given a set of data or input parameters. In some embodiments, the outcome given by the CMD machine is determined by a final set of data or input parameters that have been processed and transformed from structured and unstructured information, to usable information, about the particular subject or set of subjects.

In some embodiments, a CMD machine has the ability to improve its performance as it acquires experience or data. In further embodiments, a CMD machine "learns" from emerging information (i.e., subject data) as it is being used, and adapts to the user's (e.g., healthcare provider) situation (i.e., types of subjects, types of measurements, natural language used, and/or any other inherent characteristic). In still further embodiments, the system has the ability to process information in successive time intervals, after some initial time, when the initial invocation of the system took place. Finally, in some embodiments, a CMD machine performs variable importance analysis so that the user can gain information about the causes of the high/low risk of a particular subject or set of subjects.

In some embodiments, the diagnostic or therapeutic analysis described herein utilizes a CMD machine that is built on information obtained by sources including, but not-limited to, health care providers such as hospitals, human or veterinary healthcare professionals, and the like.

In various embodiments, the information used or processed by the system is in structured and/or unstructured format. In further various embodiments, such information is found in EHRs as well as Clinical Notes (CNs). In some embodiments, information contained in EHRs can be in structured database-like form, such as tab delimitated files, comma separated files, spreadsheets etc., or in the form of unstructured information, such as free notes/text, impressions, assessments, evaluations, etc. In some embodiments, information contained in CNs is, for the most part, in unstructured form. In some embodiments, an initial database of subjects, containing EHRs and CNs and label-type outcomes (0 for survived/not morbid outcome-1 for died/morbid outcome) for each health care provider using a CMD machine will be used, herein coined a Training Set (TS). The initial TS will be used to train systems a) and b) that are described herein.

In some embodiments, a CMD machine comprises a) a Natural Language Processing (NLP) system, b) a Probabilistic Classifier (PC) system, and c) an Active Learning (AL)/Novelty Detection (ND) system. In further embodiments, a NLP system processes all aspects of the TS that are in unstructured format and/or natural language and performs a variable or input extraction task. In further embodiments, a PC system uses information of the TS extracted by the NLP system, as well as information in the TS that is in structured format to provide probabilistic outcomes for the particular subject or set of subjects. In some embodiments, once the actual outcome of the particular subject or set of subjects is obtained, it is compared to the predicted outcome given by the PC system the system is re-trained. In further embodiments, a AL/ND system functions as a "filtering" or "alerting" mechanism and determines a) whether the data of the particular subject or set of subjects are "novel," in the sense that the PC system will provide unreliable predictions for the particular data b) what emerging data are optimal for re-training and updating the PC system, and therefore should be added to the TS.

a) In some embodiments, a NLP system is used to process EHRs and CNs where applicable, i.e., where data are in unstructured form. In further embodiments, a NLP systems extracts, in a systematic way, information such as "concepts," "named entities," or any other useful information is embedded in the free text. In still further embodiments, such information is used to augment the set of inputs of the PC. In some embodiments, key words or general-case specific context, found in or derived from EHRs or CNs, are deemed as important in predicting a probabilistic outcome for a subject or set of subjects, are added to the input set of the PC system. For instance, expressions in clinical notes such as "intense chest pain" will bear more/different weight in cardiac related scenarios than in different situations. In various embodiments, a NLP system uses both a supervised and an unsupervised approach to learning from EMRs and CNs. In some embodiments, a supervised approach is driven by some outcome variable, and the learning is optimized to predict that outcome variable. In some embodiments, an unsupervised approach is used when the learning is not taking place to optimize any outcome variable, but rather to identify patterns or "clusters" in the training data, serving as the guide for finding "latent" or "hidden" concepts in the TS. In various embodiments, the system uses one of the following methods to achieve optimal feature or concept extraction that the PC system invokes:

Supervised Approach
1) Conditional random fields
2) Hidden Markov models
3) Syntactic parsing (serving as a preprocessing step)
4) Lemmatization of words Unsupervised Approach
1) Latent Dirichlet allocation models
2) Distributional semantic clustering
3) Latent semantic indexing In some embodiments, at least one of the methods above will be used to achieve accurate identification of key clinical concepts.

b) In some embodiments, a statistical classifier or PC system uses information obtained by as described above as well as by structured and tab delimited type data to determine a risk outcome for the particular subject or set of subjects. In further embodiments, such data includes, but is not limited, to vital signs, ICD9 diagnoses, laboratory test reports, medical histories, demographic characteristics, assessments, treatments, prescriptions and plans, etc. In some embodiments, a PC system is based on a single yet powerful classification method and an "enhancement method" is used to improve its predictive performance, after the simple method has been determined. In further embodiments, a PC system uses at least one of the following classification methods:

1) A nearest neighbor classifier
2) A classification tree
3) An additive logistic model
4) Multivariate adaptive regression splines
5) A support vector machine
6) A neural network
7) A graphical model
8) A model free system
9) A random forest In some embodiments, the optimal choice of the parameters for each of the above single classifiers will be based on at least one of the following selection criteria:

1) Akaike Information Criterion (AIC), Bayesian Information criterion (BIC), a deviance measure, an impurity measure such as a Gini coefficient, a miss-classification error measure, an exponential loss measure, or a binomial log-likelihood loss measure
2) A cross-validation set and a test set
3) A bagging
4) A bootstrap procedure In some embodiments, once the final classifier is obtained, at least one/or a combination of the following "enhancement" algorithms are used to optimize predictive performance, where applicable:

1) Adaboost
2) Gradient noosting
3) Stochastic gradient boosting
4) Stacking
5) A Bayesian model averaging
6) Query by committee c) In some embodiments, an AL/ND is used to detect "novel" data that are likely to provide false predictions or likely to affect the performance of the system after they are entered into the TS and the system is re-trained. Also, in further embodiments, the AL/ND system is used when computations are expensive, or the outcomes variables (especially those needed for training the NLP system), are very expensive or for some reason cannot be obtained. In some embodiments, once such data are detected, the client is notified, and new/different information is requested for predictions. Finally, in some embodiments, the system performs optimal "experimental design" and "chooses" data that are most informative for training the NLP and PC systems. In some embodiments, the AL/ND system uses one of the following methods:

1) A k-means/hierarchical/spectral clustering algorithm to detect large "distances" from the "good" data.
2) A principal, factor or independent component analysis.
3) A manifold learning method such as ISOMAP, Laplacian Eigenmaps, or Local Linear Embedding
4) A Kernel principal component analysis
5) One class support vector machine or an "new" support vector machine method
6) Any other expert heuristic method determined in practice In some embodiments, the architecture of a CMD machine is based on the paradigm that all the technologies outlined above are developed and custom-tailored in-house. In further embodiments, once a re-training is decided, all the models/ algorithms are re-trained and the model achieving the best success criterion during the last training session is used for the prediction of the presented "unknown" data. Those of skill in the art will recognize that parallel computing is optionally implemented for optimization of computational time.

In some embodiments, in addition to predicting risks of mortality and morbidity, a CMD machine also provides recommendation of treatments for the particular case. The concept of the Recommendation System (RS) is based on a "reinforcement learning" paradigm. The system provides recommendations that "maximize" or "minimize" some criterion (e.g., risk of mortality). The system will make use of one the following methods:

1) Q-learning algorithm
2) Temporal difference learning
3) Some other expert heuristic technique In alternative embodiments, a RS takes the form of a "collaborative filtering" problem where it recommends treatments that had positive outcomes for patients with similar symptoms. In further embodiments, a RS can be either memory or model based. In the case of the former, some similarity type of algorithm is used, such as the following:

1) A correlation measure
2) A clustering approach
3) A nearest neighbor algorithm
4) Some other heuristic technique In the case of the latter, some model-based algorithm similar to those described in herein is used.

In some embodiments, the module for applying a diagnostic or therapeutic analysis predicts an acute risk minute-by-minute with and without one or more specified therapies. In further embodiments, the diagnostic or therapeutic analysis comprises predicting acute risks, with and without one or more potential therapies, based on the severity of a condition and risks associated with each potential therapy to determine the intensity of therapy recommended.

In some embodiments, a prediction of acute risk is updated at pre-configured time intervals. In some embodiments, a prediction of acute risk is updated at time intervals selected by a live healthcare provider. In some embodiments, a prediction of acute risk is updated at time intervals selected based on, for example, the type of complaint, subject history, severity of illness, and the like, including combinations thereof. In various further embodiments, suitable time intervals for updating a prediction of acute risk include, by way of non-limiting example, about 96 hours, about 72 hours, about 48 hours, about 24 hours, about 12 hours, about 6 hours, about 4 hours, about 2 hours, about 1 hour, about 45 minutes, about 30 minutes, about 15 minutes, about 10 minutes, about 5 minutes, about 1 minute, about 45 seconds, about 30 seconds, about 15 seconds, about 10 seconds, about 5 seconds, and about 1 second, or less, including increments therein. In various embodiments, suitable time intervals for updating a prediction of acute risk include, by way of non-limiting example, about 96 hours to about 72 hours, about 72 hours to about 48 hours, about 48 hours to about 24 hours, about 24 hours to about 12 hours, about 12 hours to about 6 hours, about 6 hours to about 4 hours, about 4 hours to about 2 hours, about 2 hours to about 1 hour, about 1 hour to about 45 minutes, about 45 minutes to about 30 minutes, about 30 minutes to about 15 minutes, about 15 minutes to about 10 minutes, about 10 minutes to about 5 minutes, about 5 minutes to about 1 minute, about 1 minute to about 45 seconds, about 45 seconds to about 30 seconds, about 30 seconds to about 15 seconds, about 15 seconds to about 10 seconds, about 10 seconds to about 5 seconds, about 5 seconds to about 1 second, about 1000 milliseconds to about 100 milliseconds, about 100 milliseconds to about 10 milliseconds, and about 10 milliseconds to about 1 millisecond, including increments therein.

In some embodiments, a prediction of acute risks is made for a pre-configured time period. In some embodiments, a prediction of acute risks is made for a time period selected by a live healthcare provider. In some embodiments, a prediction of acute risks is made for a time period based on, for example, the type of complaint, subject history, severity of condition, and the like. In various further embodiments, suitable time intervals for updating a prediction of acute risk include, by way of non-limiting example, less than about 96 hours, less than about 72 hours, less than about 48 hours, less than about 24 hours, less than about 12 hours, less than about 8 hours, less than about 6 hours, less than about 4 hours, less than about 2 hours, and less than about 1 hour, less than about 30 minutes, less than about 15 minutes, less than about 5 minutes, less than about 1 minute, less than about 30 seconds, less than about 15 seconds, less than about 5 seconds, less than about 1 second, less than about 500 milliseconds, less than about 100 milliseconds, less than about 10 milliseconds, and less than about 1 millisecond, including increments therein. In various further embodiments, suitable time intervals for updating a prediction of acute risk include, by way of non-limiting example, about 96 hours to about 72 hours, about 72 hours to about 48 hours, about 48 hours to about 24 hours, about 24 hours to about 12 hours, about 12 hours to about 6 hours, about 6 hours to about 4 hours, about 4 hours to about 2 hours, about 2 hours to about 1 hour, about 1 hour to about 45 minutes, about 45 minutes to about 30 minutes, about 30 minutes to about 15 minutes, about 15 minutes to about 10 minutes, about 10 minutes to about 5 minutes, about 5 minutes to about 1 minute, about 1 minute to about 45 seconds, about 45 seconds to about 30 seconds, about 30 seconds to about 15 seconds, about 15 seconds to about 10 seconds, about 10 seconds to about 5 seconds, about 5 seconds to about 1 second, about 1000 milliseconds to about 100 milliseconds, about 100 milliseconds to about 10 milliseconds, and about 10 milliseconds to about 1 millisecond, including increments therein.

In some embodiments, the module for applying a diagnostic or therapeutic analysis predicts health or economic outcomes and/or predicts acute risk minute-by-minute and issues one or more explanations of the risks predicted and/or methods used to predict the risks. In some embodiments, the module for applying a diagnostic or therapeutic analysis predicts health or economic outcomes and/or predicts acute risk minute-by-minute and issues one or more disclaimers regarding the accuracy of the risks predicted, likelihood of the risks predicted, and/or methods used to predict the risks.

In various embodiments, the module for applying a diagnostic or therapeutic analysis recommends a wide variety of intensities of therapy. For example in some embodiments, the module recommends triage to a lower level of care (e.g., self-care, bed rest, oral hydration, etc.), performing a diagnostic procedure utilizing one or more biosensors (e.g., HD video camera, blood pressure monitor, blood glucose monitor, ECG, ultrasound, auscultation probe, etc.), dispensing a medical item for the subject (e.g., dietary supplement, OTC medication, prescription medication, diagnostic device, diagnostic kit, therapeutic device, etc.), triage to a higher level of care (e.g., inpatient admission, etc.), or automated call to an emergency response system (e.g., 911, etc.) with subject information and location.

Figure 24:
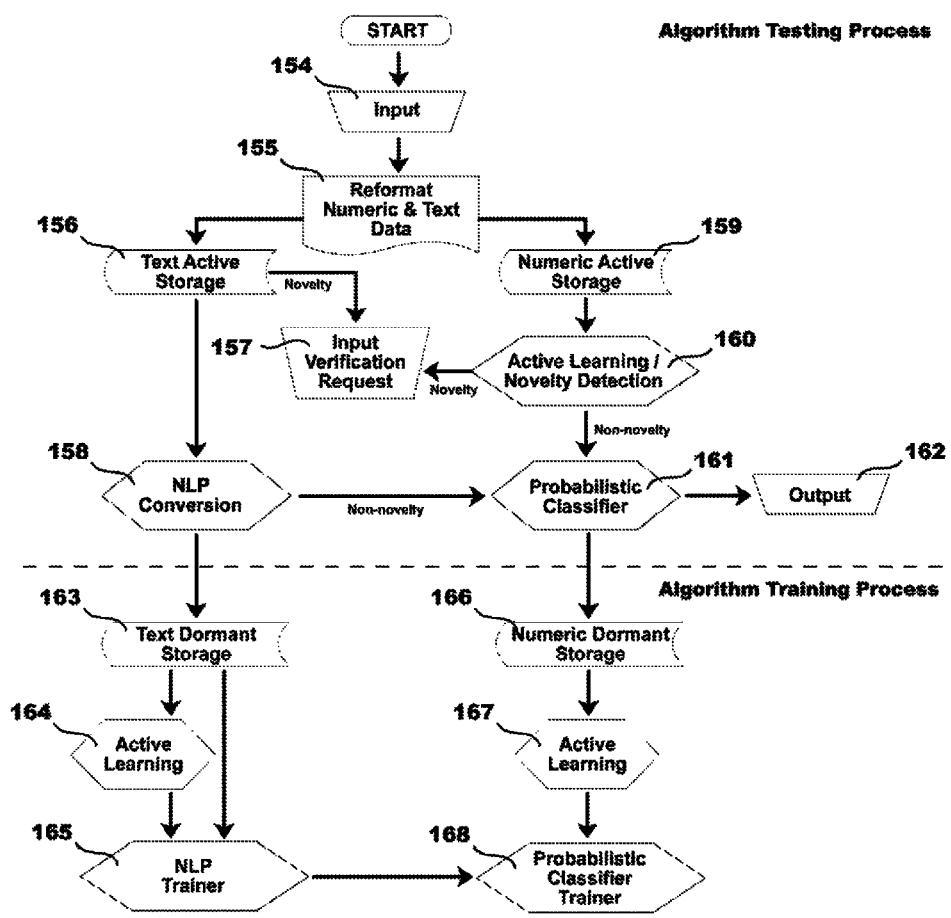
FIG. 24 shows a non-limiting exemplary process flow for predicting a risk of mortality and/or morbidity; in this case, a process employing natural language processing and machine learning.

Referring to FIG. 24, in a particular embodiment, a module for applying a diagnostic or therapeutic analysis predicts a risk of mortality and/or morbidity for one or more subjects. In some embodiments, a module for applying a diagnostic or therapeutic analysis includes an on demand algorithm testing process and a continual algorithm training process. In some embodiments, an algorithm testing process starts with input data 154. In various embodiments, input is for one subject or a plurality of subjects. Any type of data is suitable including, by way of non-limiting embodiments, textual data, tabular data, numeric data, and the like. In some embodiments, after input, data is reformatted and text and numeric data separated 155. In light of the disclosure provided herein, those of skill in the art will recognize that some programming languages and applications offer features making them more useful for manipulating particular data types. Next, text (e.g., any data from which natural language can be derived including text, audio, or video) is moved to text active storage 156. Active storage includes data currently in process for which outcomes are not yet assigned. In some embodiments, if text data is novel to the system, more information is requested. In further embodiments, input verification 157 involves checking data for errors and correcting errors in data or data formatting. In some embodiments, if text data is not novel to the system it is subjected to natural language processing conversion 158. In further embodiments, variables are extracted from language using elements of machine learning. Once all data is converted to numbers, the data is subjected to a set of algorithms in a probabilistic classifier 161. In some embodiments, the result is output 162 in the form of a percentage or other expression of risk of mortality and/or morbidity. In some embodiments, this process is repeated and refined continually to produce a minute-by-minute prediction.

Continuing to refer to FIG. 24, in a particular embodiment, numeric data is moved to numeric active storage 159. In further embodiments, numeric data is a file. In other embodiments, numeric data is a plurality of files. In various embodiments, numeric data is formatted as, for example, CSV, tab delimited, a database, etc. In some embodiments, if numeric data is novel to the system, more information is requested. In further embodiments, input verification 157 involves checking data for errors and correcting errors in data or data formatting. In some embodiments, if numeric data is not novel to the system it is subjected to a set of algorithms in a probabilistic classifier 161 resulting in the same output 162.

Continuing to refer to FIG. 24, in a particular embodiment, a module for applying a diagnostic or therapeutic analysis includes a continual algorithm training process. In some embodiments, in an algorithm training process text data from natural language processing conversion 158 is moved to text dormant storage 163. Unlike active storage, dormant storage includes data not actively in the process and for which outcomes are attached. From dormant storage, an active learning process 164 determines which data are most valuable in reaching accurate predictions in order to make future predictions more efficient and accurate. This information is fed into a natural language trainer 165.

Continuing to refer to FIG. 24, similarly in some embodiments, in an algorithm training process numeric data from a probabilistic classifier 161 is moved to numeric dormant storage 166. From dormant storage, an active learning process 167 determines which data are most valuable in reaching accurate predictions in order to make future predictions more efficient and accurate. This information is fed into a probabilistic classifier trainer 168.

In another particular embodiment, a module for applying a diagnostic or therapeutic analysis operates under a "SOAPO structure" described herein with the overall goal of replicating a physician's decision making process. In this embodiment, SOAPO stands for Subjective, Objective, Assessment, Plan, and Outcomes, each is described further herein. In further embodiments, a module for applying a diagnostic or therapeutic analysis utilizes the following process:

First, given the Subjective and Objective information of a subject (e.g., inputs), the module generates the Assessment based on models that are trained on a wide variety of data.

Second, based on the Subjective, Objective, and Assessment patient inputs, Plans of treatment are generated.

Third, an associated risk for each proposed treatment is generated.

Finally, the statistical models utilized by the system are trained regularly (using methods described herein) to ensure an accurate and up-to-date system. In light of the disclosure provided herein, those of skill in the art will recognize that this step is important because training determines overall predictive performance.

Subjective

In some embodiments, subjective input includes a subject's chief complaint. In further embodiments, a chief complaint is a brief statement of the subject as to the purpose of a request for care. In still further embodiments, a chief complaint describes the subject's current condition in narrative form. For example, the history and/or state of symptoms experienced by the subject are recorded in the subject's own words. In some embodiments, a chief complaint includes, by way of non-limiting examples, all pertinent and negative symptoms under review of body systems, pertinent medical history, surgical history, family history, social history, current medications, and allergies.

Objective

In some embodiments, objective input includes a subject's vital signs and measurements, such as weight and Body Mass Index (BMI). In further embodiments, objective input includes findings from physical examinations and lab tests.

Assessment

In some embodiments, an assessment includes is a differential diagnosis, namely, a list of possible diagnoses usually in order of most likely to least likely.

Plan

In some embodiments, a plan includes list of recommended treatment plans given the assessment of a subject's condition. In further embodiments, recommended treatment plans include, by way of non-limiting examples, ordering further labs, ordered radiological work, referrals, performed procedures, and medications. In still further embodiments, a recommended treatment plan addresses each item of the differential diagnosis.

Figure 25:
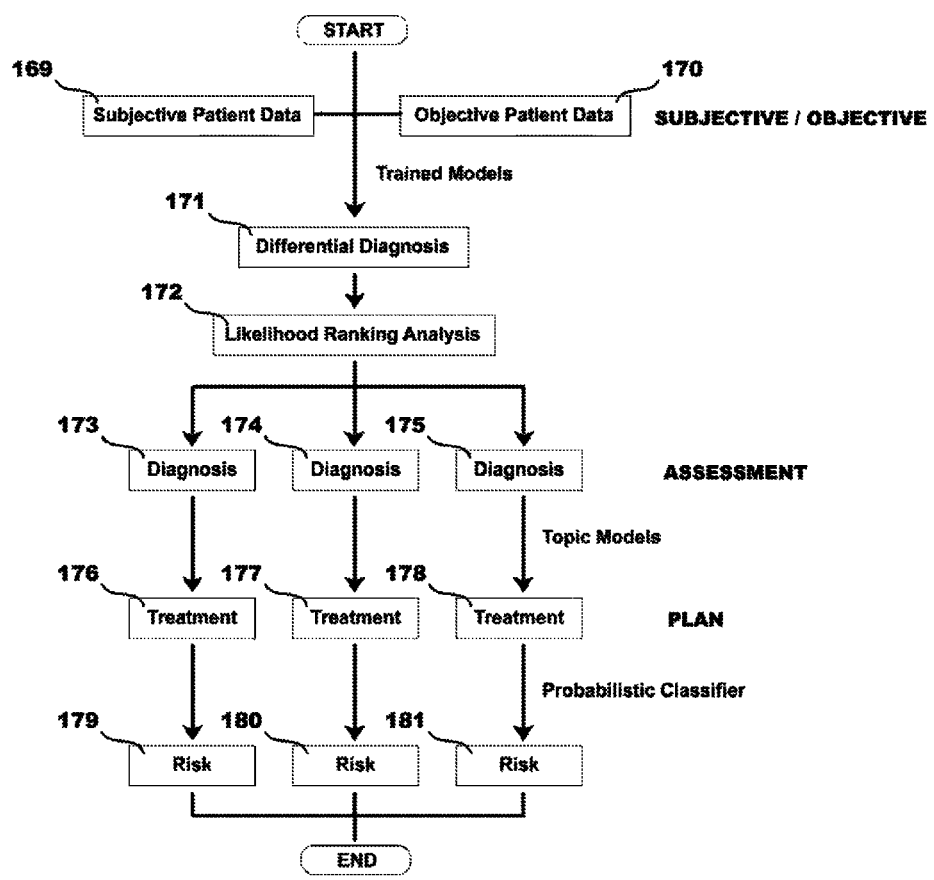
FIG. 25 shows a non-limiting exemplary process flow for applying a diagnostic and therapeutic analysis; in this case, a process replicating a typical healthcare decision making process involving making a differential diagnosis, proposing at least one treatment to address each potential diagnosis, and assessing risk of an adverse outcome with and without each potential treatment.

Referring to FIG. 25, in a particular embodiment, a module for applying a diagnostic or therapeutic analysis accepts subjective 169 and objective 170 subject inputs. Trained statistical models extract a differential diagnosis 171. In some embodiments, a NLP approach is utilized, wherein statistical models are trained on large databases of specialized medical information written in natural language (e.g., medical literature, web sites, etc.) to extract differential diagnoses 171 based on the assumption that symptoms and diagnoses coexist in such databases. In further embodiments, supervised or unsupervised Latent Dirichlet Allocation (LDA) models are utilized to extract differential diagnoses 171. In other embodiments, conditional random fields (CRF), hidden Markov models (HMM), or deep learning methods, such as multilayer neural networks, convolutional neural networks, and the like, are used to extract differential diagnoses. Further, in this embodiment, extracted diagnoses are ranked 172 by likelihood.

Continuing to refer to FIG. 25, for each extracted diagnosis 173, 174, 175 a plan of treatment 176, 177, 178, learned by similar methods, is proposed. Finally, a probabilistic classifier predicts a risk of an adverse outcome 179, 180, 181 for each proposed treatment.

Medical Items

In some embodiments, disclosed herein are systems and devices comprising an apparatus for dispensing one or more medical items and methods of using the same. In some embodiments, the medical items are dispensed to a subject as described herein. In other embodiments, the medical items are dispensed to a caregiver, medical representative, guardian, or legal representative of a subject.

In some embodiments, the apparatus for dispensing medical items is in the same location as the subject for whom items are intended and the items are dispensed directly to the subject or an appropriate caregiver. In other embodiments, the apparatus for dispensing medical items is in a different location from the subject for whom items are intended and the items are dispensed remotely for the subject.

In some embodiments, the medical items are dispensed singly or individually. In other embodiments, the medical items are dispensed in limited numbers. In further embodiments, the medical items are dispensed loose, unpackaged, or in a temporary package such as a cup, tray, box, or envelope. In still other embodiments, the medical items are dispensed in bulk.

In some embodiments, the medical items are pre-packaged. In further embodiments, pre-packaged medical items are sealed in a container (e.g., a package) prior to introduction to the dispensing apparatus. In other embodiments, pre-packaged medical items are sealed in a container (e.g., a package) prior to dispensing. In further embodiments, the container has a sterile interior. In further embodiments, the container is designed to prevent opening by a child (e.g., child-resistant). Many containers are suitable for the medical items and include, by way of non-limiting examples, bottles, blister packaging, boxes, envelopes, and the like, each composed of one or more of several suitable materials that include, for example, plastic, foil, paper, cardstock, cardboard, Mylar, and the like. In some embodiments, a container (e.g., a package) includes printed text. In further embodiments, the text is printed directly on the container. In other embodiments, the text is printed on a label that is applied to the container. In various embodiments, the printed text indicates, by way of non-limiting examples, the nature of the medical item or items, the identity of the items, the number of items, the use of the items, instructions for use, warnings, and the like. In various further embodiments, where the medical item is a prescription or non-prescription pharmaceutical, the printed text indicates, by way of non-limiting examples, drug name, dosage, expiration date, lot number, and the like. In various further embodiments, the printed text is customized and indicates, by way of non-limiting examples, the name of the subject, the address of the subject, the name of the prescribing professional or entity, and the address of the prescribing professional or entity, and the like. In some embodiments, the printed text is supplemented by graphics, photographs, or pictograms indicating the same.

In some embodiments, the inventory of medical items is risk profiled to a particular subject, population, venue, situation, or a combination thereof. In further embodiments, the inventory of medical items is determined by profiling health and/or economic risk for a subject or a population in advance of need for said medical items. In still further embodiments, software for applying a diagnostic or a therapeutic analysis disclosed herein is utilized to predict health or economic outcomes for a subject, a population, a venue, a situation, or a combination thereof in order to determine a risk profiled inventory of medical items. In some embodiments, the inventory of medical items is determined by performing a diagnostic or therapeutic analysis for a subject, a family, a population, a venue, a situation, or a combination thereof. In further embodiments, the inventory of medical items is determined by performing statistical analysis, performing probability calculations, making recommendations, and making outcome predictions to predict a health or economic outcome of a patient or therapy, wherein said prediction is real-time, individualized, and probabilistic-based and uses historic, peer-reviewed health or economic data and emerging health or economic data. In some embodiments, the inventory of medical items is determined by performing a diagnostic or therapeutic analysis for a subject, a family, a population, a venue, a situation, or a combination thereof. In further embodiments, the inventory of medical items is determined by predicting acute risks, with and without one or more potential therapies, based on the severity of a condition and risks associated with each potential therapy to determine the intensity of therapy recommended.

In certain embodiments where an inventory of medical items is risk profiled to a particular subject, the inventory is determined by predicting future health and/or economic risks to the subject. In further embodiments, the inventory comprises or is enriched with medical items selected for their potential utility to the subject. In still further embodiments, the inventory comprises medical items not currently utilized by the subject. In some embodiments, the medical items are pre-prescribed to the subject as PRN (i.e., pro re nata, meaning "as needed") medications. In certain embodiments where an inventory of medical items is risk profiled to a particular family, the inventory is determined by predicting future health and/or economic risks to the members of the family. In further embodiments, the inventory comprises or is enriched with medical items selected for their potential utility to the members of the family. In still further embodiments, the inventory comprises medical items not currently utilized by any member of the family. In some embodiments, the medical items are pre-prescribed to the one or more members of the family as PRN (i.e., pro re nata, meaning "as needed") medications. In certain embodiments where an inventory of medical items is risk profiled to a particular population of subjects, the inventory is determined by predicting future health and/or economic risks to the population of subjects. In further embodiments, the inventory comprises or is enriched with medical items selected for their potential utility to the population. In certain embodiments where an inventory of medical items is risk profiled to a particular venue or location, the inventory is determined by predicting future health and/or economic risks to individuals present at the venue or location. In further embodiments, the inventory comprises or is enriched with medical items selected for their potential utility to individuals present at the venue or location. In certain embodiments where an inventory of medical items is risk profiled to a particular situation or circumstance, the inventory is determined by predicting future health and/or economic risks to individuals in the situation or circumstance.

In some embodiments, the inventory of medical items is delivered before it is needed based on anticipated need. In further embodiments, anticipated need is based on statistical level of likelihood that the items will be needed in the short-term future. In further various embodiments, anticipated need is based on statistical level of likelihood that the items will be needed within, by way of non-limiting examples, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more days, including increments therein. In further various embodiments, anticipated need is based on statistical level of likelihood that the items will be needed within, by way of non-limiting examples, 1, 2, 3, 4, 5, 6, 7, 8, 9, 10, 11, 12, 13, 14, 15, 16, 17, 18, 19, 20, 21, 22, 23, 24 or more months, including increments therein. In some embodiments, ahead in time delivery enables the systems, devices, and methods described herein to provide real in time therapy.

Many types of medical items are suitable for dispensing to the subjects described herein. In various embodiments, the medical items include, by way of non-limiting examples, vitamins, minerals, dietary supplements, herbal remedies, over-the-counter medications, prescription medications, therapeutic devices, diagnostic devices, diagnostic kits, and educational materials.

In some embodiments, medical items include one or more vitamin supplement. In various further embodiments, suitable vitamin supplements include vitamin A (e.g., retinol), vitamin B1 (e.g., thiamine), vitamin B12 (e.g., cyanocobalamin, hydroxycobalamin, and methylcobalamin), vitamin B2 (e.g., riboflavin), vitamin B3 (e.g., niacin and niacinamide), vitamin B5 (e.g., pantothenic acid), vitamin B6 (e.g., pyridoxine, pyridoxamine, and pyridoxal), vitamin B7 (e.g., biotin), vitamin B9 (e.g., folic acid), vitamin C (e.g., ascorbic acid), vitamin D (e.g., cholecalciferol), vitamin E (e.g., tocopherols and tocotrienols), and vitamin K.

In some embodiments, medical items include one or more mineral supplement. In various further embodiments, suitable mineral supplements include, by way of non-limiting examples, calcium, chromium, iodine, iron, magnesium, phosphorus, potassium, selenium, and zinc.

In some embodiments, medical items include one or more dietary supplement. In various further embodiments, suitable dietary supplements include, by way of non-limiting examples, enzymes, herbs, and amino acids.

In some embodiments, medical items include one or more herbal remedies. In various further embodiments, suitable herbal remedies include, by way of non-limiting examples, Açai (*Euterpe oleracea*), Alfalfa (*Medicago sativa*), Aloe vera, Arnica (*Arnica montana*), Asthma weed (*Euphorbia hirta*), Astragalus (*Astragalus propinquus*), Barberry (*Berberis vulgaris*), Belladonna (*Atropa belladonna*), Bilberry (*Vaccinium myrtillus*), Bitter leaf (*Vernonia amygdalina*), Black cohosh (*Actaea racemosa*), Blessed thistle (*Cnicus benedictus*), Burdock (*Arctium lappa*), Cat's claw (*Uncaria tomentosa*), Cayenne (*Capsicum annuum*), Celery (*Apium graveolens*), Chamomille (*Matricaria recutita* and *Anthemis nobilis*), Chaparral (*Larrea tridentata*), Chasteberry (*Vitex agnus-castus*), Chili (*Capsicum frutescens*), Coffee senna (*Cassia occidentalis*), Comfrey (*Symphytum officinale*), Cranberry (*Vaccinium macrocarpon*), Dandelion (*Taraxacum officinale*), Digitalis (*Digitalis lanata*), Dong quai (*Angelica sinensis*), Elderberry (*Sambucus nigra*), Ephedra (*Ephedra sinica*), Eucalyptus (*Eucalyptus globulus*), European Mistletoe (*Viscum album*), Evening primrose (*Oenothera* species), Fenugreek (*Trigonella foenum-graecum*), Feverfew (*Tanacetum parthenium*), Flaxseed (*Linum usitatissimum*), Garlic (*Allium sativum*), Ginger (*Zingiber officinale*), Gingko (*Gingko biloba*), Ginseng (*Panax ginseng* and *Panax quinquefolius*), Goldenseal (*Hydrastis canadensis*), Guava (*Psidium guajava*), Hawthorn (*Crataegus laevigata*), Hoodia (*Hoodia gordonii*), Horse chestnut (*Aesculus hippocastanum*), Horsetail (*Equisetum arvense*), Jamaica dogwood (*Piscidia erythrina* or *Piscidia piscipula*), Kava (*Piper methysticum*), Konjac (*Amorphophallus konjac*), Lavender (*Lavandula angustifolia*), Licorice root (*Glycyrrhiza glabra*), Marigold (*Calendula officinalis*), Marsh mallow (*Althaea officinalis*), Milk thistle (*Silybum marianum*), Neem (*Azadirachta indica*), Noni (*Morinda citrifolia*), Papaya (*Carica papaya*), Peppermint (*Mentha* x *piperita*), Purple coneflower (*Echinacea purpurea*), Red clover (*Trifolium pratense*), Sage (*Salvia officinalis*), St. John's wort (*Hypericum perforatum*), Saw palmetto (*Serenoa repens*), Tea tree oil (*Melaleuca alternifolia*), Thunder God Vine (*Tripterygium wilfordii*), Turmeric (*Curcuma longa*), Valerian (*Valeriana officinalis*), White willow (*Salix alba*), Yerba santa (*Eriodictyon crassifolium*), and Yohimbe (*Pausinystalia yohimbe*).

In some embodiments, medical items include one or more medications. In further embodiments, the medical items include common medications such as insulin, oral hypoglycemics, diuretics, potassium, antibiotics, ACE inhibitors, other anti-hypertensives, anti-arrhythmics, anti-coagulants, anti-inflammatories, analgesics, oral vaccines, injectable vaccines, bronchodilators, steroids, and oxygen.

In some embodiments, medications include one or more over-the-counter (OTC) medications. OTC medications are those that may be sold directly to a consumer without a prescription from a healthcare professional. In further embodiments, OTC medications include, by way of non-limiting examples, allergy prevention treatment medications, antacid medications, anticandial medications, antihistamines, antidiarrheal medications, anti-fungal medications, anti-itch lotions and creams, asthma medications, cold sore/fever blister medications, contact lens solutions, cough suppressants, decongestants, nasal decongestant and cold remedies, diaper rash ointments, eye drops for allergy or cold relief, first aid supplies, hemorrhoid treatments, internal analgesics and antipyretics, liniments, menstrual cycle medications, migraine medications, motion sickness medications, nicotine gum or patches and smoking cessation aids, pediculicides, poison ivy protection medications, toothache and teething pain medications, and wart removal medications, not requiring a valid prescription.

In some embodiments, medications include one or more prescription medications. Prescription medications are those that may be sold only to consumers possessing a valid prescription. In some embodiments, a valid prescription is issued by a Doctor of Medicine (MD), Doctor of Osteopathic Medicine (DO), Physician Assistant (PA), Doctor of Optometry (OD), Doctor of Podiatry (DPM), Doctor of Naturopathic Medicine (NMD or ND), Doctor of Veterinary Medicine (DVM), Doctor of Dental Surgery (DDS), Doctor of Dental Medicine (DMD), Medical Psychologist, Nurse Practitioner (NP) or other Advance Practice Nurse. In further embodiments, prescription medications include, by way of non-limiting examples, ADHD medications, antacid medications (e.g., proton pump inhibitors), antibiotics, anticoagulants, antifungals, antipsychotics, antivirals, asthma and COPD medications, cholesterol-lowering medications (e.g., statins), contraceptives, depression medications, diabetes medications, erectile dysfunction medications, glaucoma medications, hormone therapy medications, hypertension medications, hypnotics, migraine medications, multiple sclerosis medications, nasal allergy medications, nausea medications, oral allergy medications, osteoporosis medications, overactive bladder medications, pain relief medications, rheumatoid arthritis medications, sedatives, and seizure medications, requiring a valid prescription.

In some embodiments, a live, licensed healthcare provider monitors, supervises, or operates, an apparatus for dispensing one or more medical items. In some embodiments, the live, licensed healthcare provider is a licensed pharmacist. In other embodiments, the live, licensed healthcare provider is in communication with a licensed pharmacist. In further embodiments, the live, licensed healthcare provider is responsible for monitoring, supervising, or operating the apparatus for dispensing medical items uses a software module for telecommunications to contact, conference, or otherwise communicate with a licensed pharmacist. In still further embodiments, the pharmacist assures the accuracy of the prescription and the medical items selected for dispensing to fill the prescription, reviews the prescription for recalls and drug interactions, etc. In some embodiments, the live, licensed healthcare provider is in communication with pharmacy technician supervised by a licensed pharmacist.

In certain embodiments, disclosed herein are systems and devices for providing remote medical diagnosis and therapy to subjects who have an injury or illness that requires immediate care but is not serious enough to warrant a visit to an emergency department. Accordingly, in some embodiments, the medical items are packaged to address the urgent need and contain a short-term supply of, for instance, medication. By way of example, in various embodiments, each package of medication contains less than a two-week supply of medication, less than a one-week supply of medication, less than a four-day supply of medication, and less than a two-day supply of medication.

In some embodiments, the inventory of medical items comprises one or more therapeutic devices. In further embodiments, the therapeutic devices include, by way of non-limiting examples, first aid supplies, hearing aids, optical aids, prostheses, mobility aids, continuous positive airway pressure (CPAP) supplies, and the like. In some embodiments, the therapeutic devices include implements for administering medications such as syringes, needles, inhalers, infusers, and vaporizers.

In some embodiments, the inventory of medical items comprises one or more diagnostic devices. In further embodiments, the diagnostic devices include, by way of non-limiting examples, blood chemistry testing devices, hemoglobin testing devices, hematocrit testing devices, blood glucose testing devices, blood cholesterol testing devices, blood pressure testing devices, heart rate monitors, urinalysis devices, and sexually transmitted disease testing devices. In still further embodiments, the diagnostic devices include disposable parts and consumable supplies for the devices disclosed herein including, by way of non-limiting examples, test strips, reagents, solutions, and the like.

In some embodiments, the inventory of medical items comprises one or more diagnostic kits. In further embodiments, the diagnostic kits include, by way of non-limiting examples, blood chemistry testing kits, hemoglobin testing kits, hematocrit testing kits, blood glucose testing kits, blood cholesterol testing kits, urinalysis kits, and sexually transmitted disease testing kits.

In some embodiments, the medical items are dispensed from an inventory of medical items. The devices disclosed herein, in certain embodiments, vary widely in scale including, for example, portable devices, desktop devices, kiosk devices, and stationary devices, and installations. Accordingly, a wide range of inventory sizes are suitable. In various embodiments, an inventory of medical items includes, by way of non-limiting example, about 1 to about 10, about 10 to about 100, about 100 to about 1,000, about 1,000 to about 10,000, about 10,000 to about 100,000 or more medical items, including increments therein. In various further embodiments, an inventory of medical items includes, by way of non-limiting example, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500 or more types of medical items, including increments therein. In still further various embodiments, an inventory of medical items includes, by way of non-limiting example, 1, 2, 3, 4, 5, 6, 7, 8, 9, 10, 15, 20, 25, 30, 35, 40, 45, 50, 55, 60, 65, 70, 75, 80, 85, 90, 95, 100 or more variations of each medical item in the inventory, including increments therein. In some embodiments, an apparatus for dispensing one or more medical items includes features adapted to facilitate refilling, restocking, or resupplying the medical items or the inventory of medical items.

Remote, Adjunct Healthcare Provision Systems

Disclosed herein, in certain embodiments, are remote healthcare systems for extending patient care effectiveness of a licensed primary healthcare provider facility, group, or individual and providing professional triage services, comprising: a remote adjunct healthcare provider, wherein said adjunct provider is credentialed by said licensed primary healthcare provider facility, group, or individual to provide remote adjunct care for one or more patients, wherein said adjunct provider is covered by medical malpractice insurance, wherein said patients are legally under the care of said licensed primary healthcare provider facility, group, or individual; a software module for providing said remote adjunct healthcare provider access to one or more EHRs for said one or more patients, wherein said EHRs are historic and/or live; and a communications link between said remote adjunct healthcare provider and said patient or one or more onsite patient caregivers. In some embodiments, the system further comprises a communications link between said remote adjunct healthcare provider and one or more pharmaceutical, diagnostic, or therapeutic service providers. In some embodiments, the system further comprises a communications link between said remote adjunct healthcare provider and one or more live medical, legal, insurance, or financial consultants. In some embodiments, credentialing by said licensed primary healthcare provider facility, group, or individual comprises verifying, where applicable, said remote adjunct provider's prescription license, education, training, certifications, professional references, malpractice insurance coverage, malpractice insurance state, legal license to practice their profession, and state of licensure. In some embodiments, credentialing further comprises one or more live interviews. In some embodiments, credentialing by a licensed primary healthcare provider facility, group, or individual comprises granting admitting privileges. In further embodiments, the admitting privileges include billing privileges. In still further embodiments, the admitting privilege includes the right to admit patients to the facility for a specific diagnostic or therapeutic service. In some embodiments, the admitting privilege to a physician is limited to a consultative service. In other embodiments, the admitting privilege is a right granted to a non-physician to treat patients independently with the appropriate state's required oversight and review of the healthcare protocols used by a legally licensed, credentialed physician to empower the non-physician to execute healthcare. In some embodiments, the system further comprises hardware to biometrically verify said patient's identity. In further embodiments, the system further comprises a software module to biometrically verify said patient's identity. In some embodiments, the remote adjunct care is initiated by said patient, by said onsite patient caregivers, or by said licensed primary healthcare provider facility, group, or individual. In some embodiments, the system further comprises a software module for electronically recording all communications between said remote adjunct healthcare provider and said patient and/or said onsite patient caregivers. In some embodiments, the system further comprises a software module for prediction of a health outcome of a patient or therapy, wherein said prediction is real-time, individualized, and probabilistic-based and uses emerging health data, wherein said software module is adapted for use by said remote adjunct healthcare provider. In further embodiments, said emerging health data includes one or more of: patient-specific severity of illness, provider-specific intensity of service, outcome records for healthcare services provided, and third party data. In some embodiments, said prediction of a health outcome of a patient or therapy includes determination of triage level, determination or specific care required, or determination of a particular healthcare provider that is suited to provide said care. In some embodiments, the system further comprises a software module for prediction of an economic outcome of a patient or therapy, wherein said prediction is real-time, individualized, and probabilistic-based and uses emerging economic data, wherein said software module is adapted for use by said remote adjunct healthcare provider. In further embodiments, said module for prediction of a health or economic outcome suggests a prescription, a therapy, an evaluation, or a referral to a specified type of primary care provider, specialist, or ancillary medical personnel. In still further embodiments, said module for prediction of a health or economic outcome recommends a timeline for carrying out said prescription, therapy, evaluation, or referral. In some embodiments, the remote adjunct healthcare provider is a physician. In other embodiments, the remote adjunct healthcare provider is a non-physician. In further embodiments, the remote adjunct healthcare provider is one or more of the following: a dentist, a physician assistant, a nurse practitioner, a registered nurse, a pharmacist, a chiropractor, an emergency medical technician, a licensed practical nurse, a certified ultrasound technician, a psychologist, a social worker, a military medic, a physical therapist, an occupational therapist, a speech therapist, a radiology technician, a cardiac catheterization technician, a clinical pathology laboratory technician, a medical aesthetician, a licensed medical technologist, a toxicologist consultant, a credentialed medical legal consultant, and a credentialed hospital operations administrator. In some embodiments, the remote adjunct healthcare provider is identified or selected based on one or more of: type of a patient's condition, severity of a patient's condition, a patient's insurance eligibility, or availability of one or more remote adjunct healthcare providers. In some embodiments, the patient is admitted to the healthcare facility. In other embodiments, the patient is not admitted to the healthcare facility. In some embodiments, the remote care, answering, and/or professional triage services are provided in a real-time. In other embodiments, the remote care, answering, and/or professional triage services are provided after a time delay. In some embodiments, the patient authorizes the provider's access to their EHRs. In further embodiments, the authorization meets applicable legal requirements. In still further embodiments, said applicable legal requirement is the Health Insurance Portability and Accountability Act of 1996 and/or The Health Information Technology for Economic and Clinical Health Act of 2009. In some embodiments, the software module for providing said remote adjunct healthcare provider access to one or more EHRs further verifies the remote healthcare provider's identity. In some embodiments, said EHRs are updated by the provider. In some embodiments, the EHRs are live, being generated by an onsite patient caregiver, wherein said observer is present with said patient. In further embodiments, the onsite patient caregiver measures one or more of the patient's vital signs or other biometrics. In still further embodiments, the vital sign or biometric comprises at least one of: body temperature, heart rate, blood pressure, respiratory rate, blood diagnostics such as oxygen saturation, glucose concentration, and blood count, urine diagnostics such as specific gravity, protein, glucose, and blood, other bodily fluid diagnostics, and a diagnostic image or imaging report. In some embodiments, the EHRs are generated by an electronic device, wherein said device is present with the patient. In further embodiments, the electronic device measures one or more of the patient's vital signs or other biometrics. In still further embodiments, the vital sign or biometric comprises at least one of: body temperature, heart rate, blood pressure, respiratory rate, blood diagnostics such as oxygen saturation, glucose concentration, and blood count, urine diagnostics such as specific gravity, protein, glucose, and blood, other bodily fluid diagnostics, and a diagnostic image or imaging report. In some embodiments, the electronic device is a biometric sensor. In other embodiments, the electronic device is a portable imaging device. In other embodiments, the electronic device is a portable auscultation device. In some embodiments, the EHRs comprise at least one of: medical history, medication record, medication history, authenticated physical exam, laboratory test reports, imaging reports, demographics, family history, allergies, adverse drug reactions, illnesses, chronic diseases, hospitalizations, surgeries, immunization status, vital signs, age, weight, Observations of Daily Living (ODLs), insurance benefits, insurance, eligibility, insurance claim information, and billing information. In further embodiments, the EHR includes a laboratory test report comprising at least one of: a pathology report, a blood cell count report, a blood culture report, a urinalysis report, a throat culture report, and a genetic test report. In further embodiments, the EHR includes an imaging report comprising at least one of: an X-ray, a CT scan, a MRI, and an ultrasound. In some embodiments, the communication links enable communication via one or more of: telephone, audio conference, video conference, SMS, MMS, instant message, fax, email, and VoIP. In some embodiments, the communication link between the healthcare provider and the service providers meets applicable legal security standards. In further embodiments, the applicable legal standard is the Health Insurance Portability and Accountability Act of 1996 and/or The Health Information Technology for Economic and Clinical Health Act of 2009. In some embodiments, the system further comprises a software module for accessing patient insurance coverage, eligibility, and deductable information or out-of-pocket payment information and information from said one or more pharmaceutical, diagnostic, or therapeutic service providers to guarantee payment to said service provider.

Also disclosed herein, in certain embodiments, are computer-implemented remote healthcare systems for extending patient care effectiveness of a licensed primary healthcare provider facility, group, or individual and providing professional triage services, comprising: a digital processing device connected to a computer network, wherein said processing device comprises a computer readable storage device and an operating system configured to perform executable instructions; and a computer program, provided to said digital processing device, including executable instructions operable to create a remote healthcare application comprising: a software module for verifying credentials of a remote adjunct healthcare provider, wherein said adjunct provider is credentialed by said licensed primary healthcare provider facility, group, or individual to provide remote adjunct care for one or more patients, wherein said adjunct provider is covered by medical malpractice insurance, wherein said patients are legally under the care of said licensed primary healthcare provider facility, group, or individual; a software module for providing said remote adjunct healthcare provider access to one or more EHRs for said one or more patients; wherein said EHRs are historic and/or live; and a software module for creating and maintaining a communications link between said remote adjunct healthcare provider and said patient or one or more onsite patient caregivers.

Also disclosed herein, in certain embodiments, are remote healthcare systems for extending patient care effectiveness of a licensed primary healthcare provider facility, group, or individual and providing professional triage services, comprising: a remote adjunct healthcare provider, wherein said adjunct provider is credentialed by a licensed primary healthcare provider facility, group, or individual to provide remote adjunct care for one or more patients, wherein credentialing by said licensed primary healthcare provider comprises verifying, where applicable, said remote adjunct provider's prescription license, education, training, certifications, professional references, malpractice insurance coverage, malpractice insurance state, legal license to practice their profession, and state of licensure, wherein said patients are legally under the care of said licensed primary healthcare provider facility, group, or individual; a software module for providing said remote adjunct healthcare provider access to one or more EHRs for said one or more patients; wherein at least one record is generated by an onsite patient caregiver or an electronic device present with the patient; and a network or a telephonic link between said remote adjunct healthcare provider and said patient or said onsite patient caregiver. In some embodiments, the healthcare system further comprises a network or a telephonic link between said remote adjunct healthcare provider and one or more pharmaceutical, diagnostic, or therapeutic service providers.

Also disclosed herein, in certain embodiments, are methods for extending patient care effectiveness of a licensed primary healthcare provider facility, group, or individual and providing professional triage services, comprising the steps of: credentialing a remote adjunct healthcare provider to provide remote care for one or more patients, wherein said adjunct provider is credentialed by a licensed primary healthcare provider facility, group, or individual, wherein said adjunct provider is covered by medical malpractice insurance, wherein said patients are legally under the care of said licensed primary healthcare provider facility, group, or individual; and providing said remote adjunct healthcare provider with software to access: one or more EHRs for said one or more patients, wherein said EHRs are historic and/or live; and a communications link to said patients or one or more onsite patient caregivers. In some embodiments, the method further comprises the step of providing said remote adjunct healthcare provider with software to access a communications link to one or more pharmaceutical, diagnostic, or therapeutic service providers. In some embodiments, the method further comprises of providing said remote adjunct healthcare provider with software for prediction of a health outcome of a patient or therapy, wherein said prediction is real-time, individualized, and probabilistic-based and uses emerging health data, wherein said software module is adapted for use by said remote adjunct healthcare provider. In some embodiments, the method further comprises the step of providing said remote adjunct healthcare provider with software for prediction of an economic outcome of a patient or therapy, wherein said prediction is real-time, individualized, and probabilistic-based and uses emerging economic data, wherein said software module is adapted for use by said remote adjunct healthcare provider. In further embodiments, said software for prediction of a health or economic outcome suggests a prescription, a therapy, an evaluation, or a referral to a specialist.

Also disclosed herein, in certain embodiments, are computer readable media encoded with a computer program including instructions executable by the operating system of a networked digital processing device, wherein said instructions create a remote healthcare application, wherein said remote healthcare application comprises: a software module for verifying credentials of a live, remote, adjunct healthcare provider, wherein said adjunct provider is credentialed by said licensed primary healthcare provider facility, group, or individual to provide remote adjunct care for one or more patients, wherein said adjunct provider is covered by medical malpractice insurance, wherein said patients are legally under the care of said licensed primary healthcare provider facility, group, or individual; a software module for providing said remote adjunct healthcare provider access to one or more electronic health records for said one or more patients; wherein said electronic health records are historic and/or live; and a software module for creating and maintaining a communications link between said remote adjunct healthcare provider and said patient or one or more onsite patient caregivers.

Remote Healthcare System

Figure 22:
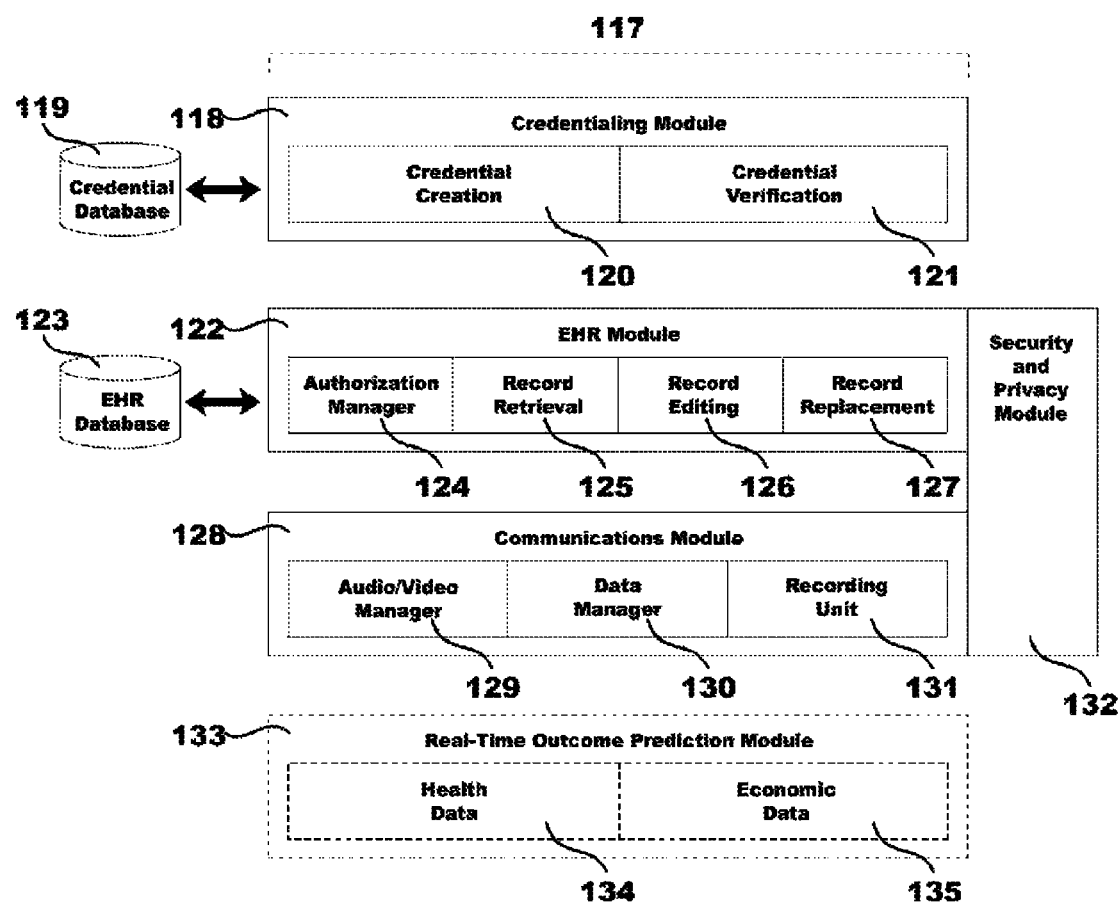
FIG. 22 shows a non-limiting example of a software architecture for a remote, adjunct, credentialed provider-directed healthcare system; in this case, a remote healthcare system including a module for credentialing remote adjunct healthcare providers, a module for providing access to EHRs, a module for providing communications links between the remote adjunct provider and a patient, onsite caregiver, and/or third parties, and a module for maintaining compliance with data security and privacy requirements.

Referring to FIG. 22, in some embodiments, the remote healthcare system 117 comprises a credentialing module 118, an EHR module 122, which is in communication with an EHR database 123, a communications module 128, and a security and privacy module 132. In further embodiments, a credentialing module 118 further comprises sub-modules for credential creation 120 and credential verification 121. In still further embodiments, credentials are stored in and retrieved from a credential database 119, which is in communication with a credentialing module 118. In further embodiments, an EHR module 122 further comprises a sub-module for authorizing access to records 124, which, in some embodiments, verifies the identity of an accessing healthcare provider, a patient, and the legal status of patient authorization. In still further embodiments, an EHR module 122 further comprises a sub-module for retrieving records 125 from an EHR database 123, which is in communication with an EHR module 122 as well as sub-modules for editing 126 and replacing records 127. In some embodiments, an EHR database 123 is internal to the systems described herein. In other embodiments, an EHR database 123 is external and part of a separate electronic healthcare system. In further embodiments, a communications module 128 further comprises sub-modules for managing audio and video content 129 of communications and managing health record data content 130 of communications. In still further embodiments, a communications module 128 further comprises a sub-module for optionally recording communications 131 established and maintained with the systems described herein. In some embodiments, a security and privacy module 132 monitors transactions conducted by an EHR module 122 and a communications module 128 to ensure compliance with data security and patient privacy laws, regulations, and rules. In some embodiments, the system further comprises a real-time outcome prediction module 133, which includes sub-modules for analyzing health data 134 and economic data 135.

Figure 23:
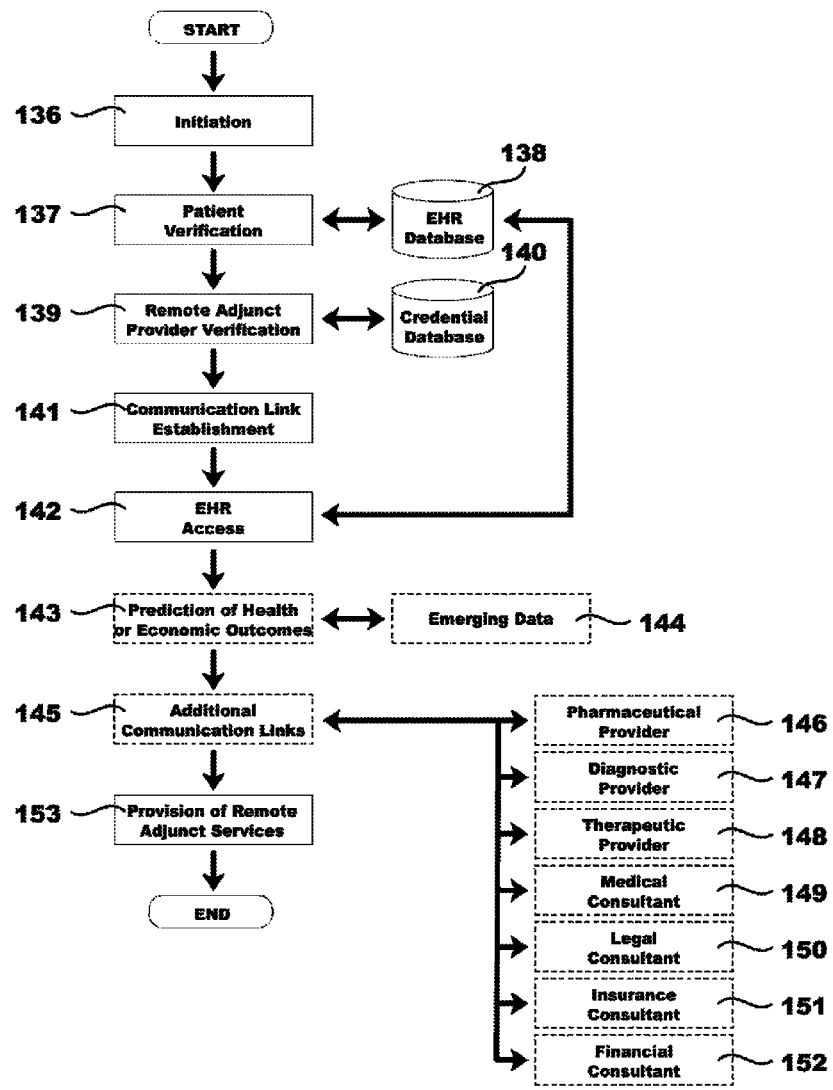
FIG. 23 shows a non-limiting example of a process for utilizing a remote, adjunct, credentialed provider-directed healthcare system such as that exemplified in FIG. 22; in this case, a process including initiation of the system, patient verification, remote adjunct provider verification, access of EHRs, establishment of communications links, and provision of services such as remote care, answering, or triage services.

Referring to FIG. 23, in some embodiments, the remote healthcare system exemplified in FIG. 22 is utilized first by initiation of a contact 136. In further embodiments, the system is initiated by, for example, a patient, an onsite caregiver, or a licensed primary healthcare provider facility, group, or individual. Initiation of the system triggers verification processes. In further embodiments, a patient's identity and legal status of care are verified as suitable 137 by consulting, for example, an EHR database 138. Additionally, in further embodiments, a live, remote adjunct provider's identity and credential status are verified as suitable 139 by consulting a credential database 140. Thereafter, in some embodiments, one or more communications links are established 141 and a live, remote, adjunct healthcare provider accesses one or more EHRs pertaining to a patient 142. In further embodiments, one or more communications links are established with a patient or with an onsite patient caregiver. Optionally, in some embodiments, a live, remote, adjunct healthcare provider engages software to make a real-time, individualized, and probabilistic-based prediction of one or more health or economic outcomes of a patient or therapy 143 using emerging data 144. In further embodiments, emerging health or economic data 144 includes, by way of non-limiting examples, patient-specific severity of illness, provider-specific intensity of service, outcome records for healthcare services provided, and third party data. In some embodiments, additional communications links are established and maintained 145 with, for example, healthcare providers and/or consultants. In further embodiments, additional communications links are established and maintained with, by way of non-limiting examples, pharmaceutical providers 146, diagnostic service providers 147, therapeutic providers 148, medical consultants 149, legal consultants 150, health insurance consultants 151, and financial consultants 152. In some embodiments, use of the system culminates in provision of remote adjunct healthcare services 153 that include, for example, answering services, professional triage services, or extension of patent care effectiveness.

In some embodiments, the systems, products, programs, and methods described herein are for extending patient care effectiveness, professional answering, and triage services. In some embodiments, answering services include receiving and sending communications regarding a patient on behalf of a primary healthcare provider facility, group, or individual, where the patient is legally under the care of the primary provider. In some embodiments, triage services include prioritizing communications regarding patients based on the severity of each patient's condition. In further embodiments, prioritization is conducted so as to address as many communications as possible when resources are such that it is impossible or difficult for all communications to be immediately addressed in a responsible way. In some embodiments, extending patient care effectiveness includes, by way of non-limiting examples, the practices of health care delivery, diagnosis, consultation, treatment, transfer of medical information, and education. In further embodiments, these practices are conducted during the non-working hours of a primary healthcare provider for a particular patient. In further embodiments, these practices are conducted when a primary healthcare provider for a particular patient is sick, busy, on vacation, or otherwise unavailable. In still further embodiments, these practices are conducted using interactive audio, video, or data communications with a patient, onsite patient caregiver, healthcare provider, or consultant.

Telemedical, Outpatient, Managed Care Health Programs

Disclosed herein, in certain embodiments, are methods of operating a telemedical, outpatient, managed care health program comprising providing health program administration or healthcare services by one or more telemedical care providers utilizing computer systems comprising: a software module for telecommunication between the one or more telemedical care providers and a subject or a caregiver for the subject; a software module for diagnostic or therapeutic analysis of the subject; and a software module for monitoring and controlling a remote, point-of-care diagnostic device or a remote, point-of-care therapeutic device; with the proviso that said health program administration or healthcare services involve, exclusively outpatient care and said telemedical care providers refer subjects to a non-telemedical provider if telemedical healthcare alone is determined to be inappropriate. In some embodiments, one or more telemedical care providers are credentialed. In some embodiments, health program administration services include one or more of: enrollment determinations, premium determinations, and authorization of referrals. In some embodiments, a health program provides outpatient care for a term of one year or more. In other embodiments, a health program provides outpatient care for a term of less than one year. In further embodiments, a health program provides outpatient care for a term of less than one month. In still further embodiments, a health program provides outpatient care for a term of less than one week. In still further embodiments, a health program provides outpatient care for a term of less than one day. In some embodiments, a health program provides outpatient care limited to that related to a specific event or health condition. In some embodiments, healthcare services include remote diagnosis or remote therapy. In some embodiments, healthcare services include triaging subjects to higher or lower levels of care. In some embodiments, healthcare services include education. In some embodiments, a co-pay fee is accessed for healthcare services based on the duration of communication between a telemedical care provider and a subject. In some embodiments, diagnostic or therapeutic analysis comprises performing statistical analysis, performing probability calculations, making recommendations, and making outcome predictions to predict a health or economic outcome of a patient or therapy, wherein said prediction is real-time, individualized, and probabilistic-based and uses historic, peer-reviewed health or economic data and emerging health or economic data. In some embodiments, diagnostic or therapeutic analysis comprises: accessing one or more information sources selected from the group consisting of: electronic health records, medical databases, medical literature, economic databases, economic literature, insurance databases, and insurance literature; performing natural language processing to identify information determined to be of value in determining health and economic risks of an adverse outcome related to a health encounter; and transforming said data into numeric format useful for application in statistical modeling to determine risks of an adverse health or economic outcome related to a health encounter. In some embodiments, diagnostic or therapeutic analysis comprises predicting acute risks, with and without one or more potential therapies, based on the severity of a condition and risks associated with each potential therapy to determine the intensity of therapy recommended. In further embodiments, prediction of acute risks is updated in time intervals selected from the group consisting of at least every: 24 hours, 12 hours, 6 hours, 1 hour, 45 minutes, 30 minutes, 15 minutes, 1 minute, 45 seconds, 30 seconds, 15 seconds, and 1 second. In further embodiments, prediction of acute risks is made for a time period selected from the group consisting of: less than 72 hours, less than 48 hours, less than 24 hours, less than 12 hours, less than 8 hours, less than 4 hours, less than 2 hours, and less than 1 hour. In some embodiments, determination of the appropriateness of telemedical healthcare is made based on performing risk stratification regarding an acute adverse health outcome.

Also disclosed herein, in certain embodiments, are computer-implemented systems for providing a telemedical, outpatient, managed care health program comprising: a networked computer comprising a processor, a memory, and an operating system configured to perform executable instructions; a computer program provided to said computer and comprising executable instructions operable to create an telemedical administration application comprising: a module for telecommunications between the one or more telemedical care providers and a subject or a caregiver for the subject; a module for applying diagnostic or therapeutic analysis for the subject; a module for providing an interface adapted to facilitate one or more of: enrollment decisions, premium determinations, determinations of appropriate courses of remote outpatient care for subjects; triage of subjects to higher or lower levels of care if remote outpatient healthcare is inappropriate; and review of referrals to non-remote specialists; optionally, a module for monitoring or controlling one or more remote, point-of-care diagnostic or therapeutic devices; and optionally, a module for monitoring or controlling an apparatus for dispensing one or more medical items from an inventory of medical items.

Also disclosed herein, in certain embodiments, are computer-implemented systems for providing a telemedical, outpatient, managed care health program comprising: a telemedical care provider; a networked computer accessible to said telemedical care provider and comprising a processor, a memory, and an operating system configured to perform executable instructions; a computer program provided to said computer and comprising executable instructions operable to create an telemedical administration application comprising: a module for telecommunications providing said telemedical care provider communications with a subject and access to electronic health records for a subject; a module for providing said telemedical care provider diagnostic or therapeutic analysis for the subject; and a module for providing an interface adapted to allow said telemedical care provider to perform one or more of: enrollment decisions, premium determinations, determinations of appropriate courses of remote outpatient care for subjects; triage of subjects to higher or lower levels of care if remote outpatient healthcare is inappropriate; and review of referrals to non-remote specialists. In some embodiments, the system further comprises a point-of-care medical device accessible to a subject. In further embodiments, a medical device comprises one or more remotely controlled biosensors. In further embodiments, a medical device comprises an apparatus for dispensing medical items to a subject. In some embodiments, a module for monitoring or controlling one or more remote, point-of-care diagnostic or therapeutic devices allows monitoring or controlling one or more remote biosensors. In some embodiments, a module for monitoring or controlling one or more remote, point-of-care diagnostic or therapeutic devices allows monitoring or controlling a remote apparatus for dispensing medical items to a subject. In some embodiments, diagnostic or therapeutic analysis comprises performing statistical analysis, performing probability calculations, making recommendations, and making outcome predictions to predict a health or economic outcome of a patient or therapy, wherein said prediction is real-time, individualized, and probabilistic-based and uses historic, peer-reviewed health or economic data and emerging health or economic data. In some embodiments, diagnostic or therapeutic analysis comprises: accessing one or more information sources selected from the group consisting of: electronic health records, medical databases, medical literature, economic databases, economic literature, insurance databases, and insurance literature; performing natural language processing to identify information determined to be of value in determining health and economic risks of an adverse outcome related to a health encounter; and transforming said data into numeric format useful for application in statistical modeling to determine risks of an adverse outcome health or economic related to a health encounter. In some embodiments, diagnostic or therapeutic analysis comprises predicting acute risks, with and without one or more potential therapies, based on the severity of a condition and risks associated with each potential therapy to determine the intensity of therapy recommended. In further embodiments, prediction of acute risks is updated in time intervals selected from the group consisting of at least every: 24 hours, 12 hours, 6 hours, 1 hour, 45 minutes, 30 minutes, 15 minutes, 1 minute, 45 seconds, 30 seconds, 15 seconds, and 1 second. In further embodiments, prediction of acute risks is made for a time period selected from the group consisting of: less than 72 hours, less than 48 hours, less than 24 hours, less than 12 hours, less than 8 hours, less than 4 hours, less than 2 hours, and less than 1 hour.

Also disclosed herein, in certain embodiments, are methods for administering telemedical, outpatient healthcare to a subject comprising: receiving a request for care for the subject, wherein the subject is a member of a telemedical, outpatient health program; providing a telemedical care provider access to an electronic health record for the subject; creating and maintaining an electronic communications link between the telemedical care provider and the subject or one or more caregivers for the subject; and providing the telemedical care provider access to software for predicting health and economic outcomes for the subject; whereby the telemedical care provider determines an appropriate course of telemedical, outpatient care for the subject and refers the subject to a non-telemedical provider if telemedical healthcare alone is determined to be inappropriate. In some embodiments, the method further comprises the step of identifying a subject. In some embodiments, a request originates with a subject. In other embodiments, a request originates with a non-telemedical healthcare provider. In some embodiments, a communications link supports operation of one or more point-of-care, diagnostic or therapeutic medical devices accessible to a subject. In further embodiments, a medical device comprises one or more remotely controlled biosensors or an apparatus for dispensing medical items to a subject. In some embodiments, an electronic communications link provides live, two-way audio and video communications between a subject and a telemedical care provider. In some embodiments, an electronic communications link provides a three-dimensional representation of a subject and a telemedical care provider in a virtual medical setting. In some embodiments, software for predicting health and economic outcomes comprises: a module configured to transform individualized emerging health or economic data that has been acquired in real-time into at least one model set; a module configured to determine the sufficiency of the model set by comparing the model set against previously accumulated internal data for sufficiency and if necessary prompting for additional data until a preferred confidence level is achieved; a module configured to analyze the model set using at least one statistical model; and a module configured to enhance predictive accuracy by comparing an expected result or outcome to an actual result or outcome to train, re-train, or validate at least one statistical model. In some embodiments, software for predicting health and economic outcomes predicts acute risks, with and without therapy, based on the severity of a condition and risks associated with potential therapy to determine the intensity of therapy recommended. In further embodiments, software for predicting health and economic outcomes predicts acute risks present within 24 hours. In further embodiments, software for predicting health and economic outcomes predicts acute risks present within 12 hours. In further embodiments, software for predicting health and economic outcomes predicts acute risks present within 1 hour.

Also disclosed herein, in certain embodiments, are methods for administering a telemedical, outpatient health program comprising: receiving a request for participation of a subject in a telemedical, outpatient health program; creating and maintaining an electronic communications link between a telemedical care provider and the subject or one or more caregivers for the subject; providing the telemedical care provider access to an electronic health record for the subject; providing the telemedical care provider access to software for predicting health and economic outcomes for the subject; and objectively determining an appropriate enrollment decision or premium determination for the subject. In some embodiments, the method further comprises the step of identifying a subject. In some embodiments, a request originates with a subject. In some embodiments, a request originates with a non-telemedical healthcare provider. In some embodiments, a communications link supports operation of one or more point-of-care, diagnostic or therapeutic medical devices accessible to a subject. In further embodiments, a medical device comprises one or more remotely controlled biosensors or an apparatus for dispensing medical items to a subject. In some embodiments, an electronic communications link provides live, two-way audio and video communications between a subject and a telemedical care provider. In some embodiments, an electronic communications link provides a three-dimensional representation of a subject and a telemedical care provider in a virtual medical setting. In some embodiments, software for predicting health and economic outcomes comprises: a module configured to transform individualized emerging health or economic data that has been acquired in real-time into at least one model set; a module configured to determine the sufficiency of the model set by comparing the model set against previously accumulated internal data for sufficiency and if necessary prompting for additional data until a preferred confidence level is achieved; a module configured to analyze the model set using at least one statistical model; and a module configured to enhance predictive accuracy by comparing an expected result or outcome to an actual result or outcome to train, re-train, or validate at least one statistical model. In some embodiments, software for predicting health and economic outcomes predicts acute risks, with and without therapy, based on the severity of a condition and risks associated with potential therapy to determine the intensity of therapy recommended. In further embodiments, software for predicting health and economic outcomes predicts acute risks present within 24 hours. In further embodiments, software for predicting health and economic outcomes predicts acute risks present within 12 hours. In further embodiments, software for predicting health and economic outcomes predicts acute risks present within 1 hour.

Also disclosed herein, in certain embodiments, are methods for administering telemedical, outpatient healthcare to a subject comprising: receiving a request for care for the subject, wherein the subject is under the care of a licensed primary healthcare payer, or healthcare provider facility, group, or individual maintaining an electronic health record for the subject; providing a telemedical care provider access to said electronic health record for the subject; creating and maintaining an electronic communications link between the telemedical care provider and the subject or one or more caregivers for the subject; and providing the telemedical care provider access to software for predicting health and economic outcomes for the subject; whereby the telemedical care provider determines an appropriate course of telemedical, outpatient care for the subject. In some embodiments, a telemedical care provider is credentialed by a primary healthcare payer or provider to provide telemedical, outpatient care for one or more subjects. In some embodiments, the method further comprises the step of verifying credentials of a telemedical care provider. In some embodiments, the method further comprises the step of identifying a subject. In some embodiments, a request originates with a subject. In other embodiments, a request originates with a caregiver for a subject. In yet other embodiments, a request originates with a primary healthcare provider. In some embodiments, a request includes transmission of one or more electronic medical records for a subject. In some embodiments, electronic health records are historic or live. In some embodiments, a communications link supports operation of one or more point-of-care, diagnostic or therapeutic medical devices accessible to a subject. In further embodiments, a medical device comprises one or more remotely controlled biosensors or an apparatus for dispensing medical items to a subject. In some embodiments, an electronic communications link provides live, two-way audio and video communications between a subject and a telemedical care provider. In some embodiments, an electronic communications link provides a three-dimensional representation of a subject and a telemedical care provider in a virtual medical setting. In some embodiments, software for predicting health and economic outcomes comprises: a module configured to transform individualized emerging health or economic data that has been acquired in real-time into at least one model set; a module configured to determine the sufficiency of the model set by comparing the model set against previously accumulated internal data for sufficiency and if necessary prompting for additional data until a preferred confidence level is achieved; a module configured to analyze the model set using at least one statistical model; and a module configured to enhance predictive accuracy by comparing an expected result or outcome to an actual result or outcome to train, re-train, or validate at least one statistical model. In some embodiments, software for predicting health and economic outcomes predicts acute risks, with and without therapy, based on the severity of a condition and risks associated with potential therapy to determine the intensity of therapy recommended. In further embodiments, software for predicting health and economic outcomes predicts acute risks present within 24 hours. In further embodiments, software for predicting health and economic outcomes predicts acute risks present within 12 hours. In further embodiments, software for predicting health and economic outcomes predicts acute risks present within 1 hour. In some embodiments, the method further comprises the step of referring a subject to a non-telemedical provider if telemedical healthcare alone is determined to be inappropriate.

Also disclosed herein, in certain embodiments, are methods for administering a telemedical, outpatient health program comprising: receiving a request for participation for a subject, wherein the subject is under the care of a licensed primary healthcare payer, or healthcare provider facility, group, or individual maintaining an electronic health record for the subject; providing a telemedical care provider access to said electronic health record for the subject; creating and maintaining an electronic communications link between the telemedical care provider and the subject or one or more caregivers for the subject; providing the telemedical care provider access to software for predicting health and economic outcomes for the subject; and objectively determining an appropriate enrollment decision or premium determination for the subject. In some embodiments, a telemedical care provider is credentialed by a primary healthcare payer or provider to provide remote outpatient care for one or more subject. In some embodiments, the method further comprises the step of verifying credentials of a telemedical care provider. In some embodiments, the method further comprises the step of identifying a subject. In some embodiments, a request originates with a subject. In other embodiments, a request originates with a caregiver for a subject. In yet other embodiments, a request originates with a primary healthcare provider. In some embodiments, a request includes transmission of one or more electronic medical records for a subject. In some embodiments, electronic health records are historic or live. In some embodiments, a communications link supports operation of one or more point-of-care, diagnostic or therapeutic medical devices accessible to a subject. In further embodiments, a medical device comprises one or more remotely controlled biosensors or an apparatus for dispensing medical items to a subject. In some embodiments, an electronic communications link provides live, two-way audio and video communications between a subject and a telemedical care provider. In some embodiments, an electronic communications link provides a three-dimensional representation of a subject and a telemedical care provider in a virtual medical setting. In some embodiments, software for predicting health and economic outcomes comprises: a module configured to transform individualized emerging health or economic data that has been acquired in real-time into at least one model set; a module configured to determine the sufficiency of the model set by comparing the model set against previously accumulated internal data for sufficiency and if necessary prompting for additional data until a preferred confidence level is achieved; a module configured to analyze the model set using at least one statistical model; and a module configured to enhance predictive accuracy by comparing an expected result or outcome to an actual result or outcome to train, re-train, or validate at least one statistical model. In some embodiments, software for predicting health and economic outcomes predicts acute risks, with and without therapy, based on the severity of a condition and risks associated with potential therapy to determine the intensity of therapy recommended. In further embodiments, software for predicting health and economic outcomes predicts acute risks present within 24 hours. In further embodiments, software for predicting health and economic outcomes predicts acute risks present within 12 hours. In further embodiments, software for predicting health and economic outcomes predicts acute risks present within 1 hour.

Also disclosed herein, in certain embodiments, are methods for administering telemedical, outpatient healthcare to a subject comprising: receiving a request for care for the subject; providing a telemedical care provider access to an electronic health record for the subject, where such a record exists; creating and maintaining an electronic communications link between the telemedical care provider and the subject or one or more caregivers for the subject; and providing the telemedical care provider access to software for performing diagnostic or therapeutic analysis for the subject; whereby the telemedical care provider determines an appropriate course of outpatient care for the subject and refers the subject to a non-telemedical provider if telemedical healthcare alone is determined to be inappropriate. In some embodiments, a telemedical care provider is credentialed. In some embodiments, the method further comprises the step of providing a health insurance plan covering financial loss and outpatient care limited to that related to a specific event or health condition. In some embodiments, a fee is accessed for telemedical services based on the duration of communication between a telemedical care provider and a subject. In some embodiments, diagnostic or therapeutic analysis comprises performing statistical analysis, performing probability calculations, making recommendations, and making outcome predictions to predict a health or economic outcome of a patient or therapy, wherein said prediction is real-time, individualized, and probabilistic-based and uses historic, peer-reviewed health or economic data and emerging health or economic data. In some embodiments, diagnostic or therapeutic analysis comprises: accessing one or more information sources selected from the group consisting of: electronic health records, medical databases, medical literature, economic databases, economic literature, insurance databases, and insurance literature; performing natural language processing to identify information determined to be of value in determining health and economic risks of an adverse outcome related to a health encounter; and transforming said data into numeric format useful for application in statistical modeling to determine risks of an adverse health or economic outcome related to a health encounter. In some embodiments, diagnostic or therapeutic analysis comprises predicting acute risks, with and without one or more potential therapies, based on the severity of a condition and risks associated with each potential therapy to determine the intensity of therapy recommended. In further embodiments, a prediction of acute risks is updated in time intervals selected from the group consisting of at least every: 24 hours, 12 hours, 6 hours, 1 hour, 45 minutes, 30 minutes, 15 minutes, 1 minute, 45 seconds, 30 seconds, 15 seconds, and 1 second. In further embodiments, a prediction of acute risks is made for a time period selected from the group consisting of: less than 72 hours, less than 48 hours, less than 24 hours, less than 12 hours, less than 8 hours, less than 4 hours, less than 2 hours, and less than 1 hour.

Also disclosed herein, in certain embodiments, are methods for providing telemedical, outpatient healthcare to a subject comprising the steps of: receiving a request for care for the subject, wherein the subject is a member of a telemedical, outpatient health program; accessing an electronic health record for the subject; conducting electronic communications with the subject or one or more caregivers for the subject; utilizing software for performing a diagnostic or therapeutic analysis for the subject; and conditionally, referring the subject to a non-telemedical provider if telemedical healthcare alone is determined to be inappropriate. In some embodiments, the method further comprises the step of utilizing software for monitoring or controlling one or more remote, point-of-care diagnostic or therapeutic devices accessible by the subject.

Health Program

In some embodiments, disclosed herein are computer-implemented systems for providing a telemedical, outpatient, managed care health program. In some embodiments, disclosed herein are computer-implemented methods of operating a telemedical, outpatient, managed care health program. In further embodiments, disclosed herein are computer-implemented methods for providing healthcare services within a telemedical, outpatient, managed care health program. In still further embodiments, healthcare services involve exclusively outpatient care. In various embodiments, outpatient healthcare services include, by way of non-limiting examples, triaging subjects to higher or lower levels of care, remote diagnosis, remote therapy, operation of a point-of-care diagnostic or therapeutic device, subject education, and the like. In some embodiments, one or more telemedical care providers determines an appropriate course of telemedical, outpatient care for the subject and refers subjects to a non-telemedical provider if telemedical healthcare alone is determined to be inappropriate. In some embodiments, healthcare services are provided to a subject who is a member of a telemedical, outpatient health program. In other embodiments, healthcare services are provided to a subject who is under the care of a licensed primary healthcare payer, or healthcare provider facility, group, or individual maintaining an electronic health record for the subject.

In some embodiments, disclosed herein are computer-implemented methods for administering telemedical, outpatient healthcare. In further embodiments, health program administration involves exclusively outpatient care. In still further embodiments, health program administration includes activities such as enrollment determinations, premium determinations, co-pay calculations, and/or authorization of referrals. In some embodiments, healthcare services are administered for a subject who is a member of a telemedical, outpatient health program. In other embodiments, healthcare services are administered for a subject who is under the care of a licensed primary healthcare payer, or healthcare provider facility, group, or individual maintaining an electronic health record for the subject.

A telemedical, outpatient, managed care health program provides outpatient care for a subject for a wide range of suitable terms (e.g., durations). In various embodiments, a telemedical, outpatient, managed care health program provides outpatient care for a subject for about one year, about one month, about one week, and about one day. In some embodiments, a telemedical, outpatient, managed care health program is long-term and provides outpatient care for a subject for, by way of non-limiting examples, 1, 2, 3, 4, 5, 6, 7, 8, 9, 10 years or more. In some embodiments, a telemedical, outpatient, managed care health program is medium-term and provides outpatient care for a subject for, by way of non-limiting examples, 1, 2, 3, 4, 5, 6, 7, 8, 9, 10, 11, 12 months or more. In some embodiments, a telemedical, outpatient, managed care health program is short-term and provides outpatient care for a subject for, by way of non-limiting examples, 1, 2, 3, 4 weeks or more. In some embodiments, a telemedical, outpatient, managed care health program is short-term and provides outpatient care for a subject for, by way of non-limiting examples, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days or more. In some embodiments, a telemedical, outpatient, managed care health program is ultra short-term and provides outpatient care for a subject for, by way of non-limiting examples, 1, 2, 3, 4, 5, 6, 7, 8, 9, 10, 11, 12, 13, 14, 15, 16, 17, 18, 19, 20, 21, 22, 23, 24 hours or more.

In some embodiments, a telemedical, outpatient, managed care health program provides outpatient care for a subject limited to care related to a specific event or health condition. By way of non-limiting example, a subject becomes a member of a telemedical, outpatient, managed care health program providing healthcare services limited to that reasonably associated with chronic GERD. By way of further non-limiting example, a subject becomes a member of a telemedical, outpatient, managed care health program providing healthcare services limited to that reasonably associated with depression. By way of another non-limiting example, a subject becomes a member of a telemedical, outpatient, managed care health program providing healthcare services limited to that reasonably associated with a trip to Southeast Asia.

The inventions disclosed herein include business methods. In some embodiments, the systems, software, and methods disclosed herein are marketed, advertised, and sold as, for example, products and services for providing telemedical medical diagnosis and/or telemedical, outpatient therapy to a subject. The products and services disclosed herein are particularly well suited for providing low cost healthcare alternatives the uninsured, the underinsured, those in remote and rural areas, and those in developing countries. The products and services disclosed herein are also well suited for supplementation of existing healthcare systems in outpatient, urgent care, or acute situations. The telemedical, outpatient, managed care health programs disclosed herein suitably have many formats, configurations, and financial arrangements.

In some embodiments, a telemedical, outpatient, managed care health program is a healthcare access maintenance membership program (HAMMP). In further embodiments, a HAMMP offers a direct financial relationship with subjects. In still further embodiments, a HAMMP offers membership in a program and/or plan for outpatient, primary, continuing care for chronic diseases and/or acute care telemedically. In some embodiments, a subject obtains membership in a HAMMP by paying a membership fee. In still further embodiments, a membership fee applies to a member's deductible if they have insurance or a health savings account (HSA). In some cases, a HAMMP member makes a request for telemedical, outpatient healthcare utilizing the methods, systems, and software disclosed herein.

In some embodiments, a telemedical, outpatient, managed care health program is part of a health maintenance organization (HMO). In further embodiments, the HMO is a staff model HMO, wherein physicians are direct salaried employees and generally only see HMO members. In further embodiments, the HMO is a group model HMO, wherein the HMO does not employ the physicians directly, but contracts with a multi-specialty physician group practice. In still further embodiments, HMO members select primary care physician (PCP) who oversees care for the subject. In some cases, a PCP or other healthcare provider associated with a HMO refers subjects under their care to a telemedical, outpatient, managed care health program described herein. In further cases, a PCP or other healthcare provider associated with a HMO makes a request for telemedical, outpatient healthcare for a subject utilizing the methods, systems, and software disclosed herein.

In some embodiments, a telemedical, outpatient, managed care health program is part of a preferred provider organization (PPO) or independent practice association (IPA). In further embodiments, a PPO is a managed care organization of medical doctors, hospitals, and other health care providers who have covenanted with an insurer or a third-party administrator to provide health care at reduced rates to the insurer's or administrator's clients. In further embodiments, an IPA is an association of independent physicians, or other organization that contracts with independent physicians, and provides services to managed care organizations on a negotiated per capita rate, flat retainer fee, or negotiated fee-for-service basis. In some cases, a physician or other healthcare provider associated with a PPO or an IPA refers subjects under their care to a telemedical, outpatient, managed care health program described herein. In further cases, a physician or other healthcare provider associated with a PPO or an IPA makes a request for telemedical, outpatient healthcare for a subject utilizing the methods, systems, and software disclosed herein.

In some embodiments, a telemedical, outpatient, managed care health program is a retainer-based or pre-paid health program. In further embodiments, a pre-paid health program offers subjects an opportunity to tender advanced payment for medical services. In some cases, an advanced payment is a retainer for services. In some cases, an advanced payment is held in a deposit or trust account. In further embodiments, the amount of a pre-payment or retainer is calculated based on skill level and/or training of a provider, contact and communication time available with provider, duration of coverage, and the like. In some cases, a retainer-based or pre-paid health program member makes a request for telemedical, outpatient healthcare utilizing the methods, systems, and software disclosed herein.

In some embodiments, a telemedical, outpatient, managed care health program is part of a concierge health program. In further embodiments, a concierge health program offers a direct financial relationship with subjects. In still further embodiments, a subject pre-pays for healthcare or pays on a fee-for-service basis. In some cases, concierge health program member makes a request for telemedical, outpatient healthcare utilizing the methods, systems, and software disclosed herein.

In some embodiments, a telemedical, outpatient, managed care health program is part of a health insurance program and/or plan. In various embodiments, the insurance coverage is, for example, medical insurance, life insurance, property insurance, or combinations thereof. In further embodiments, the insurance coverage is encounter-specific financial insurance coverage. In still further embodiments, encounter-specific insurance covers any loss, financial loss, loss of life, related to a specific remote provider-patient encounter. In further embodiments, the insurance coverage is instantaneous, wherein risk is assessed at the moment a request is made and the coverage issued on the spot. In some embodiments, the insurance includes a level of guarantee and an associated premium.

In some embodiments, the systems and software described herein include, and the methods utilize, a software module for providing insurance coverage for a subject. In some embodiments, a module for applying a diagnostic or therapeutic analysis predicts health or economic outcomes and/or predicts acute risk minute-by-minute. In further embodiments, such real-time projections of adverse health and associated economic outcomes based on the information emerging and historic medical, legal, and financial data are used to calculate a "variable patient encounter specific premium." In still further embodiments, a "variable patient encounter specific premium" is encounter and individual subject specific. In some embodiments, a variable premium takes into consideration all aspects of historic and acute emerging factors described herein.

In some embodiments, the module for providing insurance coverage for a subject includes hardware to print a legally-binding insurance policy. In some embodiments, the module for providing insurance coverage sends a legally-binding insurance policy to a subject, an appropriate caregiver, the subject's primary care provider, or another healthcare entity via electronic methods. In further embodiments, the module for providing insurance coverage sends a legally-binding insurance policy via electronic methods including, by way of non-limiting examples, web posting, email, fax, Internet fax, and the like, including combinations thereof. In still further embodiments, the module for providing insurance coverage for a subject encrypts insurance information prior to sending in order to protect the subject's privacy and to comply with applicable laws.

Insurance

In some embodiments, the systems, devices, software, and methods described herein include a module for providing insurance coverage for a subject. In various embodiments, the insurance coverage is, for example, medical insurance, life insurance, property insurance, or combinations thereof. In further embodiments, the insurance coverage is encounter-specific financial insurance coverage. In still further embodiments, encounter-specific insurance covers any loss, financial loss, loss of life, related to a specific remote provider-patient encounter. In further embodiments, the insurance coverage is instantaneous, wherein risk is assessed at the moment a request is made and the coverage issued on the spot. In some embodiments, the insurance includes a level of guarantee and an associated premium.

In some embodiments, a module for applying a diagnostic or therapeutic analysis predicts health or economic outcomes and/or predicts acute risk minute-by-minute. In further embodiments, such real-time projections of adverse health and associated economic outcomes based on the information emerging and historic medical, legal, and financial data are used to calculate a "variable patient encounter specific premium." In still further embodiments, a "variable patient encounter specific premium" is encounter and individual subject specific. In some embodiments, a variable premium takes into consideration all aspects of historic and acute emerging factors described herein.

In some embodiments, the module for providing insurance coverage for a subject includes hardware to print a legally-binding insurance policy. In some embodiments, the module for providing insurance coverage sends a legally-binding insurance policy to a subject, an appropriate caregiver, the subject's primary care provider, or another healthcare entity via electronic methods. In further embodiments, the module for providing insurance coverage sends a legally-binding insurance policy via electronic methods including, by way of non-limiting examples, email, SMS, MMS, fax, Internet fax, and the like, including combinations thereof. In still further embodiments, the module for providing insurance coverage for a subject encrypts insurance information prior to sending in order to protect the subject's privacy and to comply with applicable laws.

Non-Transitory Computer Readable Medium

In some embodiments, the systems, devices, software, and methods disclosed herein include one or more non-transitory computer readable media encoded with a program including instructions executable by the operating system of an optionally networked digital processing device. In further embodiments, a computer readable medium is a tangible component of a digital processing device. In still further embodiments, a computer readable medium is optionally removable from a digital processing device. In some embodiments, a computer readable medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the systems, devices, software, and methods disclosed herein include at least one computer program. A computer program includes a sequence of instructions, executable in the digital processing device's CPU, written to perform a specified task. Those of skill in the art will recognize that a computer program may be written in various versions of various languages. In some embodiments, a computer program comprises one sequence of instructions. In some embodiments, a computer program comprises a plurality of sequences of instructions. In some embodiments, a computer program is delivered from one location. In other embodiments, a computer program is delivered from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino® A web application for providing a career development network for artists that allows artists to upload information and media files, in some embodiments, includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™ Javascript, Pascal, Object Pascal, Python™, Ruby, VB.NET, WML, and XHTML/HTML with or without CSS, or combinations thereof.

Those of skill in the art will also recognize that mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone® and iPad® (iOS®) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Visual Basic, and VB .NET, or combinations thereof. Compilation is often performed, at least in part, to create an executable program. In some embodiments, a computer program includes one or more executable complied applications.

Software Modules

In some embodiments, the systems, devices, software, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

EXAMPLES

The following illustrative examples are representative of embodiments of the systems, devices, and methods described herein and are not meant to be limiting in any way.

Example 1

Installation of Kiosk in a Pharmacy

A retail pharmacy outlet installs a computer-based kiosk for providing remote medical diagnosis and therapy to their customers, which is part of a larger system for the same purpose. The kiosk includes a module for telecommunications and is connected to the Internet via an Ethernet interface. The module for telecommunications provides audio/video conferencing between the pharmacy's customers and a live, licensed healthcare provider who monitors the system from a remote location outside the United States. The kiosk installation also includes an array of five biosensors chosen to address health issues common in the population that patronizes the pharmacy outlet. The biosensors include a digital scale, a HD video camera, a blood pressure monitor (e.g., sphygmomanometer), a pulse oximeter (e.g., saturometer), and a blood glucose monitor. The sensors are operated by the user and the remote healthcare provider working in concert and coordinating their actions via video conference. The kiosk also includes an apparatus for dispensing OTC and prescription medications from a small inventory. A pharmacist of the retail outlet keeps the kiosk stocked with several commonly prescribed medications including one or more types of insulin, oral hypoglycemics, diuretics, antibiotics, ACE inhibitors, anti-arrhythmics, anti-coagulants, anti-inflammatories, and analgesics, each at a variety of dosages. Each medication is pre-packaged and provided in quantities chosen to provide a short-term supply of medication.

The live, remote healthcare provider utilizes other parts of the system including a module for applying a diagnostic or therapeutic analysis. This module utilizes the Internet connection to access EHRs for each subject from several sources including local healthcare payers and providers. The module for applying a diagnostic or therapeutic analysis predicts health or economic outcomes by applying statistical models to EHRs and health publications as well as emerging news and medical literature. The module utilizes this information including data from the biosensors to predict acute risk for each patient over the next 12 hours, based on analysis that is updated each time the kiosk is consulted. The live, remote healthcare provider also has access to a module for providing instantaneous encounter-specific insurance coverage based on the outcome predictions and risk assessments.

Example 2

Use of Pharmacy Kiosk

A 57-year-old pharmacy customer approaches the kiosk of Example 1 and engages the system by swiping an outpatient, urgent care insurance card. His outpatient, urgent care insurance policy grants him access to the services of the kiosk 24 hours a day. A software module within the kiosk queries a remote database to verify the identity and insurance of the customer.

Prior to this, a physician logged into the system by approaching a work station while carrying an RFID identification card. The physician is licensed to practice medicine in the state where the kiosk is installed. When the customer engages the system, his complete medical record appears on a display screen for the physician's review. The physician sees that the customer has type 2 diabetes and has a history of poor compliance with diet instructions and his prescribed medication regimen. When the physician is ready, she initiates a live audio/video conference with the customer. The kiosk includes an interactive customer interface with a touch screen display. The customer reports that he is feeling ill and has not been in compliance with his diet instructions. Via the HD video camera, the physician can see that the customer is pale and diaphoretic. Issuing verbal instructions and presenting explanatory illustrations on the display screen, she quickly has the customer engage the kiosk's blood pressure monitor and blood glucose monitor features. She immediately is presented with the customer's current blood glucose measurement of 147 mg/dl. The physician determines that the customer is hyperglycemic. The physician is assisted in her examination by risk assessment software, which incorporates the customer's medical history, epidemiological data, real-time medical news data, and data from the biosensors to predict the risk of adverse health outcomes for the customer over the next 12 hours with and without administration of insulin. The software validates her diagnosis and reports low risk that the customer's condition is the result of a differential diagnosis.

The physician swiftly issues a prescription order to the medication dispensing apparatus of the kiosk, which dispenses a syringe of insulin to the customer. She also instructs the customer on administration. A SMS alert is issued to the pharmacist on duty at the retail outlet who observes and assists the customer. Based on a pre-existing agreement, the customer's credit card is charged a fee for the medication.

Example 3

Professional Triage Answering Service

A 50-year-old, male patient experiences shortness of breath after a leisurely walk on a Saturday morning. He has experienced prior heart problems so he immediately calls his cardiologist. Unfortunately, his cardiologist does not regularly see patients on weekends. However, the cardiologist's group has partnered with a professional triage answering service to provide a professional answering service during non-working hours. During non-working hours, calls are directed to a nurse practitioner (NP) who can provide basic medical care. The cardiologist's group had previously verified the NP's credentials by interviewing the NP and checking her medical malpractice insurance coverage, professional references, legal and prescription licenses, and state of licensure. The NP answers the patient's call and notes the symptoms. Using a software program, the NP accesses the group's electronic health records including the patient's previous medical history.

The NP supplements her professional judgment by entering the circumstances of the emerging situation and importing the patient's historic health records into a software program designed to make real-time predictions of health outcomes of a patient and potential therapies utilizing statistical analysis of emerging data. The software determines the probability that the condition is a mild allergic reaction to pollen in which the software recommends prescribing an oral anti-histamine. The software also determines the probability that the condition is an asthma attack in which the software recommends prescribing a bronchodilator and employing a remote, portable auscultation device to record and transmit the patient's breath sounds to check for wheezing. And, the software also determines the probability that the condition is more severe and the live, remote, adjunct healthcare provider should call 911 in the patient's jurisdiction.

Based on the symptoms provided, the medical history, and the probabilistic outcome predictions, the NP triages the patient, determining the medical severity of illness, the intensity of service required, who should perform required services, and recommended timeline of events. The NP instructs the patient on the next course of action, which is an immediate prescription for a bronchodilator, updates the patient's history in the group's electronic health records, and notifies the patient's cardiologist that a follow-up call is in order. A software program records all of the communications electronically for later review. The total elapsed time of the session is less than 10 minutes.

Example 4

Live, Remote, Adjunct Triage

A 25-year-old female researcher in Antarctica is experiencing coughing and fever. The nearest medical facility is at least few hundred miles away. The research station is only equipped to provide basic first aid care and medication. However, the station is partnered with a live, remote, adjunct triage system and equipped with a biometric sensor and a portable, electronic imaging device. The researcher suspects that she has contracted pneumonia, which usually requires immediate treatment, but she is not sure. Using a video conference system, the researcher connects to a live, remote, adjunct provider. The provider, a physician assistant (PA) located in California, is credentialed by the researcher's healthcare provider who verified the PA's education, training, certifications, references, prescription license, malpractice insurance coverage, and state license and state of licensure. The PA asks basic questions about the researcher's symptoms and examines the researcher visually. To gather additional information, the PA instructs the researcher to use the biometric sensor and the electronic imaging device equipped in the station. The biometric sensor measures the researcher's vital signs and other biometric data such as her body temperature, heart rate, blood pressure, and respiratory rate. Using the portable imaging device, another researcher takes a chest x-ray.

The PA obtains the researcher's consent to access her electronic health records. Using a software program, which is updated regularly to meet applicable legal requirements, the PA accesses the researcher's medical history, medication history, family history, and other relevant information.

At the same time, the above data are transmitted to another software program designed to predict a health outcome of a patient. The prediction is real-time, individualized, and probabilistic-based, and it uses an emerging health data. The software determines the triage level, specific care required and the nearest healthcare provider suited for the care. The software further suggests a prescription and a referral to a specialist. The PA validates the result from the prediction software using his professional judgment and determines that immediate care is needed.

Example 5

Live, Remote, Adjunct Triage of In-Patient

In order to extend its patient care effectiveness, a large metropolitan hospital has recently decreased its overnight medical staff to a minimum level and instituted a live, remote, adjunct triage service system to evaluate any overnight, in-patient care issues. A 33-year-old male is an in-patient of the hospital. Shortly after 2 a.m., he starts experiencing sharp pain in his abdomen. An attendant on duty initiates the remote adjunct triage system by identifying the patient and describing the symptoms briefly into a laptop computer at the patient's bedside. The system analyzes the data and opens a video link with a live, remote, adjunct physician assistant (PA) in Australia. The PA was previously credentialed by the hospital which verified the PA's education, training, certifications, references, prescription license, malpractice insurance coverage, and state license and state of licensure.

The PA obtains the patient's consent to access his electronic health records. Using a software program, the PA accesses the patient's medical history, medication history, family history, and other relevant information. The software is updated regularly to meet applicable legal standards. The attendant on duty measures the patient's vital signs and other biometrics and updates the patient's electronic health records. The PA is very concerned and convenes a remote, live consultative panel comprised of physicians licensed in the patient's state or elsewhere (and not necessarily credentialed by the patient's primary healthcare provider) including a gynecologist, a urologist, and a general surgeon to arrive at a consensus recommendation for the optimal plan of care.

Based on the consensus recommendation, the PA orders an ultrasound. Using a portable imaging device, the attendant takes an ultrasound image of the patient, and the result is directly sent to a radiologist in Switzerland. At 5:43 a.m., the radiologist in Switzerland presents her findings to the PA over a VoIP connection. By this time, the patient's pain has subsided, and the PA prescribes pain medicine for the patient in case the pain returns. The prescription is directly updated into the electronic health records. The result is a patient that is well cared for while the patient's primary physicians are undisturbed during their non-working hours.

At 8:00 a.m. the next morning, the patient is stable and ready for discharge, however it is anticipated that the patient's primary physician will be unavailable to evaluate the patient due to the another urgent situation. A hospital staff member again initiates contact with a live, remote, adjunct healthcare provider who authorizes the patient's discharge home and electronically contacts the patient's preferred pharmacy with medication prescriptions. The result is prevention of an unnecessarily prolonged length of stay and a bed in the hospital being opened to other patients in need sooner.

Example 6

Healthcare Access Maintenance Membership Program

A 32-year-old male subject with type 2 diabetes is a member of a HMO. He is under the care of a primary care physician associated with an IPA, which contracts with the HMO to provide services to its members. The IPA maintains electronic health records for the subject and further contracts with a healthcare access maintenance membership program (HAMMP) to reduce the cost of outpatient care by providing a telemedical option to their patients, including the subject. The subject is provided with a HAMMP membership, which complements his HMO membership and renders him eligible for round-the-clock, telemedical, outpatient services where such services are appropriate.

The subject may contact a telemedical care provider at any time using a mobile application installed on his smartphone. During any contact, a telemedical care provider will utilize specialized software to communicate with the subject, access electronic health records for the subject maintained by his primary care physician, and statistically assess risks to his health. Because he has diabetes, his primary care physician also provides him with a blood glucose monitor that communicates with his phone and the mobile application via Bluetooth. During any contact, a telemedical care provider can request that he perform a blood glucose test, data from which is automatically presented to the telemedical care provider and provided to the software for risk assessment.

Example 7

Telemedical, Outpatient, Managed Care Health Program

A 61-year-old female subject is not yet eligible for Medicare and cannot afford comprehensive health insurance. She purchases a high deductable health insurance policy and supplements her access to healthcare services by becoming a member of a telemedical, outpatient, managed care health program. At the time she applies for membership, her health records are reviewed and an annual membership fee determined Her annual membership provides her access to telemedical, outpatient healthcare services provided remotely by a telemedical care provider. She may make a direct request for telemedical healthcare from her home by telephone or internet. She may also visit any one of a number of dedicated kiosks installed for this purpose in pharmacies in her area. She pays a co-payment for use of her membership that is determined based on the number of contacts she makes with her telemedical care providers and the duration of each contact.

In one particular instance, the female subject is experiencing mild vertigo. She uses her laptop computer to contact a telemedical care provider associated with her telemedical, outpatient, managed care health program. The program includes a suite of software applications that her telemedical care provider utilizes in responding to her contact. First, the telemedical care provider, who is a nurse practitioner supervised in her activities by a staff telemedicologist, uses a software module to establish an audio/video conference with the female subject. Another software module retrieves health records for the subject from a number of electronic sources simultaneously. The telemedical care provider interviews the subject and inputs information into an interface associated with a third software module for performing statistical diagnostic analysis. This module utilizes historic medical data as well as the information from the current contact to predict a risk of mortality or morbidity for the subject's current complaint. Utilizing these tools, the telemedical care provider determines telemedical, outpatient care is appropriate.

Based on further medical interview questions, the telemedical care provider diagnoses the subject with a middle ear infection and utilizes the communications module to conference in a licensed pharmacist to consult on an appropriate prescription, which is called in to a pharmacy nearby the subject's home.

Example 8

Telemedical, Outpatient, Managed Care Health Program

In another particular instance, the female subject of Example 7 is experiencing difficulty breathing while on a grocery shopping trip. She approaches a telemedical kiosk in a pharmacy present in the grocery store. She swipes a membership card in a card reader integrated with the kiosk. Her card swipe triggers a number of actions. First, the subject is identified to the system. Second, an audio/video communication channel is created between the subject and a telemedical care provider. In this case, the telemedical care provider is a telemedicologist who is board certified in internal medicine and has completed a post-graduate fellowship in telemedicology. Third, the subject's electronic health records are automatically retrieved from a number of sources and presented to the telemedical care provider in summary format.

The telemedical care provider begins to interview the subject and upon hearing the subject's description of her symptoms, he engages a software module that predicts health outcomes in order to assist his diagnostic and therapeutic analysis. This module utilizes natural language processing and machine learning to perform statistical modeling of health outcomes from historic and real-time health and economic data. The module is continually engaged in an algorithm training process to refine its natural language processing and probabilistic classifier sub-modules. As the telemedical care provider enters data regarding the current contact, the module predicts acute risks present for the subject over the next 12 hours, recalculating the prediction every 30 seconds.

The telemedical care provider asks the subject to place her right arm into a biosensor device integrated with the kiosk. The telemedical care provider remotely operates the device to measure the subject's heart rate, blood oxygen, and blood pressures. The results of these measurements are presented to the telemedical care provider and also provided to the software module for predicting health outcomes and performing diagnostic analysis.

Based on the risks present and on his experience as a physician, the telemedical care provider determines that outpatient, telemedical care is inappropriate for the current situation and recommends that the subject immediately seek emergency care.

Example 9

Statistical Model Prototype

A simulation was introduced in order to derive and evaluate candidate statistical methodologies for the probabilistic classier aspect of a software module for applying a diagnostic or therapeutic analysis. A prototype was developed to demonstrate typical use-case examples. The prototype addressed the case of subjects who appear at a point-of-care complaining about any of the following:
1. Abdominal pain
2. Bradycardia
3. Chest pain
4. Dizziness
5. Dyspnea
6. Hypertensive urgency or emergency
7. Hypotension
8. Hypoxia
9. Jaw pain
10. Pre-syncope
11. Syncope
12. Tachycardia
13. Transient neurologic deficits
14. Upper extremity pain
15. Headache One thousand cases were simulated with 35 variables, including demographic characteristics, medical history, objective biological symptoms, subjective evaluations, and plans of actions. Variable distributional assumptions were provided by the inventors. Variables were assumed to be independent; thus, no correlation structure was introduced. The response variable was risk of mortality and was empirically evaluated by the inventors. Mortality class labels were generated according to the probabilities that the inventors provided. The survival:death ratio in the dataset was 6:1. The system comprised SOAP variables and the outcome was the risk of an adverse outcome. The Assessment and Plan variables are not extracted but given. Descriptions for each set are provided below.

Subjective:
This set of variables included:
1. Age: The age of the subject
2. Gender: The gender of the subject
3. History of Diabetes (Hx Diabetes), varying from 0-100 with 100 being most severe
4. History of Coronary Stent (Hx Corstent), varying from 0-100 with 100 being most severe
5. History of Myocardial Infarction (Hx MI), varying from 0-100 with 100 being most severe
6. History of Congestive Heart Failure(Hx CHF), varying from 0-100 with 100 being most severe
7. History of Coronary Artery Bypass Graft (Hx CABG), varying from 0-100 with 100 being most severe
8. History of End Stage Renal Disease(Hx ESRD), varying from 0-100 with 100 being most severe
9. History of Cerebral Vascular Transient Ischemic Attack (Hx CV TIA), varying from 0-100 with 100 being most severe
10. History of Vascular Stent (Hx VASC STENT), varying from 0-100 with 100 being most severe Objective:
This set of variables included:
1. Systolic Blood Pressure (SBP), varying from 100 to 250, with <90 and >180 being more severe
2. Diastolic Blood Pressure (DBP), varying from 30 to 180, with <50 and >110 being more severe
3. Heart Rate (HR), varying from 30 to 40, with <50 and >150 being more severe
4. Respiratory Rate (RR), varying from 5 to 50, with >24 being more severe
5. Temperature (TEMP), varying from 33° to 40°, with <34° and >38.5° being more severe
6. Oxygen Saturation (SAT), varying from 70 to 100, with <88 being more severe
7. Troponin, varying from 0 to 1000, with >150 being more severe
8. Beta Natriuretic Peptide, varying from 0 to 5000, with >500 being more severe
9. Glucose, varying from 20 to 700, with >500 being more severe Assessment:
This set of variables included the likelihood of the following differential diagnoses:
1. Acute Myocardial Infarction: Likelihood of Acute Myocardial Infarction
2. Atypical Chest Pain: Likelihood of Atypical Chest Pain Plan:
This set of variables included a sequence of treatment plans performed to a particular subject. Values represent intensity of service. All plans range from 0-100, besides CABG and Pace, that are binary (0-1).
1. Cardiopulmonary Resuscitation (CPR)
2. ICU-Cardiac Care Unit (ICU CCU)
3. IV Nitroglycerin (IV NTG)
4. IV Heparin (IV HEP)
5. IV Epinephrine (IV EPI)
6. IV Vasopressin (IV BP)
7. IV Anti-Arrhythmia (IV ANTI ARRH)
8. Catheter (CATH)
9. Stent (STENT)
10. Plasminogen Tissue Activator (PTA)
11. Coronary Artery Bypass Graft (CABG)
12. TRANFt (CABG)
13. Pace-maker (Pace)
14. Dialysis (Urg Dialysis)

We found that Stochastic Gradient Boosting (SGB) had the best performance among other classifiers in this experiment; hence this method was used for the implementation of the prototype. We used 90% of the data for training and the remaining 10% for testing. Also, given that the data had a sensitive class, i.e., a class who should not be misclassified (Mortality), costing was implemented, to avoid this undesirable misclassification. To do this, a "cost" was assigned to each class, where the sensitive class received the highest cost. Then, the training dataset was filtered by discarding (not training with) certain data in a way that is proportional to their costs. This provided a training dataset that had a higher proportion of the sensitive class. Finally a combination of cost-sensitive SGB models was built. Heuristically, 20 rounds were sufficient. The parameters of each SGB model, namely the learning rate v, the number of iterations and the tree depth, were chosen by 10-fold cross-validation on the initial training set. The algorithm utilized for this task is described below.

| Algorithm 1 Train M SGB models using cost-sensitive sampling |
| --- |
| 1: Do 10-fold cross-validation to find optimal training parameters (v, number of iterations, and tree depth) for SGB |
| 2: Select desired cost-sampling parameters |
| 3: for j = 1 to M do |
| 4:  Build new cost-sensitive dataset j by sampling from training dataset |
| 5:  Train SGB model in training dataset j using cross-validated parameters obtained in 1 |
| 6: end for |
| 7: Combine SGB models by averaging all regression trees |

Figure 26:
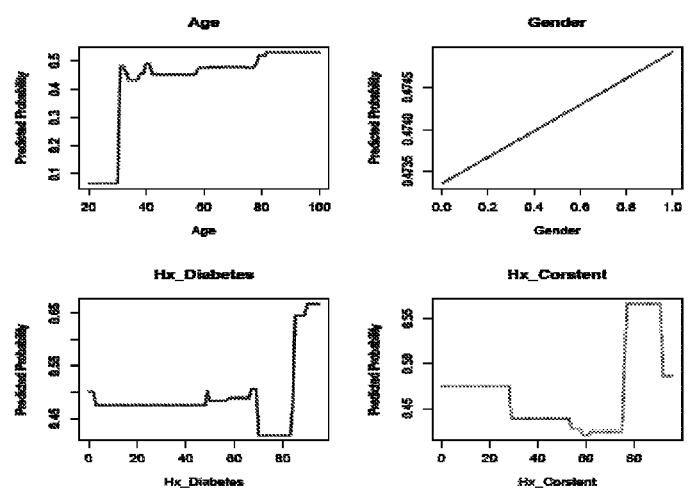
FIGS. 26 and 27 show results from the statistical simulation of Example 9.
Figure 27:
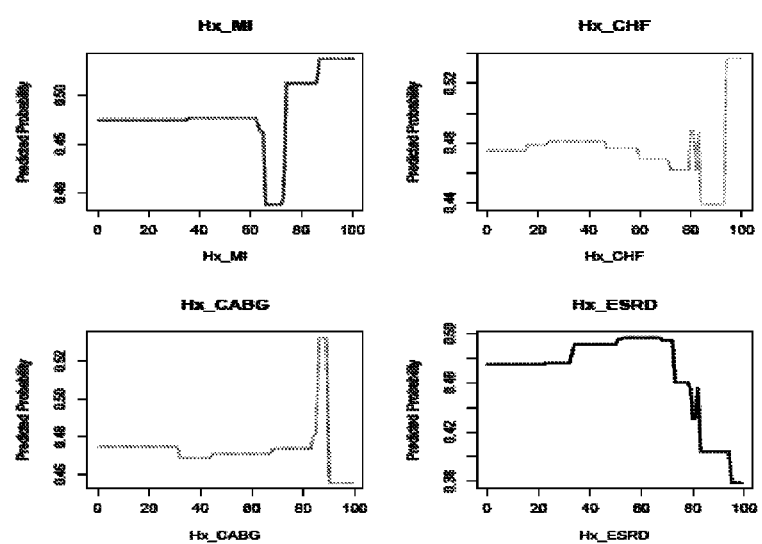

The final combined model had better performance than models that were trained without costing. Specifically, an accuracy of 86% was achieved on mortality and 45% on survival on the test set, while without costing accuracies were 3% and 98% respectively. To explore the effects of all variables, a base case subject having the average value for each variable was generated. All of the variables were held constant apart from the variable of interest and this information was fed to the final model. FIGS. 26 and 27 show how selected variables of interest affected the probability of mortality.

Referring to FIG. 26, the probability of mortality increased as age increases as predicted by the prototype model. Gender had no meaningful effect. Hx Diabetes had a serious effect after a value of 80, similar to Hx Corstent.

Referring to FIG. 27, the results for larger values of Hx MI and Hx CHF were expected. Hx ESRD showed a decrease in the probability of mortality for higher risk values, possibly due to a lack of subjects in the dataset with higher values for Hx ESRD.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A computer-based device comprising:
   a. a processor, an operating system configured to perform executable instructions, and a memory;
   b. a non-refillable disposable apparatus for dispensing one or more medical items from a short-term inventory of medical items wherein the short-term inventory of medical items is contained within the portable, non-refillable, disposable apparatus;
   c. a computer program including instructions executable by the computer-based device to create an application comprising:
      i. a software module for conducting real-time telecommunications with a live, remote telemedical care provider; and
      ii. a software module for applying a diagnostic or a therapeutic analysis;
         wherein the diagnostic or the therapeutic analysis comprises a probability calculation of a future adverse change in health and an increase in economic risk to a subject, a population, a venue, or a situation prior to onset of the future adverse change in health and the increase in economic risk;
         wherein the short-term inventory of medical items contained within the portable, non-refillable, disposable apparatus is selected and provided in accordance with a risk profile based on the probability calculation of the future adverse change in health and increase in economic risk to the subject, the population, the venue, or the situation in advance of medical necessity for the medical items;
         wherein the short-term inventory of medical items consists essentially of a less than one week supply of a medication;
         wherein the computer-based device is configured for providing remote medical diagnosis and therapy to a subject in a secure electronic healthcare encounter.

2. The device of claim 1, further comprising a software module for verifying credentials of a telemedical care provider.

3. The device of claim 1, further comprising a software module for remote monitoring or operation of the device by the telemedical care provider.

4. The device of claim 1, further comprising a software module for identifying the subject.

5. The device of claim 4, further comprising a software module for securely accessing one or more electronic health records for the subject.

6. The device of claim 1, wherein the inventory of medical items is determined by profiling the future adverse change in health and the increase in economic risk for a subject or a population in advance of medical necessity for said medical items.

7. The device of claim 1, wherein the inventory of medical items is risk profiled by determining a statistical level of likelihood that the items will become medically necessary within 2 years, within 1 year, within 6 months, within 1 month, within 2 weeks, within 1 week, or within 1 day.

8. The device of claim 1, wherein the inventory of medical items comprises items that require a prescription from a licensed healthcare provider.

9. The device of claim 8, wherein the inventory of medical items comprises: one or more medications, one or more therapeutic devices, one or more diagnostic devices, or one or more diagnostic kits.

10. The device of claim 1, further comprising a biosensor adapted to collect medical information from a subject or the subject's environment.

11. The device of claim 1, wherein the diagnostic or therapeutic analysis comprises performing statistical analysis, performing probability calculations, making recommendations, and making outcome predictions to predict a health or economic outcome of a patient or therapy, wherein said prediction is real-time, individualized, and probabilistic-based and uses historic, peer-reviewed health or economic data and emerging health or economic data.

12. The device of claim 1, wherein the diagnostic or therapeutic analysis comprises:
   a. accessing one or more information sources selected from the group consisting of: electronic health records, medical databases, medical literature, economic databases, economic literature, insurance databases, and insurance literature;
   b. performing natural language processing to identify information determined to be of value in determining health and economic risks of an adverse outcome related to a health encounter; and
   c. transforming said data into numerical format useful for application in statistical modeling to determine health and economic risks of an adverse outcome related to a health encounter.

13. The device of claim 1, wherein the diagnostic or therapeutic analysis comprises predicting acute risks, with and without one or more potential therapies, based on the severity of a condition and risks associated with each potential therapy to determine the intensity of therapy recommended.

14. The device of claim 13, wherein the prediction of acute risks is updated in time intervals selected from the group consisting of: at least every 24 hours, at least every 12 hours, at least every 6 hours, at least every 1 hour, at least every 45 minutes, at least every 30 minutes, at least every 15 minutes, at least every 1 minute, at least every 45 seconds, at least every 30 seconds, at least every 15 seconds, and at least every 1 second.

15. The device of claim 13, wherein the prediction of acute risks is made for a time period selected from the group consisting of: less than 72 hours, less than 48 hours, less than 24 hours, less than 12 hours, less than 8 hours, less than 4 hours, less than 2 hours, and less than 1 hour.

16. The device of claim 1, further comprising a software module for processing payment.

17. The computer-based device of claim 1, wherein the software module for conducting telecommunications with a live, remote telemedical care provider is adapted for telecommunications comprising medication reconciliation, patient education, and initiation of treatment.

18. The computer-based device of claim 1 for providing an outpatient electronic concierge health maintenance program.

19. A system comprising:
   a. a first networked device comprising a processor configured to perform executable instructions, the first device comprising:
      a portable, non-refillable, disposable apparatus for dispensing one or more medical items from a short-term inventory of medical items, wherein the inventory of medical items contained within the portable, non-refillable, disposable apparatus is selected and provided in accordance with a risk profile based on a probability calculation of a future adverse change in health and increase in economic risk to a subject, a population, a venue, or a situation in advance of medical necessity for the medical items, and wherein the short-term inventory of medical items consists essentially of a less than one week supply of a medication;

b. a second networked device comprising a processor configured to perform executable instructions, the second device optionally comprising at least one biosensor, wherein the first and second networked devices each comprise a computer program including instructions executable by the device to create an application comprising:
  i. a module for remote monitoring or operation by a live, remote telemedical care provider;
  ii. a module for real-time telecommunications with a live, remote telemedical care provider; and
  iii. a module for applying a diagnostic or a therapeutic analysis, the diagnostic or a therapeutic analysis comprising a probability calculation of the future adverse change in health and the increase in economic risk to a subject, a population, a venue, or a situation prior to onset of the future adverse change in health and the increase in economic risk;

c. a networked computer comprising a processor configured to perform executable instructions, the computer accessible to a live, remote telemedical care provider, the computer provided a computer program including instructions executable by the computer to create an application comprising:
  i. a module for telecommunications between the first or second device, or a user thereof, and the telemedical care provider;
  ii. a module for applying a diagnostic or a therapeutic analysis, the diagnostic or a therapeutic analysis comprising a probability calculation of health or economic risk to a subject, a population, a venue, or a situation; and
  iii. a module for remotely monitoring or operating the first or second device;
    provided that the system is configured for providing remote medical diagnosis and therapy to a subject in a secure electronic healthcare encounter.

20. The system of claim 19, wherein the inventory of medical items is determined by profiling the future adverse change in health and the increase in economic risk for a subject or a population in advance of medical necessity for said medical items.

21. The system of claim 19, wherein the inventory of medical items is risk profiled by determining a statistical level of likelihood that the items will become medically necessary within 2 years, within 1 year, within 6 months, within 1 month, within 2 weeks, within 1 week, or within 1 day.

22. The system of claim 19 for providing an outpatient concierge health maintenance program.

23. A non-transitory computer readable media encoded with a computer program including instructions executable by a processor to create a remote, acute healthcare application, wherein the application comprises:
  a. a software module for conducting real-time telecommunications with a live, remote telemedical care provider;
  b. a software module for applying a diagnostic or a therapeutic analysis, the diagnostic or a therapeutic analysis comprising a probability calculation of a future adverse change in health and increase in an economic risk to a subject, a population, a venue, or a situation prior to onset of an adverse change in health;
  c. optionally, a software module for monitoring or operating a biosensor;
  d. a software module for monitoring or operating a portable, non-refillable, disposable apparatus for dispensing one or more medical items from a short-term inventory of medical items, wherein the inventory of medical items contained within the portable, non-refillable, disposable apparatus is selected and provided in accordance with a risk profile based on the probability calculation of the future adverse change in health and the increase in economic risk to the subject, the population, the venue, or the situation in advance of medical necessity for the medical items, the short-term inventory of medical items consisting essentially of a less than one week supply of a medication; and
  e. a software module for providing instantaneous healthcare encounter-specific financial insurance coverage, wherein said insurance includes a level of guarantee to offset economic risks associated with administration of a medical item and an associated premium;
    provided that said software modules are supervised or operated by a live, remote telemedical care provider in a secure electronic healthcare encounter.

24. The non-transitory computer readable media of claim 23, wherein the telecommunications comprise medication reconciliation, patient education, and initiation of treatment.

25. The non-transitory computer readable media of claim 23, wherein the application is for providing an outpatient electronic concierge health maintenance program.

* * * * *